US012569508B2

(12) United States Patent
Thorn et al.

(10) Patent No.: US 12,569,508 B2
(45) Date of Patent: Mar. 10, 2026

---

(54) ANTIMICROBIAL COMPOSITIONS AND METHODS OF USE

(71) Applicant: University of South Australia, Adelaide (AU)

(72) Inventors: Chelsea Thorn, Largs Bay (AU); Nicky Thomas, Clearview (AU); Clive Prestidge, Semaphore South (AU)

( * ) Notice: Subject to any disclaimer, the term of this patent is extended or adjusted under 35 U.S.C. 154(b) by 424 days.

(21) Appl. No.: 18/031,762

(22) PCT Filed: Oct. 13, 2021

(86) PCT No.: PCT/AU2021/051195
§ 371 (c)(1),
(2) Date: Apr. 13, 2023

(87) PCT Pub. No.: WO2022/077060
PCT Pub. Date: Apr. 21, 2022

(65) Prior Publication Data
US 2023/0390316 A1　　Dec. 7, 2023

(30) Foreign Application Priority Data

Oct. 13, 2020　　(AU) ................................ 2020903710

(51) Int. Cl.
| | |
|---|---|
| A61K 31/7036 | (2006.01) |
| A61K 9/1274 | (2025.01) |
| A61K 38/12 | (2006.01) |
| A61K 47/10 | (2017.01) |
| A61K 47/14 | (2017.01) |
| A61P 17/02 | (2006.01) |
| A61P 31/04 | (2006.01) |

(52) U.S. Cl.
CPC ........ *A61K 31/7036* (2013.01); *A61K 9/1274* (2013.01); *A61K 38/12* (2013.01); *A61K 47/10* (2013.01); *A61K 47/14* (2013.01); *A61P 17/02* (2018.01); *A61P 31/04* (2018.01)

(58) Field of Classification Search
CPC .......................... A61K 31/7036; A61P 17/02
See application file for complete search history.

(56) References Cited

FOREIGN PATENT DOCUMENTS

| | | |
|---|---|---|
| WO | WO 2015/168523 A1 | 11/2015 |
| WO | WO 2019/074422 A1 | 4/2019 |
| WO | WO 2020/035483 A1 | 2/2020 |

OTHER PUBLICATIONS

International Search Report and Written Opinion issued for PCT/AU2021/051195 on Jan. 18, 2022 (13 pages).
Alharbi et al., "Development and optimization of ocular in situ gels loaded with ciprofloxacin cubic liquid crystalline nanoparticles," *Journal of Drug Delivery Science and Technology* 57:101710, Apr. 1, 2020 (11 pages).

Boge et al., "Lipid-based liquid crystals as carrier for antimicrobial peptides: phase behavior and antimicrobial effects," *Langmuir* 32(17):4217-4228, Mar. 31, 2016.
Boge et al., "Cubosomes post-loaded with antimicrobial peptides: characterization, bactericidal effect and proteolytic stability," *International Journal of Pharmaceutics* 526(1-2):400-412, May 3, 2017.
Boge et al., "Freeze-dried and re-hydrated liquid crystalline nanoparticles stabilized with disaccharides for drug-delivery of the plectasin derivative AP114 antimicrobial peptide," *Journal of Colloid and Interface Science* 522:126-135, Mar. 20, 2018.
Boge et al., "Cubosomes for topical delivery of the antimicrobial peptide LL-37," *European Journal of Pharmaceutics and Biopharmaceutics* 134:60-67, Nov. 13, 2018.
Lai et al., "Phytantriol-based cubosome formulation as an antimicrobial against lipopolysaccharide-deficient gram-negative bacteria," *ACS Applied Materials and Interfaces* 12:44485-44498, Sep. 18, 2020.
Meikle et al., "Preparation, Characterization, and Antimicrobial Activity of Cubosome Encapsulated Metal Nanocrystals," *ACS Applied Materials and Interfaces* 12(6):6944-6954, Jan. 2020.
Thorn et al., "*Pseudomonas* infection responsive liquid crystals for glycoside hydrolase and antibiotic combination," *ACS Applied Bio Materials* 1(2):281-288, Jul. 13, 2018.
Thorn et al., "Bacterial lipase triggers the release of antibiotics from digestible liquid crystal nanoparticles," *Journal of Controlled Release* 319:168-182, Dec. 24, 2019.
Tran et al., "Non-lamellar lyotropic liquid crystalline nanoparticles enhance the antibacterial effects of rifampicin against *Staphylococcus aureus,*" *Journal of Colloid and Interface Science* 519:107-118, Feb. 16, 2018.
Yeh et al., "Nano-based drug delivery or targeting to eradicate bacteria for infection mitigation: a review of recent advances," *Frontiers in Chemistry* 8:286, Apr. 24, 2020 (22 pages).

*Primary Examiner* — Amber D Steele
(74) *Attorney, Agent, or Firm* — Klarquist Sparkman, LLP

(57) ABSTRACT

The present invention relates to antimicrobial compositions and methods for their use. In particular, the compositions comprise an antimicrobial agent and a nanostructured liquid crystal carrier, wherein the antimicrobial agent is contained within the nanostructured liquid crystal carrier, and wherein the nanostructured liquid crystal carrier potentiates the activity of the antimicrobial agent. Antimicrobial agents encompassed by the present invention include cationic antibiotics, antimicrobial peptides, and antifungal agents. Nanostructured liquid crystal carriers encompassed by the present invention include those formed from an amphiphilic lipid such as monoolein and phytantriol. Antimicrobial compositions encompassed by the present invention can be used for the treatment or prevention of a microbial infection, such as that caused by a Gram-negative bacterium, including where the microbial infection forms part of a biofilm. The present invention also relates to methods for reducing the viability of a microorganisms, for potentiating the activity of an antimicrobial agent, for reducing the dose of an antimicrobial agent required to treat or prevent a microbial infection, or for increasing the potency of an antimicrobial agent required to treat or prevent a microbial infection, by administering an antimicrobial composition described herein. Kits comprising the antimicrobial compositions are also encompassed by the present invention.

20 Claims, 19 Drawing Sheets

FIG. 1

| LCNPs | Particle size (nm) | PDI | Zeta Potential (mV) | TOB loaded (% w/w) | Release rate (μg/min$^{1/2}$) |
|---|---|---|---|---|---|
| Phytantriol (PHY)-LCNPs | 313 ± 6 | 0.56 ± 0.03 | -11.2 ± 1.0 | 21 | 272 |
| Monoolein (MO)-LCNPs (0.3% w/v Pluronic F-127) | 164 ± 2 | 0.16 ± 0.01 | -10.4 ± 0.4 | 25 | 208 |
| MO-LCNPs (5% w/v Pluronic F-127) | 85.4 ± 1 | 0.17 ± 0.01 | -16.1 ± 0.5 | 26 | - |
| MO-LCNPs (no Pluronic F127) | 183 ± 2 | 0.11 ± 0.01 | -10.2 ± 0.1 | 21 | - |
| DSPC: DPPG liposomes | 149 ± 8 | 0.37 ± 0.01 | -43.5 ± 0.12 | 3 | 42 |

FIG. 2

| TOB formulations | Particle size (nm) | PDI | Zeta potential (mV) | Total Mass Deposited (µg) |
|---|---|---|---|---|
| Unformulated | - | - | - | 10.8 ± 0.3 |
| PHY- | 247 ± 12 | 0.32 ± 0.01 | -1.1 ± 0.1 | 10.4 ± 0.2 |
| MO- | 199 ± 3 | 0.37 ± 0.01 | -2.1 ± 0.1 | 13.5 ± 0.4 |

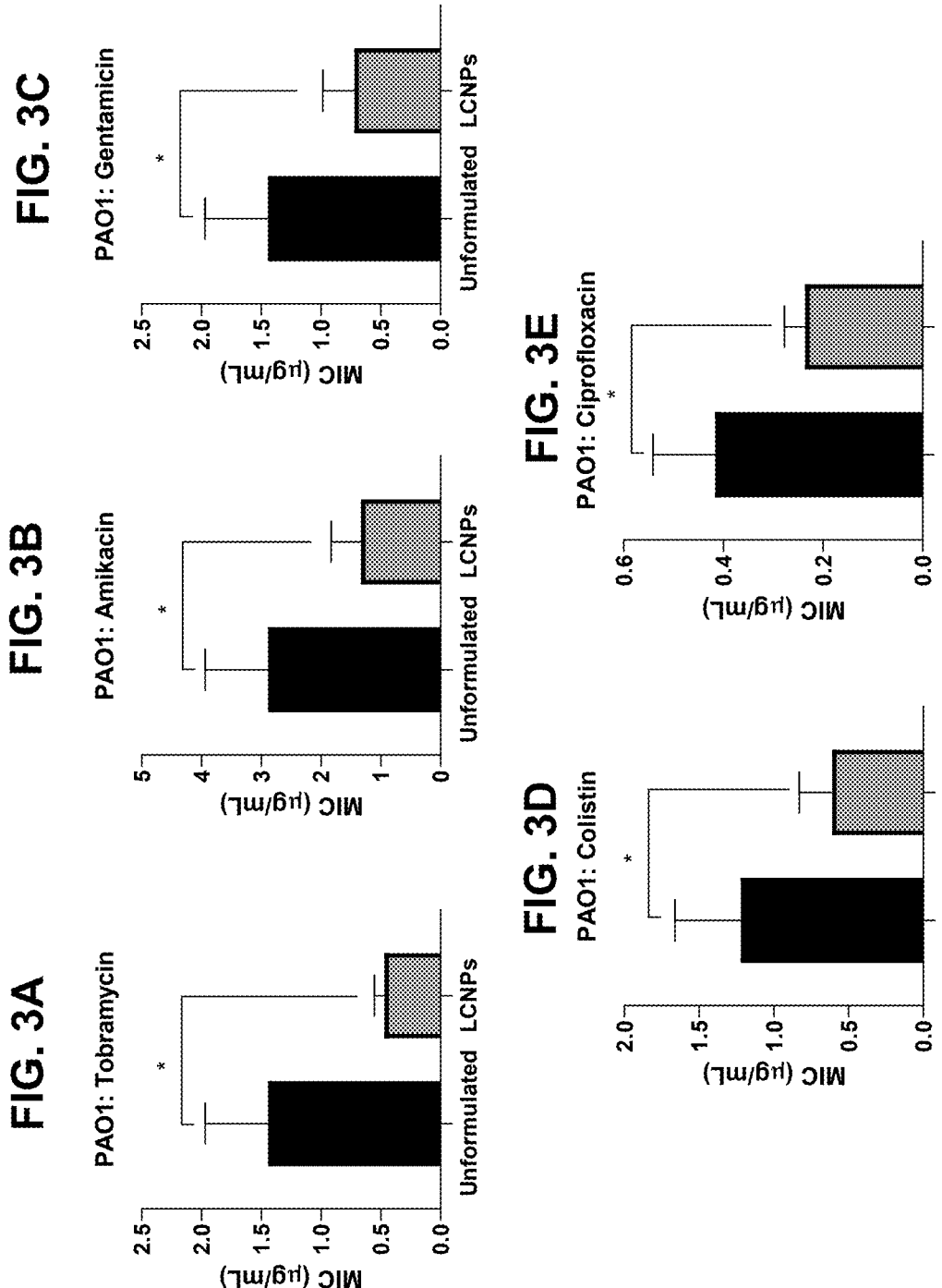

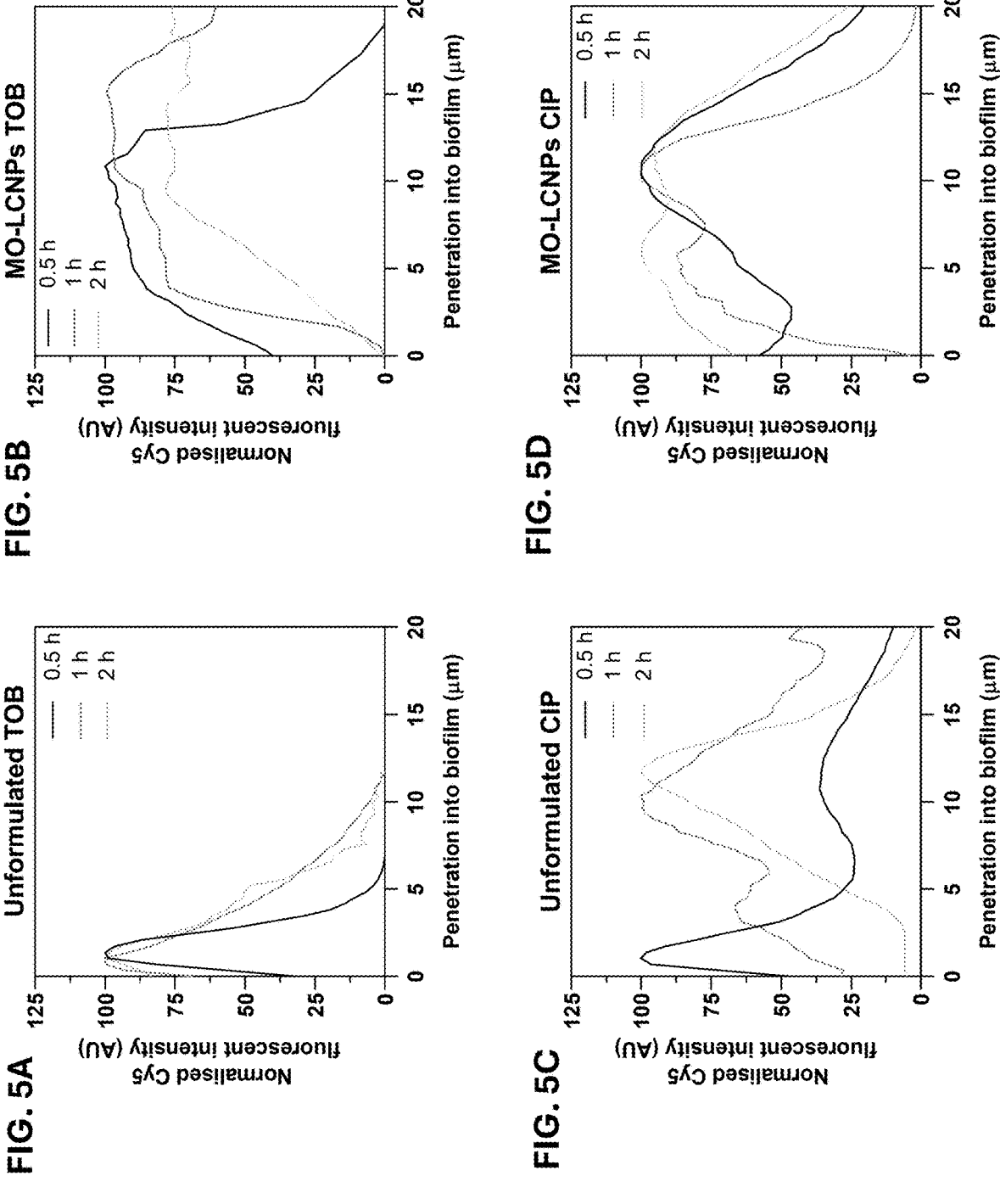

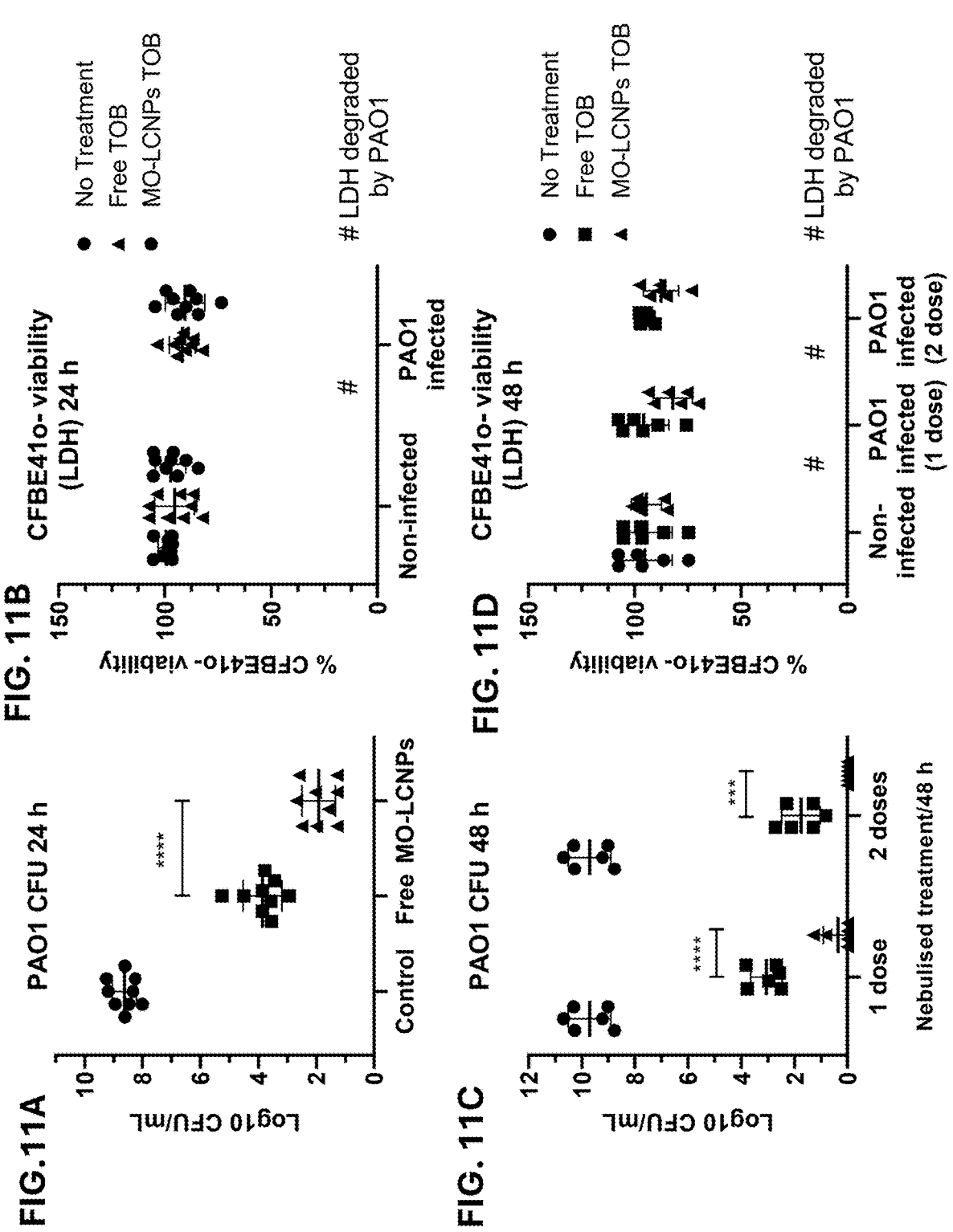

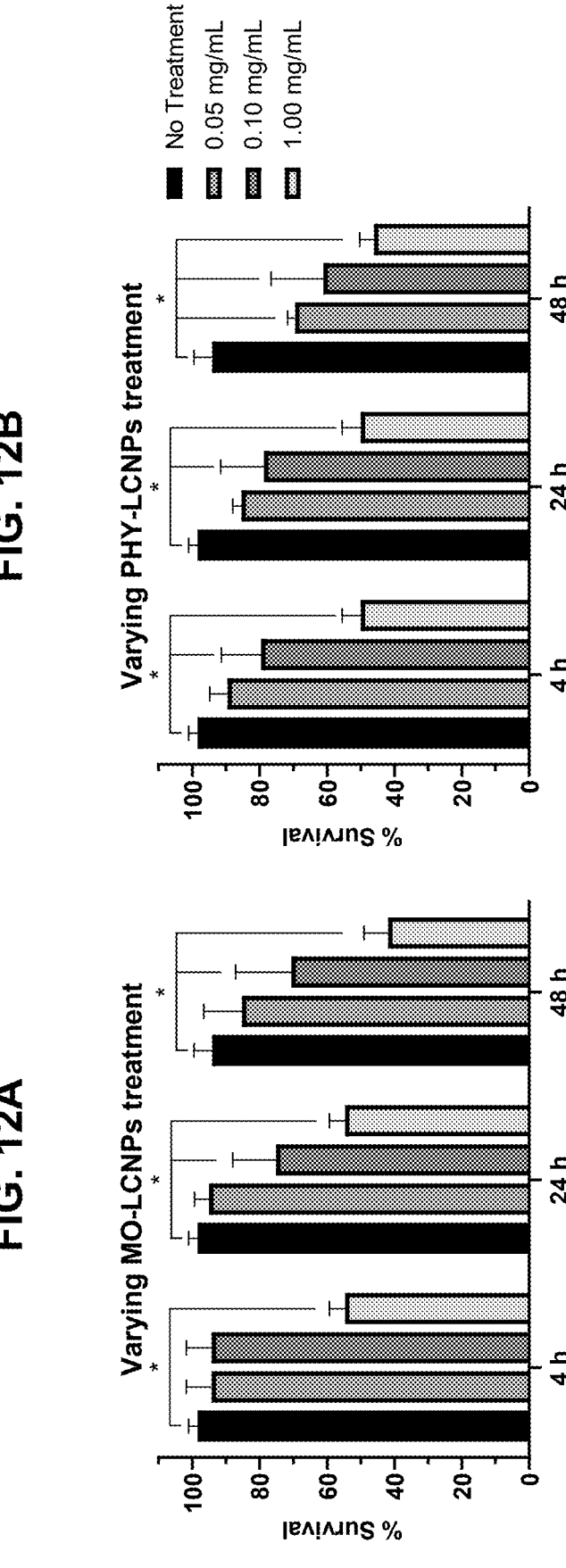

FIG. 13A

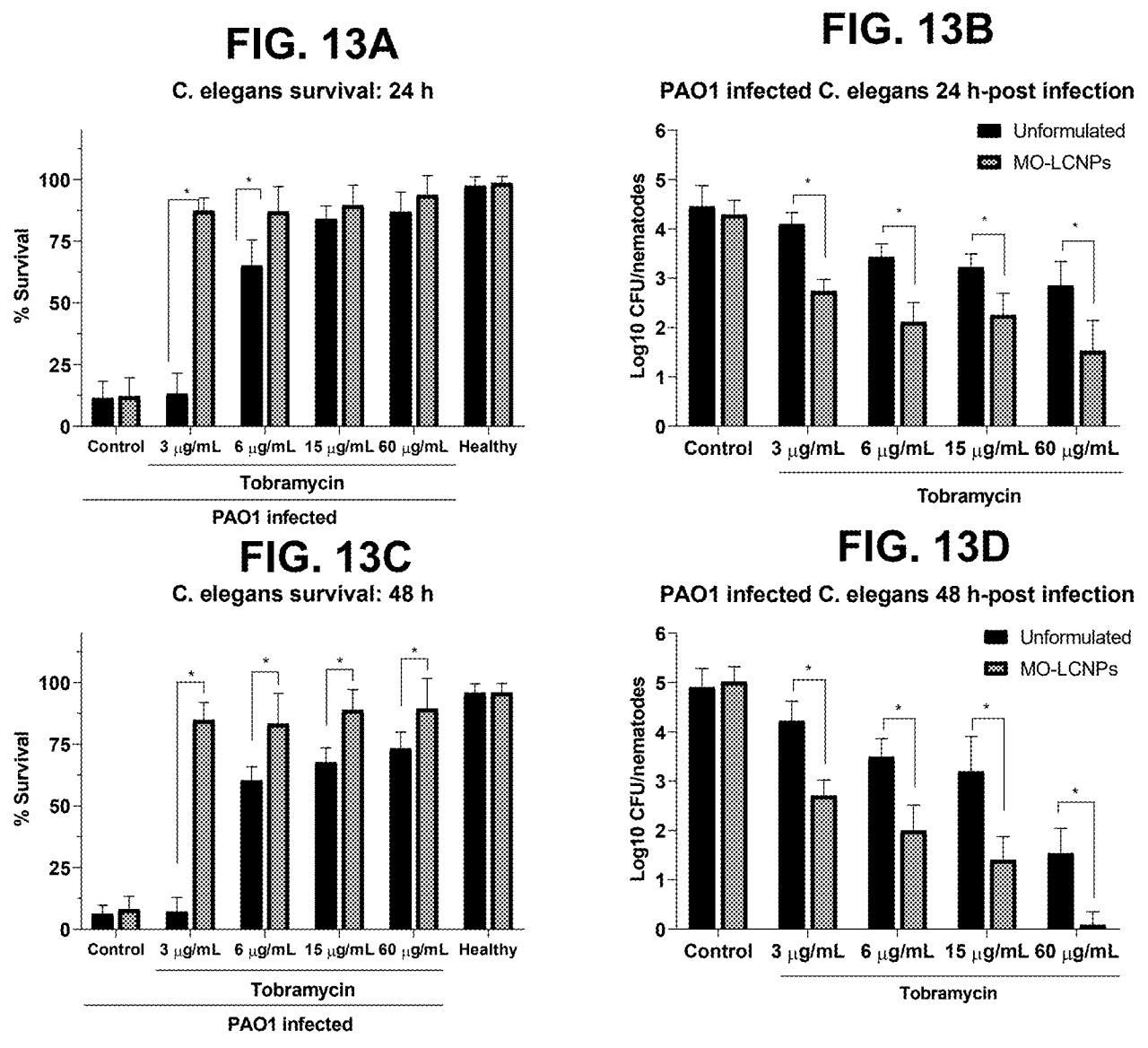

C. elegans survival: 24 h

FIG. 13B

PAO1 infected C. elegans 24 h-post infection

FIG. 13C

C. elegans survival: 48 h

FIG. 13D

PAO1 infected C. elegans 48 h-post infection

FIG. 14B          Bioluminescence PA Xen41
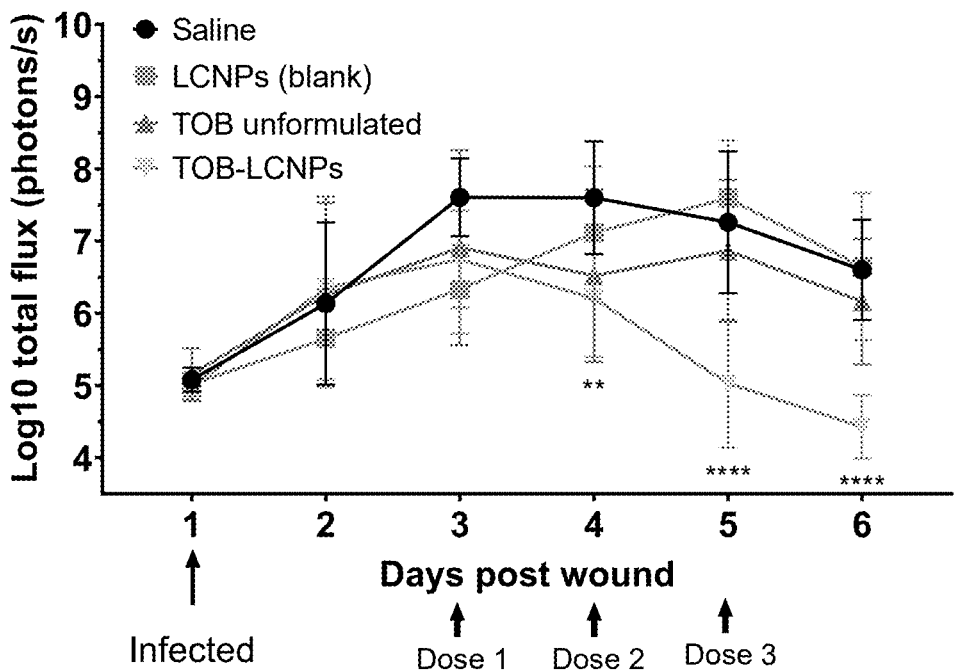
FIG. 14C          PA Xen41 CFU day 6
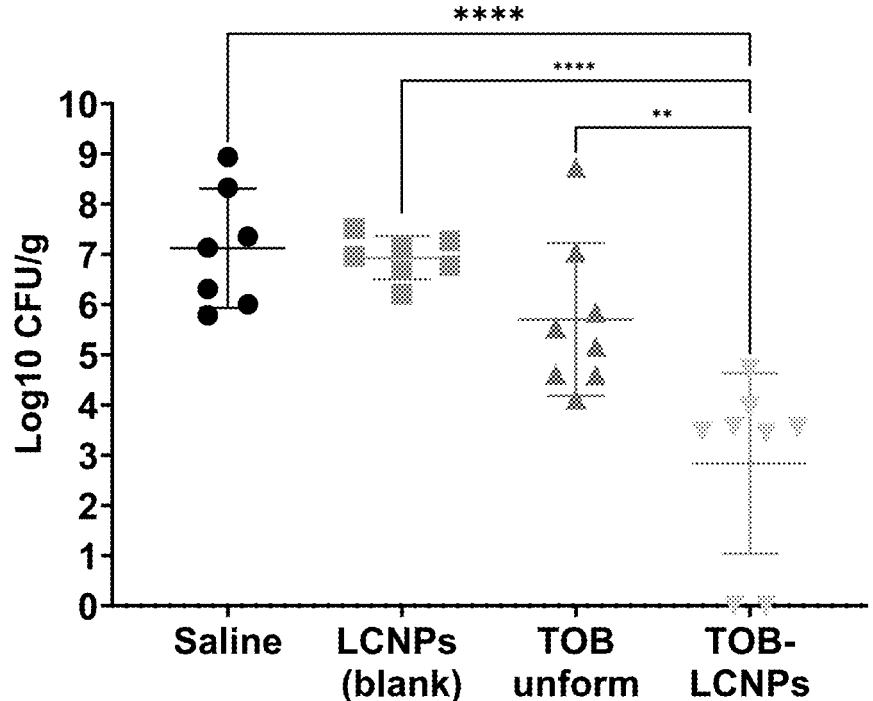

FIG. 16A
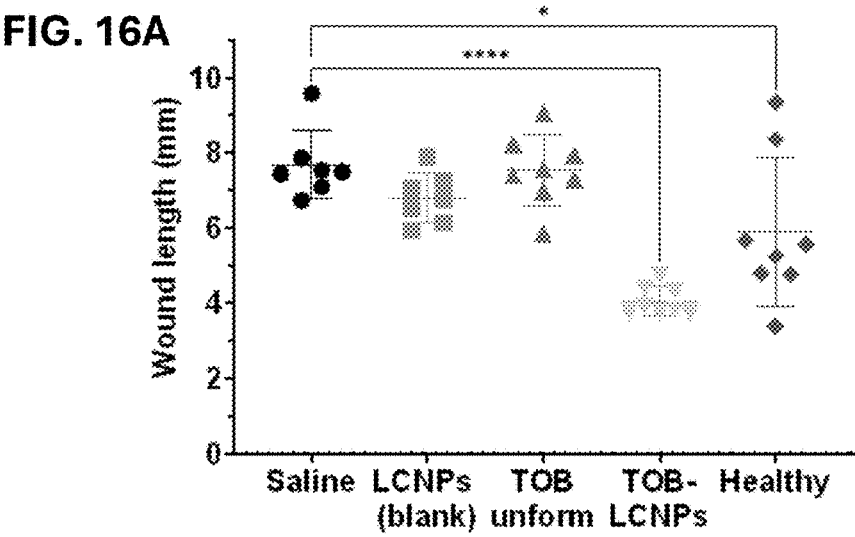
FIG. 16B
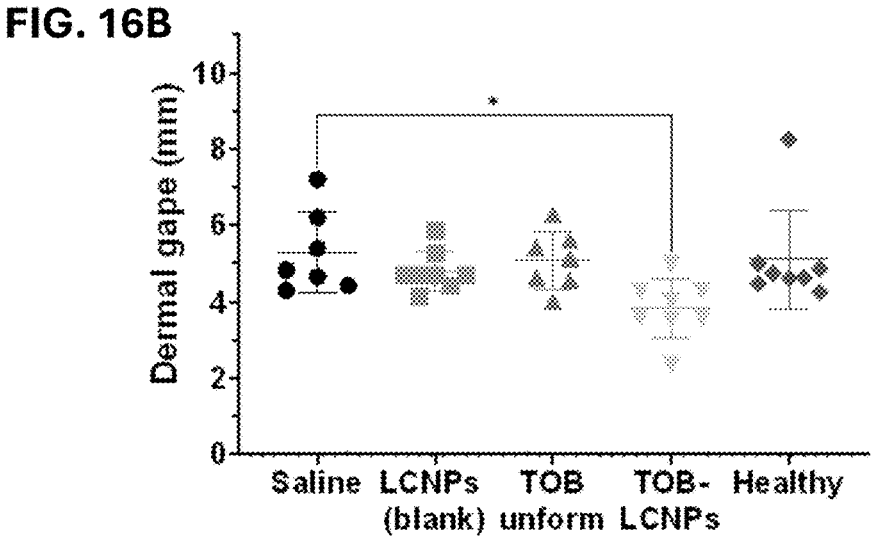
FIG. 16C

ANTIMICROBIAL COMPOSITIONS AND METHODS OF USE

PRIORITY CLAIM

This application is the § 371 U.S. National Stage of International Application No. PCT/AU2021/051195, filed Oct. 13, 2021, which was published in English under PCT Article 21(2), which in turn claims priority from Australian provisional patent application number 2020903710 filed on 13 Oct. 2020, the contents of which are to be taken as incorporated herein by this reference.

FIELD OF THE INVENTION

The present invention relates to antimicrobial compositions that have superior efficacy in treating microbial infections, including those associated with biofilms. The compositions comprise an antimicrobial agent an aminoglycoside antibiotic contained within a nanostructured liquid crystal carrier.

BACKGROUND OF THE INVENTION

An antimicrobial is an agent that kills, or inhibits the growth of, microorganisms. Antimicrobials can be classified based on the microorganism they primarily act against. For example, antibacterial such as antibiotics target bacteria, whereas antifungals are used against fungi. Since the discovery of penicillin in 1928, and its subsequent purification and development as an antibacterial agent, antibiotics have underpinned modern medicine. In fact, their use has been indispensable for the treatment of serious infections such as tuberculosis, meningitis and pneumonia, for preventing surgical site infections, and for managing immunocompromised individuals. However, the presence of bacteria in biofilms significantly reduces, and often eliminates, the ability of antibacterial agents such as antibiotics to exert their intended effect.

Biofilms are involved in numerous microbial infections in the body and can account for up to 80% of all infections. For example, biofilms have been implicated in common infectious processes such as bacterial vaginosis, urinary tract infections, catheter infections, middle-ear infections, formation of dental plaque, gingivitis, and coating contact lenses. The involvement of biofilms in less common, but more lethal processes, include endocarditis, infections in cystic fibrosis, and infections of permanent indwelling devices such as joint prostheses, catheters, heart valves, and intervertebral discs. For example, over half of the five million central venous catheters placed each year will develop a biofilm infection, despite the advances in clinical approaches. Furthermore, bacterial biofilms can impair cutaneous wound healing and reduce topical antibacterial efficiency in healing or treating infected skin wounds. Therefore, early detection of biofilms in wounds is crucial to successful chronic wound management.

Biofilms are significantly more tolerant to antimicrobials than free-floating (planktonic) bacteria. Bacteria within a biofilm are surrounded by a thick matrix of extracellular polymeric substances (EPS), including proteins, DNA, polysaccharides and lipids. The EPS protects the bacteria from the outside environment and enables a closely packed community that are in continuous communication through quorum sensing. The EPS matrix of the biofilm retards the entry of noxious substances, particularly antibiotics, which results as a protective mechanism for the bacteria, and which significantly increases the tolerance to antibiotics.

Cationic antibiotics, including tobramycin, gentamicin, amikacin, streptomycin, plazomicin, neomycin, paromomycin, colistin, vancomycin, as well as antimicrobial peptides are examples of antimicrobial agents that are unable to penetrate the EPS matrix due to electrostatic repulsion between the compounds and matrix. Currently, the only promising treatment available for biofilm infections requires the delivery of high doses of antibiotics over an extended period, or physical removal of the biofilm through surgery. However, these modalities have significant concerns including risk of high toxicity and complications to the patients.

*Pseudomonas aeruginosa* (*P. aeruginosa*) has been recognized by the World Health Organisation as one of the critical pathogens for which new antibiotics are urgently needed to ensure public health. It is an opportunistic organism and is well known for causing the life-long and life threating lung infections in cystic fibrosis. Cystic fibrosis is an inheritable disease caused by a mutation in the gene of a protein that regulates the movement of salt in and out of cells. This particularly affects the lungs, digestive system and other accessory organs of the body. All bodily products such as mucus, sweat and digestive juices are abnormally thicker, and their functions are impaired due to the mutation in the protein. The thick and stagnant mucus in the lungs promotes the desired environment for *P. aeruginosa* colonization, leading to life-long antimicrobial therapy in addition to countless other therapies employed to remove the mucus and maintain a quality of life. Currently, no effective therapy exists to eradicate *P. aeruginosa* biofilm infection in cystic fibrosis patients, and it is a big contributor to the mortality from this disease.

Besides lung infections in cystic fibrosis, *P. aeruginosa* is also involved in non-healing wound and sinus infections. In 2017, *P. aeruginosa* infections resulted in an estimated 32,600 infections in hospitalized patients and 2,700 deaths in the United States alone. As indicated above, the major issue of *P. aeruginosa* infection is the intrinsic formation of a biofilm. However, biofilm production is not limited to *P. aeruginosa* infections. Numerous different bacteria populate and thrive in biofilms, including other Gram-negative bacteria such as other species of *Pseudomonas, Eschericia coli, Klebsiella pneumoniae, Clostridium* spp, *Actinobacillus pleuropneumoniae, Legionella pneumophila, Salmonella typhi, Chlamydi* spp, *Haemophilus* spp, and *Enterococcus hirae*. Gram-positive bacteria such as *Bacillus* spp, *Listeria monocytogenes*, and *Staphylococcus* spp also populate biofilms, as do fungal pathogens such as *Candida, Aspergillus,* and *Cryptococcus*.

It is clear that biofilm infections pose a significant medical burden, are expensive to combat, and are difficult to eradicate. Therefore, there is a clear need for antimicrobial compositions that are efficacious in the treatment of microbial infections, and in particular infections associated with biofilms.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

It has been shown herein that antimicrobial agents, including antibiotics, contained within nanostructured liquid crystal carriers display an enhanced effect at treating microbial infections, including infections associated with biofilms, when compared to the use of antimicrobial agents alone.

Accordingly, in a first aspect the present invention provides an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a second aspect, the present invention provides a method for the treatment or prevention of a microbial infection in a subject, the method comprising administering to the subject an effective amount of an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In some embodiments of the first and second aspects of the invention, the nanostructured liquid crystal carrier comprises liquid crystal nanoparticles formed from a lipid in a non-lamellar liquid crystalline structure in an aqueous solvent. In some embodiments, the liquid crystal nanoparticles are formed from an amphiphilic lipid. In some embodiments, the amphiphilic lipid is selected from monoolein or phytantriol.

In some embodiments of the first and second aspects of the invention, the liquid crystal nanoparticles have a particle size of about 50 nm to about 500 nm. In some embodiments, the concentration of the amphiphilic lipid in the antimicrobial composition is about 0.01 mg/ml to about 0.5 mg/ml.

In some embodiments of the first and second aspects of the invention, the antimicrobial agent is one or more of a cationic antibiotic, antimicrobial peptide, and an antifungal agent. In some embodiments, the cationic antibiotic is an aminoglycoside antibiotic. In some embodiments, the aminoglycoside antibiotic is selected from one or more of tobramycin, amikacin, gentamicin, kanamycin, neomycin, netilmicin, paromomycin, streptomycin, plazomicin and spectinomycin. In some embodiments, the cationic antibiotic is colistin.

In some embodiments of the first and second aspects of the invention, the antimicrobial agent is contained within the nanostructured liquid crystal carrier at an equal volume to weight ratio to the lipid. In some embodiments, the concentration of the antimicrobial agent contained within the nanostructured liquid crystal carrier is up to about 6 mg/ml. In some embodiments, the concentration of the antimicrobial agent contained within the nanostructured liquid crystal carrier is up to about 25% (w/w) of the lipid.

In some embodiments of the first and second aspects of the invention, the nanostructured liquid crystal carrier potentiates the activity of the antimicrobial agent for the treatment or prevention of a microbial infection. In some embodiments, the microbial infection forms part of a biofilm in a subject. In some embodiments, the microbial infection is in a planktonic state in a subject. In some embodiments, the subject has become resistant or tolerant to the antimicrobial agent when administered in the absence of the nanostructured liquid crystal carrier.

In some embodiments of the first and second aspects of the invention, the microbial infection is a bacterial infection which is due to a Gram-negative bacterium. In some embodiments, the Gram-negative bacterium is selected from *Pseudomonas aeruginosa, Burkholderia cepacia, Klebsiella pneumoniae, Clostridium tetani, Clostridium perfringens, Clostridium botulinum, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella bumetti, Escherichia coli, Neiserria meningitidis, Neiserria gonorrhea, Haemophilus influenzae, Haemophilus ducreyi, Yersinia pestis, Yersinia enterolitica, Enterococcus hirae, Burkholderia pseudomallei, Francisella tularensis, Bacteroides fragilis, Fusobascterium nucleatum, Moraxella catarrhalis* and *Cowdria ruminantium.*

In some embodiments of the first and second aspects of the invention, the composition is in the form of a liquid, a gel, a suspension, a solid, a semi-solid, or a powder. In some embodiments, the composition is formulated for topical administration, parenteral administration, administration by inhalation, and oral administration. In some embodiments, the composition is administered by inhalation using a nebulizer or dry powder inhaler. In some embodiments, the composition is used for the treatment or prevention of a microbial infection of the pulmonary system, of soft tissue, of a wound, of sinuses, of an eye, of skin, of an ear, or of a mucosal membrane. In some embodiments, the composition is used to treat cystic fibrosis sinopulmonary infections.

In some embodiments of the first and second aspects of the invention, the antimicrobial agent is an aminoglycoside antibiotic selected from one or more of tobramycin, gentamicin, or amikacin, and the nanostructured liquid crystal carrier comprises liquid crystal nanoparticles formed from monoolein or phytantriol. In some embodiments, the aminoglycoside antibiotic is tobramycin, and the nanostructured liquid crystal carrier comprises liquid crystal nanoparticles formed from monoolein. In some embodiments, the aminoglycoside antibiotic is gentamicin, and the nanostructured liquid crystal carrier comprises liquid crystal nanoparticles formed from monoolein. In some embodiments, the aminoglycoside antibiotic is amikacin, and the nanostructured liquid crystal carrier comprises liquid crystal nanoparticles formed from monoolein. In some embodiments, the composition is used for the treatment of a *Pseudomonas aeruginosa* infection which forms part of a biofilm.

In some embodiments of the first and second aspects of the invention, the composition comprises one or more further antimicrobial agents.

In a third aspect, the present invention provides use of an antimicrobial composition in the manufacture of a medicament for the treatment or prevention of a microbial infection in a subject, wherein the composition comprises:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a fourth aspect, the present invention provides a kit for use in, or when used for, the treatment or prevention of a microbial infection in a subject, wherein the kit comprises an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a fifth aspect, the present invention provides a method of reducing the viability of a microorganism which forms part of a biofilm, the method comprising exposing the microorganism to an effective amount of an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a sixth aspect, the present invention provides a method for potentiating the activity of an antimicrobial agent in a subject, the method comprising administering to the subject an effective amount of an antimicrobial composition comprising:

(i) the antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a seventh aspect, the present invention provides use of an antimicrobial composition in the manufacture of a medicament for potentiating the activity of an antimicrobial agent in a subject, wherein the composition comprises:

(i) the antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In an eighth aspect, the present invention provides a method for reducing the dose of an antimicrobial agent required to treat or prevent a microbial infection in a subject, the method comprising administering to the subject an effective amount of an antimicrobial composition comprising:

(i) the antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a ninth aspect, the present invention provides use of an antimicrobial composition in the manufacture of a medicament for reducing the dose of an antimicrobial agent required to treat or prevent a microbial infection in a subject, wherein the composition comprises:

(i) the antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a tenth aspect, the present invention provides a method for increasing the potency of an antimicrobial agent required to treat or prevent a microbial infection in a subject, the method comprising administering to the subject an effective amount of an antimicrobial composition comprising:

(i) the antimicrobial agent; and (ii) a nanostructured liquid crystal carrier, wherein the antimicrobial agent is contained within the nanostructured liquid crystal carrier, and wherein the nanostructured liquid crystal carrier potentiates the activity of the antimicrobial agent.

In an eleventh aspect, the present invention provides use of an antimicrobial composition in the manufacture of a medicament for increasing the potency of an antimicrobial agent required to treat or prevent a microbial infection in a subject, wherein the composition comprises:

(i) the antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a twelfth aspect, the present invention provides a method for reducing viability of a microorganism resistant or tolerant to an antimicrobial agent, the method comprising exposing the microorganism to an effective amount of an antimicrobial composition comprising:

(i) the antimicrobial agent; and (ii) a nanostructured liquid crystal carrier.

wherein the aminoglycoside antibiotic is contained within the nanostructured liquid crystal carrier, and wherein the nanostructured liquid crystal carrier potentiates the activity of the antimicrobial agent.

In a thirteenth aspect, the present invention provides a method of treating an instrument, a medical device, an implant, or a surface, the method comprising exposing the instrument, medical device, implant, or surface, to an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In some embodiments of the third to thirteenth aspects of the invention, the antimicrobial agent is one or more of a cationic antibiotic, antimicrobial peptide, and an antifungal agent. In some embodiments, the cationic antibiotic is an aminoglycoside antibiotic. In some embodiments, the aminoglycoside antibiotic is selected from one or more of tobramycin, amikacin, gentamicin, kanamycin, neomycin, netilmicin, paromomycin, streptomycin, plazomicin and spectinomycin. In some embodiments, the cationic antibiotic is colistin.

In a fourteenth aspect, the present invention provides a method for the treatment or prevention of a *Pseudomonas aeruginosa* infection in a subject, the method comprising administering to the subject an effective amount of an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In a fifteenth aspect, the present invention provides a method for the treatment or prevention of a *Pseudomonas aeruginosa* infection in a subject, the method comprising administering to the subject an effective amount of an antimicrobial composition comprising:

(i) tobramycin; and (ii) a nanostructured lipid carrier comprising liquid crystal nanoparticles formed from monoolein, wherein tobramycin is contained within the liquid crystal nanoparticles.

In a sixteenth aspect, the present invention provides a method for the treatment or prevention of a *Pseudomonas aeruginosa* infection in a subject, the method comprising administering to the subject an effective amount of an antimicrobial composition comprising:

(i) gentamicin; and (ii) a nanostructured liquid crystal carrier comprising liquid crystal nanoparticles formed from monoolein, wherein gentamicin is contained within the liquid crystal nanoparticles.

In a seventeenth aspect, the present invention provides a method for the treatment or prevention of a *Pseudomonas aeruginosa* infection in a subject, the method comprising administering to the subject an effective amount of an antimicrobial composition comprising:

(i) amikacin; and (ii) a nanostructured liquid crystal carrier comprising liquid crystal nanoparticles formed from monoolein, wherein amikacin is contained within the liquid crystal nanoparticles.

BRIEF DESCRIPTION OF THE FIGURES

For a further understanding of the aspects and advantages of the present invention, reference should be made to the following detailed description, taken in conjunction with the accompanying figures which illustrate certain embodiments of the present invention.

FIG. 1—a table representing composition formation and antibiotic release characteristics of the formulations. The table shows the particle size, zeta potential, tobramycin load and release rate in 50-150 mM Tris-NaCl buffer, pH 7.4 of various LCNPs and liposomes. Data represented as mean±standard deviation, n=9.

FIG. 2—a table representing deposition efficiency characteristics of the formulations, and composition characteristics after nebulisation. The table shows the particle size and zeta potential characteristics of LCNPs after nebulisation, along with total mass of tobramycin deposited from nebulisation of 100 μL of 3.32 mg/mL using the Aerogen® Pro (vibrating mesh nebuliser)+nebulisation chamber, fitted into 24 well plate. Data represented as mean±standard deviation, n=9.

FIGS. 3A-3E—graphs demonstrating the antimicrobial activity of various antibiotics against planktonic *P. aeruginosa*. The graphs show the minimum inhibitory concentration (MIC) of various antibiotics either as an unformulated solution or loaded in MO-LCNPs, determined by standard microbroth dilution assays against PAO1 (planktonic). Data represented as mean±standard deviation, n=8 (2 independent experiments), student t test, *=P<0.01.

FIGS. 5A-5D—graphs showing the penetration of tobramycin-LCNPs and ciprofloxacin-LCNPs in *P. aeruginosa* biofilm. The graphs are obtained from representative rendered 3D laser scanning confocal microscopy z-stacks of *P. aeruginosa* (PAO1-GFP tagged) biofilm grown in flow cell for three days, at timed intervals following treatment with Cy5 tobramycin (unformulated) and octadecyl rhodamine B chloride (R18) MO-LCNPs loaded with Cy5 tobramycin, Cy5 ciprofloxacin, or R18 MO-LCNPs loaded with Cy5 ciprofloxacin. The normalised fluorescent intensities of Cy5 labelled antibiotics were extracted from each single z-stack of two independent images at three time points post treatment using image analysis software (ImageJ) to compute the intensity versus penetration into the biofilm graphs of Cy5 tobramycin as unformulated solution (A), and loaded in MO-LCNPs (B), or Cy5 ciprofloxacin as unformulated solution (C) and loaded in MO-LCNPs (D).

FIGS. 11A-11D—graphs showing the antimicrobial activity of tobramycin in a chronic lung infection model, and host cell viability after composition delivery. CFBE41o– (p 4.83, 4.85, p 4.87) 0.05×10$^6$ cells/well infected with PAO1 biofilm, following 24 h after nebulised treatment with 12 μg of unformulated tobramycin or 12 μg of MO-LCNPs (MO=0.025 mg/mL) using the Aerogen® Pro (vibrating mesh nebuliser) and nebulisation chamber. The total amount of PAO1 remaining after 24 h treatment is shown in (A). CFBE41o– viability assessed via LDH assay compared to cells treated with 5% Triton X is shown in (B). Data represented as mean±standard deviation, n=9 (3 independent experiments), one-way ANOVA with Tukey multiple comparison test **=P<0.0001. The total amount of PAO1 remaining after 1 treatment per 48 h and 2 treatments every 24 h is shown in (C). CFBE41o– viability assessed via LDH assay compared to cells treated with 5% Triton X is shown in (D). Data represented as mean±standard deviation, n=6 (2 independent experiments), two-way ANOVA with Tukey multiple comparison test **=P<0.00001

FIGS. 12A-12B—graphs showing the survival of *Caenorhabditis elegans* (*C. elegans*) following treatment with different concentrations of MO-LCNPs and PHY-LCNPs. The survival of healthy L4 stage *C. elegans* exposed to varying concentrations of unloaded MO-LCNPs (A) or unloaded PHY-LCNPs (B) for up to 48 h. Data represented as mean±standard deviation, n=6 (×40 nematodes, 2 independent experiments), * P<0.01 two-way ANOVA followed by Sidak's multiple comparison test.

FIGS. 13A-13D—graphs representing the survival and bacterial load remaining following treatment of *P. aeruginosa* infected *C. elegans* with different tobramycin-LCNPs formulations. L4 stage *C. elegans* were infected for 6 h with PAO1 (OD=0.1), then treated with tobramycin unformulated (A) or in MO-LCNPs (0.05 mg/mL) (B). *C. elegans* survival and bacterial load (CFU) 24 h post establishment of infection is shown in (C), and *C. elegans* survival and bacterial load (CFU) 48 h post establishment of infection is shown in (D). Data represented as mean±standard deviation, n=9 (×20 nematodes, 3 independent experiments), * P<0.01, two-way ANOVA followed by Sidak's multiple comparison test.

FIGS. 14A-14C—in vivo antimicrobial efficacy of tobramycin unformulated (TOB uniform) compared to tobramycin-LCNPs (TOB-LCNPs). (A) Representative bioluminescent images showing the progression of *P. aeruginosa* infection in response to different treatments. (B) Log 10 of total flux from bioluminescent imaging over the time course of the study, and (C) Log 10 CFU/g comparison between treatments from excised wounds at day 6. Data represented as mean±standard deviation, n=8 mice, =P<0.01, **=P<0.0001, assessed via two-way ANOVA followed by Dunnet's multiple comparison test for (B) and one-way ANOVA followed by Tukey's multiple comparison test for (C).

FIGS. 16A-16D—microscopic wound healing analysis via hematoxylin and eosin (H&E) histology analysis. A comparison between infected treated and non-infected wounds. (A) Wound length measured from the green line indicating wound area in (D). (B) Dermal gape measured from the red line in (D). (C) Wound re-epithelisation measured from the neo-epithelium yellow lines divide by the wound area, data represented as mean±standard deviation, *=P<0.05, *=P<0.001 and ** P<0.0001 assessed via one-way ANOVA followed by Tukey's multiple comparison test. D. representative H&E-stained cross-sections for respective treatments.

DETAILED DESCRIPTION OF THE INVENTION

Figure 4A:
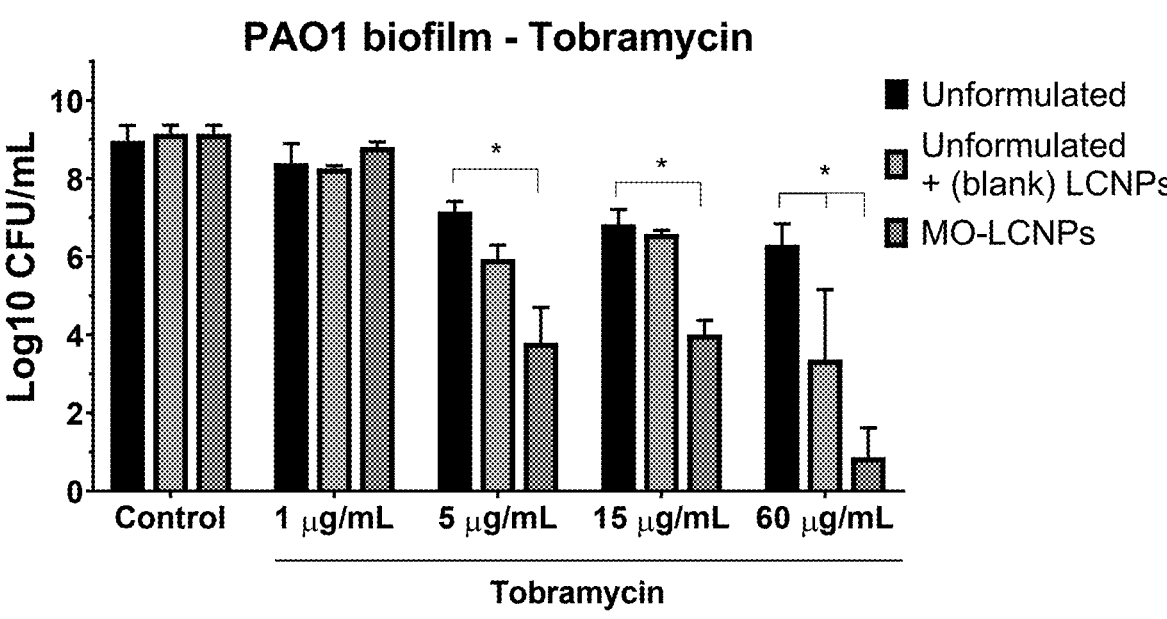
FIGS. 4A-4B—graphs showing the concentration dependent activity of tobramycin-LCNPs and ciprofloxacin-LCNPs against *P. aeruginosa* biofilms. The graphs show the total amount of PAO1 remaining after PAO1 biofilm (formed on MBEC® model) was treated with variation concentration of tobramycin (A) and ciprofloxacin (B) as an unformulated solution (black), unformulated solution combined with blank MO-LCNPs (light grey), and MO-LCNP (dark grey). The concentration of MO-LCNPs was consistently 0.25 mg/mL. Data represented as mean±standard deviation, n=6 (3 independent experiments), two-way ANOVA *=P<0.01.

The present invention is predicated, in part, on the identification of antimicrobial compositions that have superior efficacy in treating or preventing microbial infections, including those associated with biofilms. In such environments, it has been determined that the activity of antimicrobial agents can be potentiated when combined with a nanostructured liquid crystal carrier. Accordingly, amongst other applications, the present invention provides compositions and methods for treating or preventing infections, reducing the viability of a microorganism, including those which form part of a biofilm, enhancing the activity of antimicrobial agents, reducing the dose of antimicrobial agents required to treat or to prevent an infection, increasing the potency of antimicrobial agents required to treat or to prevent an infection, and treating an instrument, medical device, implant or surface.

Certain disclosed embodiments provide compositions, methods, products, and uses thereof that have one or more advantages. For example, some of the advantages of some embodiments disclosed herein include one or more of the following: new products and compositions for the treatment of infections, including microbial infections associated with a biofilm; identification of a new treatment regime for infections; identification of a treatment regime that is suitable for the treatment of microorganisms in a biofilm; identification that the activity of antimicrobial agents can be potentiated/enhanced by co-application with a nanostructured liquid crystal carrier; a treatment regime that can utilise lower concentrations of antimicrobial agents that target infections or can improve the efficacy of such agents than when used alone; a new regime for the treatment of infections caused by bacteria such as *Pseudomonas aeruginosa,* including when present in a biofilm or planktonic state; to provide one or more advantages, or to provide a commercial alternative. Other advantages of some embodiments of the present disclosure are provided herein.

It has been shown herein that antimicrobial agents, including antibiotics, contained within nanostructured liquid crystal carriers display an enhanced effect at treating microbial infections, including infections associated with biofilms, when compared to the use of antimicrobial agents alone. Surprisingly, this enhanced activity was not observed using other nanostructured carriers such as liposomes.

Accordingly, in one aspect, the present invention provides an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

As used herein the term "liquid crystal" has the conventional meaning, namely a state of matter that has properties between those of a conventional liquid and those of solid crystal. More specifically, liquid crystals are partially ordered, anisotropic fluids, which are thermodynamically located between the three-dimensional solid crystal and the flow governed liquid. They exhibit orientational or low dimensional positional order of their long molecular axis or the molecular centres of mass, respectively, which results in anisotropic physical properties, such as refractive index, viscosity, elastic constant, electric conductivity, or magnetic susceptibility, while retaining the ability to flow. There are two general classes of liquid crystals, namely thermotropic materials, which exhibit the liquid crystalline state exclusively on temperature variation, and lyotropic liquid crystals, where the formation of liquid crystal phases is achieved by concentration variation of shape anisotropic dopant materials in an isotropic carrier or host fluid. The latter type is most often composed from amphiphilic molecules in water.

In aqueous surfactant and polar lipid phases, water associates with the hydrophilic head group of a surfactant molecule (to form a "hydrophilic domain") rather than the hydrophobic tail (the "hydrophobic domain"). When surfactant molecules are placed in water they self-assemble to form geometric structures, the nature of which is dictated by the interplay between local and global constraints. For example, they may form two-dimensional lamellar structures, or hexagonal liquid crystal structures, or three-dimensional bicontinuous cubic structures. It is also known that they may convert between different phases in response to various factors including changes in temperature and dilution. For example, they may convert between inverse micelles ($L_2$), inverse hexagonal phase ($H_2$), inverse bicontinuous cubic phase ($<3/4$), lamellar phase ($L_a$), normal bicontinuous cubic phase (Qi), normal hexagonal phase (H-i) and micelles (Li). In some instances, these structures may only swell to a finite dilution enabling the dispersion of the liquid crystal into particles in excess water. In the case of lamellar, hexagonal and cubic phase, these particles have been termed liposomes, hexosomes and cubosomes, respectively. Structures of this type are disclosed for example in U.S. Pat. No. 5,531,925 (Landh et al) and International publication WO 2007/140510 (Monash University). It is to be made clear that the nanostructured liquid crystal carrier encompassed by the present invention does not include liposomes.

Instead, the nanostructured liquid crystal carrier encompassed by the present invention may in some embodiments comprise liquid crystal nanoparticles formed from a lipid in a non-lamellar liquid crystalline structure in an aqueous solvent. Specific examples include inverse hexagonal and inverse bicontinuous cubic carriers.

Many liquid crystalline systems are centred around glyceride-based lipids, monoolein (glycerol monooleate) (GMO) and monolinolein which form bicontinuous cubic structures in excess water. Many phospholipids have also been known to form liquid crystalline structures in excess water. Surfactants with a glycerate headgroup have been reported to also form liquid crystalline structures in excess water.

More recently lipids with phytanyl and farnesyl hydrophobic tails have also been identified to form liquid crystalline structures in excess water. Phytantriol (3,7,11,15-tetramethylhexadecane-1,2,3-triol) (PHYT) is a polar lipid principally known for use in cosmetics and hair-care products. For example, U.S. Pat. No. 5,834,013 (Ribier et at assigned to L'Oreal) describes the use of PHYT and a water soluble surface active agent acting as a stabiliser in dermatological or cosmetic products.

PHYT and GMO form similar liquid crystalline structures in water and exhibit similar phase change behavior, in particular both form a bicontinuous cubic structure in excess water at room temperature and both form a reverse hexagonal structure in excess water at higher temperatures. In essence, the nanostructured liquid crystal carrier for use in the present invention is a three-dimensional construct of multiple lipid bilayers, where the water channels remain exposed on the outside, unlike, for example, the single lipid bilayer of liposomes that enclose the aqueous compartment.

Methods for making the nanostructured liquid crystal carrier for use in the present invention would be known in the art. For example, exemplary methods are disclosed in Boyd B J et al., 2009, *Journal of Liposome Research* 19(1): 12-28. Various methods include: (1) Equilibrium facture (stirring liquid crystal forming lipid in stabiliser solution); (2) High energy dispersion (liquid crystal forming lipid mixed under high shear with aqueous stabiliser liquid, concentrations dependent on binary phase diagram); (3) Dilution trajectories/hydrotrope dilution method (mixing liquid crystal forming lipid with hydrotropic solvent and aqueous stabiliser solvent, according to ternary phase diagram (Spicer P T et al., 2001, *Langmuir* 17:5748-5756)); (4) Spray drying; (5) Self-assembly using catanionic surfactant systems; and (6) Formation from mixed micelles: "procubosomes" (mixed micelles comprising (i) an alkyl glycoside known to form the diamond Pn3m bicontinuous cubic phase in excess water (1-O-phytanyl-β-D-xyloside), (ii) a hydrophilic detergent (n-octyl-β-D-glucoside), and (iii) Pluronic F127 to stabilize the particles once they have formed, dialysed against water to remove the octyl glucoside (Abraham T et al., 2004, *Coll. Surf. Biointerf.*, 35: 107-717)).

In the dilution trajectories/hydrotrope dilution method, bulk liquid crystals are formed by mixing amphiphilic lipid with an aqueous solution, where the concentrations dictate the liquid crystal structure and mixing may occur with the use of heat or physical methods. The bulk liquid crystals can then be dispersed into liquid crystal nanoparticles via high energy shearing methods (i.e. sonication or homogenization) in a larger aqueous phase and the addition of a surfactant surface stabilizer, for example poly (ethylene oxide)-poly (propylene oxide)-poly (ethylene oxide)(PEO-PPO-PEO). Commercial tri-block copolymers of PEO-PPO-PEO that can also be used to stabilize the liquid crystal nanoparticles include Pluronic F-127 (also known as Poloxamer 407), Pluronic F-68, Poloxamine 908, Poloxamer 407/908 combinations, Tween 20, Tween 40, Tween 60, Tween 80, Polyethylenimine, PEG660 hydroxystearate, Glucose laurate, Albumin, and Casein. These stabilizers can be purchased from various sources such as Sigma-Aldrich (Merck KGaA, Darmstadt, Germany).

Further details on forming nanostructured liquid crystal carriers from a gel precursor of an amphiphilic lipid dissolved in a hydrotrope, for example propylene glycol, which is then hydrated in the presence of a surfactant surface stabiliser in a larger aqueous volume, can be found in the art. For example, see WO2002/066014, Drummond C J and Fong C, 1999, *Current Opinion in Colloid & Interface Science*, 4(6): 449-456; Kaasgaard T and Drummond C J, 2006, *Phys. Chem. Chem. Phys.*, 8: 4957-4975; Larsson K, 1989, *The Journal of Physical Chemistry*, 93(21): 7304-7314; Shah J C et al., 2001, *Advanced Drug Delivery Reviews* 47(2-3): 229-250; Spicer P T, 2004, Cubosomes: bicontinuous cubic liquid crystalline nanostructured particles. Encyclopedia of Nanoscience and Nanotechnology (pp 881-892), Marcel Dekker; Spicer P T, 2005, *Curr. Opin. Coll. Interf. Sci.*, 10: 274-279; Malmsten M, 2006, *Soft Matter*, 2: 760-769; and Malmsten M, 2007, *J. Disp. Sci. Tech.*, 28:63-72.

The nanostructured liquid crystal carriers for use in the present invention may be formed from an amphiphilic lipid as indicated above. An amphiphilic lipid is a compound with at least one hydrophilic head group (i.e. alcohol, carboxylic acid, amine) attached to a hydrocarbon chain providing both hydrophilic and hydrophobic chemical properties. Amphiphilic lipids spontaneously self-assemble into different structures in aqueous systems, including but not limited to; lamellar phases, inverse micelles, inverse hexagonal phase, inverse cubic phases, normal cubic phases, normal hexagonal phase and micelles. The structure of the liquid crystalline phase is dependent on the critical packing parameter of the amphiphilic lipid which is a dimensionless ratio of the hydrophobic chain volume to the product of the area of the hydrophilic head group and the hydrophobic chain length. The structure is also affected by environment factors, including; ionic strength, pH, water concentration and temperature. Amphiphilic lipids are waxy solids at room temperature and include, but are not limited to, mono-, di-glycerides, long-chain protonated fatty acids, waxes, and sterols.

Examples of different amphiphile head groups and hydrophobes that can form liquid crystal phases would be known in the art and are generally described in Boyd B J et al., 2009, supra. For example, the headgroup may be one of a glycerate, glycerol ester, glycerol ether, 3-methyl propanetriol, urea, biuret, mono-saccharide, di-saccharide, ethylene oxide and phosphatidylethanolamine (PE). Examples of a hydrophobe may be one of an unsaturated mono-acyl/alkenyl, phytanyl, farnesyl, and dialkyl (with PE headgroups).

In some embodiments the amphiphilic lipid may be selected from monoolein, phytantriol, monolaurin/glyceryl monolaurin, dioleoyl phosphatidylethanolamine, dioleyl- and dilinoleyl phosphatidylcholine, oleyl glycerate, phytanyl glycerate, and farnesyl glycerate, and Selachyl alcohol (1-O-octaclec-9-enyl glycerol, available from Nikko Chemicals, Co., Tokyo, Japan).

In some embodiments the amphiphilic lipid is monoolein. In some embodiments the amphiphilic lipid is phytantriol. Monoolein is available from commercial sources such as Sigma (St. Louis, MO, USA), Rylo MG19 from Danisco (Grinsted, Denmark) and Myverol 18-99K from Kerry Ingredients (Almere, The Netherlands). Phytantriol is available from commercial sources such as DSM Nutritional products, Singapore (formerly Roche nutritional products division), A&E Connock (Fordingbridge, Haripshire, UK), Kuraray (Tokyo, Japan) and BASF (Ludwigshafen, Germany).

In some embodiments, the liquid crystal nanoparticles of the nanostructured liquid crystal carrier have a particle size of about 50 nm to about 500 nm. For example, the liquid crystal nanoparticles have a particle size of about 50 nm to about 450 nm, about 50 nm to about 400 nm, about 50 nm to about 350 nm, about 50 nm to about 300 nm, about 50 nm to about 250 nm, about 50 nm to about 200 nm, about 50 nm to about 150 nm, about 50 nm to about 100 nm, about 100 nm to about 500 nm, about 100 nm to about 450 nm, about 100 nm to about 400 nm, about 100 nm to about 350 nm, about 100 nm to about 300 nm, about 100 nm to about 250 nm, about 100 nm to about 200 nm, about 100 nm to about 150 nm, about 150 nm to about 500 nm, about 150 nm to about 450 nm, about 150 nm to about 400 nm, about 150 nm to about 350 nm, about 150 nm to about 300 nm, about 150 nm to about 250 nm, about 150 nm to about 200 nm, about 200 nm to about 500 nm, about 200 nm to about 450 nm, about 200 nm to about 400 nm, about 200 nm to about 350 nm, about 200 nm to about 300 nm, about 200 nm to about 250 nm, about 250 nm to about 500 nm, about 250 nm to about 450 nm, about 250 nm to about 400 nm, about 250 nm to about 350 nm, about 250 nm to about 300 nm, about 300 nm to about 500 nm, about 300 nm to about 450 nm, about 300 nm to about 400 nm, about 300 nm to about 350 nm, about 350 nm to about 500 nm, about 350 nm to about 450 nm, about 350 nm to about 400 nm, about 400 nm to about 500 nm, about 400 nm to about 450 nm, and about 450 nm to about 500 nm. Other ranges are contemplated.

In some embodiments, the concentration of the amphiphilic lipid forming the liquid crystal nanoparticles is up to about 10% (w/v) in an aqueous system. For example, the concentration of the amphiphilic lipid forming the liquid crystal nanoparticles is up to about 9.5% (w/v), up to about 9.0% (w/v), up to about 8.5% (w/v), up to about 8.0% (w/v), up to about 7.5% (w/v), up to about 7.0% (w/v), up to about 6.5% (w/v), up to about 6.0% (w/v), up to about 5.5% (w/v), up to about 5.0% (w/v), up to about 4.5% (w/v), up to about 4.0% (w/v), up to about 3.5% (w/v), up to about 3.0% (w/v), up to about 2.5% (w/v), or up to about 2.0% (w/v), in an aqueous system. Other amounts are contemplated with the ultimate amount dictated by the lipid used. However, it is to be made clear that the amount of amphiphilic lipid in the aqueous system is proportional to the phase diagram to form the reversed bicontinuous cubic or reversed hexagonal phase.

In some embodiments, the concentration of the amphiphilic lipid in the antimicrobial composition is about 0.01 mg/ml to about 0.5 mg/ml. For example, the concentration of the amphiphilic lipid in the antimicrobial composition is about 0.01 mg/ml to about 0.4 mg/ml, about 0.01 mg/ml to about 0.3 mg/ml, about 0.01 mg/ml to about 0.2 mg/ml, about 0.01 mg/ml to about 0.1 mg/ml, about 0.01 mg/ml to about 0.05 mg/ml, about 0.05 mg/ml to about 0.5 mg/ml, about 0.05 mg/ml to about 0.4 mg/ml, about 0.05 mg/ml to about 0.3 mg/ml, about 0.05 mg/ml to about 0.2 mg/ml, about 0.05 mg/ml to about 0.1 mg/ml, about 0.1 mg/ml to about 0.5 mg/ml, about 0.1 mg/ml to about 0.4 mg/ml, about 0.1 mg/ml to about 0.3 mg/ml, about 0.1 mg/ml to about 0.2 mg/ml, about 0.2 mg/ml to about 0.5 mg/ml, about 0.2 mg/ml to about 0.4 mg/ml, about 0.2 mg/ml to about 0.3 mg/ml, about 0.3 mg/ml to about 0.5 mg/ml, about 0.3 mg/ml to about 0.4 mg/ml, and about 0.4 mg/ml to about 0.5 mg/ml. Other ranges are contemplated.

As indicated above, the antimicrobial composition of the present invention comprises an antimicrobial agent. In some embodiments, the antimicrobial agent is selected from one or more of a cationic antibiotic, an antimicrobial peptide, and an antifungal agent.

Cationic antibiotics contain a positive charge and are therefore hindered in their effectiveness against microbial biofilms or hindered in their entry into microbial cells. Cationic antibiotics for use in the composition of the present invention may be selected from the group consisting of a protein synthesis inhibitor, a cell wall synthesis inhibitor or cell membrane disruptor including beta-lactam antibiotics, beta-lactamase inhibitors and peptidoglycan synthesis inhibitors, a lipopeptide, a DNA synthesis inhibitor, a RNA synthesis inhibitor, a mycolic acid synthesis inhibitor, a mechanosensitive channel of large conductance (MscL), and a folic acid synthesis inhibitor, or a combination of the aforementioned antibiotics. Cationic antibiotics for use in the present invention can be purchased from relevant commercial suppliers such as Sigma-Aldrich (Castle Hill, NSW, Australia), ChemSupply (Adelaide, SA, Australia), Glentham Life Sciences (Corsham, England, UK), and Cayman Chemicals, and methods for their use are known in the art, for example as described in "Therapeutic Guidelines—Antibiotic", Version 15, 2014, published by eTG complete.

Examples of protein synthesis inhibitors include those which stop or slow the growth or proliferation of cells by inhibiting the processes that lead to protein production. Such protein synthesis inhibitors typically (but not always) act by disrupting the activity of the ribosome during translation of mRNA. Examples of antibiotics which are classed as protein synthesis inhibitors would be known to those skilled in the art. Specific examples include, but are not limited to, aminoglycosides such as amikacin, gentamicin, kanamycin, neomycin, netilmicin, tobramycin, paromomycin, streptomycin and spectinomycin), and lincosamides such as clindamycin and lincomycin.

Examples of cell wall synthesis inhibitors or cell membrane disruptors include, but are not limited to, carbapenems, colistin, and glycopeptides such as teicoplanin, vancomycin, telavancin, dalbavancin and oritavancin. Other inhibitors of this class would be known to those skilled in the art.

Examples of DNA and RNA synthesis inhibitors, and folic acid synthesis inhibitors, would be known to those skilled in the art.

Mechanosensitive channels of large conductance (MscL) consists of pore-forming membrane proteins that are responsible for translating physical forces applied to cell membranes into electrophysiological activities. MscL have a relatively large conductance, 3 nS, making them permeable to ions, water, and small proteins when opened. Examples of MscL can be found at http://www.tcdb.orgisearch/result.php?tc=1.A.22.3.

In some embodiments, the cationic antibiotic for use in the composition of the present invention comprises an aminoglycoside, also referred to herein as an aminoglycoside. Am inoglycosides are natural or semisynthetic antibiotics derived from actinomycetes. They share a core structure of amino acid sugars connected via glycosidic linkages to a dibasic aminocyclitol, which is most commonly 2-deoxystreptamine. Aminoglycosides are broadly classified into four subclasses based on the identity of the aminocyclitol moiety: (1) no deoxystreptamine (but rather having a streptidine ring); (2) a mono-substituted deoxystreptamine ring; (3) a 4,5-di-substituted deoxystreptamine ring; or (4) a 4,6-di-substituted deoxystreptamine ring. The core structure is decorated with a variety of amino and hydroxyl substitutions that have a direct influence on the mechanisms of action and susceptibility to various aminoglycoside-modifying enzymes (AMEs) associated with each of the aminoglycosides.

The aminoglycosides primarily act by binding to the aminoacyl site of 16S ribosomal RNA within the 30S ribosomal subunit, leading to misreading of the genetic code and inhibition of translocation. The initial steps required for peptide synthesis, such as binding of mRNA and the association of the 50S ribosomal subunit, are uninterrupted, but elongation fails to occur due to disruption of the mechanisms for ensuring translational accuracy. The ensuing antimicrobial activity is usually bactericidal against susceptible aerobic gram-negative bacilli.

The most common clinical application (either alone or as part of combination therapy) of the aminoglycosides is for the treatment of serious infections caused by aerobic gram-negative bacilli. While less common, aminoglycosides (in combination with other agents) have also been used for the treatment of select gram-positive infections. In addition, certain aminoglycosides have demonstrated clinically relevant activity against protozoa, Neisseria gonorrhoeae, and mycobacterial infections.

In some embodiments, the aminoglycoside antibiotic is selected from one or more of tobramycin, amikacin, gentamicin, kanamycin, neomycin, netilmicin, paromomycin, streptomycin, plazomicin, and spectinomycin. Sources of these, and other, aminoglycoside antibiotics would be known to a person skilled in the art. For example, they could be purchased commercially from companies including, but not limited to, Merck KGaA (Darmstadt, Germany), Tokyo Chemical Industry (TCI, Tokyo, Japan), BOC Sciences (New York, United States of America), and Tocris Bioscience (Bristol, United Kingdom).

In some embodiments, the antimicrobial agent is an antimicrobial peptide. The term "antimicrobial peptide" as used herein refers to a peptide that can kill or inhibit growth of a microorganism. The antimicrobial peptide may be a naturally occurring peptide, or may be artificially produced. Naturally occurring antimicrobial peptides are evolutionarily conserved molecules found in organisms ranging from prokaryotes to humans. The antimicrobial peptides encompassed herein are those which are classed as cationic, meaning they carry an overall positive charge. Antimicrobial peptides are also referred to as cationic peptide antibiotics.

Cationic antimicrobial peptides generally consist of between 10 and around 50 amino acid residues. These peptides frequently contain a distribution of basic amino acids and hydrophobic residues that align in three dimensions on opposing faces, therefore forming unique structures that are water soluble, positively charged and hydrophobic. Folded cationic antimicrobial peptides can be classified into groups based on their secondary structure, namely α-helical, β-sheet, and extended antimicrobial peptides. Amphipathic α-helical antimicrobial peptides include the frog magainin, and the human cathelicidin peptide LL37. These peptides exhibit little secondary structure in aqueous solution but adopt the amphipathic α-helical architecture when they enter a non-polar environment, such as the bacterial membrane. Other antimicrobial peptides, such as bactenecins and defensins, are characterized by two or more β-sheets that are stabilized by disulfide bonds. Lastly, the extended antimicrobial peptides are peptides that do not possess a specific structural motif but rather are defined by a high content of specific residues, such as histidine, arginine, glycine or tryptophan. For example, histatins from humans are rich in histidine residues, and indolicidin from bovine leukocytes has multiple tryptophan and arginine residues.

More than 2,500 antimicrobial peptides have been identified in single-celled organisms, plants, insects and animals, and a number of them have been used as therapeutic agents in humans. These include the clinical use of: bacitracin for pneumonia; boceprevir for hepatitis C; and dalbavancin, daptomycin, orativancin, teiavancin and vancomycin for bacterial infections.

In some embodiments, the antimicrobial agent is an antifungal agent. An "antifungal" as used herein means a biocidal compound that can inhibit the growth of, or kill, fungi or fungal spores. In some embodiments, the antifungal may be selected from one or more of a polyene, an azole, an allylamine, and an echinocandin.

A polyene is a molecule with multiple conjugated double bonds. A polyene antifungal is a macrocyclic polyene with a heavily hydroxylated region on the ring opposite the conjugated system. This makes polyene antifungals amphiphilic. Polyene antimycotics bind with sterols in the fungal cell membrane, principally ergosterol. This changes the transition temperature of the cell membrane, thereby placing the membrane in a less fluid, more crystalline state. As a result, the contents of the fungal cell leak and result in cell death.

In some embodiments, the polyene antifungal is selected from one or more of amphotericin B, candicidin, filipin, hamycin, natamycin, nystatin and rimocidin.

An azole antifungal can inhibit the enzyme lanosterol 14 α-demethylase, which is necessary to convert lanosterol to ergosterol. Depletion of ergosterol in fungal membrane disrupts the structure and many functions of the membrane ultimately leading to inhibition of fungal arowth.

In some embodiments, the azole antifungal is selected from an imidazole, a triazole, and/or a thiazole. For example, the imidazole may be selected from bifonazole, butoconazole, clotrimazole, econazole, fenticonazole, isoconazole, ketoconazole, iuliconazole, miconazole, omoconazole, oxiconazole, sertaconazole, sulconazole and tioconazole. The triazole may be selected from albaconazole, efinaconazole, epoxyconazole, fluconazole, isavuconazole, itraconazole, posaconazole, propiconazole, ravuconazole, terconazole and voriconazole. The thiazole may include abafungin.

An allylamine can inhibit squalene epoxidase, which is another enzyme required for ergosterol synthesis in the fungal membrane. In some embodiments, the allylamine antifungal may be selected from amorolfin, butenafine, naftifine, and terbinafine.

An echinocandin inhibits the synthesis of glucan in the cell wall via the enzyme 1,3-Beta-glucan synthase. In some embodiments, the echinocandin antifungal may be selected from anidulafungin, caspofungin and micafungin.

The antifungal for use in the composition of the present invention may also be selected from the group consisting of an aurone, benzoic acid, ciclopirox, flucytosine, griseofulvin, haloprogin, tolnaflate, undecylenic acid, crystal violet and Balsam of Peru.

Examples of fungal infections for which the composition of the present invention may be used include infections associated with a fungal species such as *Aspergillus, Alternaria, Aureobasidium, Candida, Cladosporium, Cryptococcus, Curvularia, Coniophora, Diplodia, Epidermophyton, Engodontium, Fusarium, Gliocladium, Gloeophylium, Humicola, Histoplasma, Lecythophora, Lentinus, Malassezia, Memnionella, Mucor, Oligoporus, Paecilomyces, Penicillium, Petriella, Paracoccidioides, Phanerochaete, Phoma, Pneumocystis, Poria, Pythium, Rhodotorula, Rhizopus, Schizophyllum, Sclerophoma, Scopulariopsis, Serpula, Sporobolomyces, Stachybotrys, Stemphylium, Trichosporon, Trichtophyton, Trichurus,* and *Ulocladium.* Other types of fungi are contemplated.

In some embodiments, the infection may be due to a fungal skin or mucosal infection. In some embodiments, the fungal infection is due to *Candida albicans.*

As indicated above, the antimicrobial agent is contained within the nanostructured liquid crystal carrier, meaning that when the agent is combined with the carrier (i.e. loaded onto the carrier), the agent populates the interior of the liquid crystal structure of the carrier. The antimicrobial agent may be contained within the nanostructured liquid crystal carrier via a passive loading process such as that described in Thorn C R et al., 2020, *Journal of Controlled Release,* 319: 168-182. The agent can be dissolved in the aqueous channels of the liquid crystals such that it is trapped within the liquid crystal structure via a physical or chemical interaction. The agent may also be situated within the lipid portion of the liquid crystals.

In some embodiments, the antimicrobial agent is contained within the nanostructured liquid crystal carrier at an equal volume to weight ratio to the lipid.

In some embodiments, the antimicrobial agent is contained within the nanostructured liquid crystal carrier at a concentration of up to about 6.0 mg/mL. For example, the concentration of the antimicrobial agent contained within the nanostructured liquid crystal carrier may be up to about 5.8 mg/ml, up to about 5.6 mg/ml, up to about 5.4 mg/ml, up to about 5.2 mg/ml, up to about 5.0 mg/ml, up to about 4.8 mg/ml, up to about 4.6 mg/ml, up to about 4.4 mg/ml, up to about 4.2 mg/ml, up to about 4.0 mg/ml, up to about 3.8 mg/ml, up to about 3.6 mg/ml, up to about 3.4 mg/ml, up to about 3.2 mg/ml, up to about 3.0 mg/ml, up to about 2.8 mg/ml, up to about 2.6 mg/ml, up to about 2.4 mg/ml, up to about 2.2 mg/ml, up to about 2.0 mg/ml, up to about 1.8 mg/ml, up to about 1.6 mg/ml, up to about 1.4 mg/ml, up to about 1.2 mg/ml, or up to about 1.0 mg/ml. Other amounts are contemplated with the ultimate amount dictated by the antimicrobial agent used.

In some embodiments, the concentration of the antimicrobial agent contained within the nanostructured liquid crystal carrier is up to about 25.0% (w/w) of the lipid. For example, the concentration of the antimicrobial agent contained within the nanostructured liquid crystal carrier is up to about 24.5% (w/w), up to about 24.0% (w/w), up to about 23.5% (w/w), up to about 23.0% (w/w), up to about 22.5% (w/w), up to about 22.0% (w/w), up to about 19.5% (w/w), up to about 19.0% (w/w), up to about 18.5% (w/w), up to about 18.0% (w/w), up to about 17.5% (w/w), up to about 17.0% (w/w), up to about 16.5% (w/w), up to about 16.0% (w/w), up to about 15.5% (w/w), up to about 15.0% (w/w), up to about 14.5% (w/w), up to about 14.0% (w/w), up to about 13.5% (w/w), up to about 13.0% (w/w), up to about 12.5% (w/w), up to about 12.0% (w/w), up to about 11.5% (w/w), up to about 11.0% (w/w), up to about 10.5% (w/w), up to about 10.0% (w/w), up to about 9.5% (w/w), up to about 9.0% (w/w), up to 8.5% (w/w), up to about 8.0% (w/w), up to about 7.5% (w/w), up to about 7.0% (w/w), up to about 6.5% (w/w), up to about 6.0% (w/w), up to about 5.5% (w/w), or up to about 5.0% (w/w) of the lipid. Other amounts are contemplated with the ultimate amount dictated by the antimicrobial agent and lipid used.

As indicated above, the inventors have surprisingly found that antimicrobial agents, such as aminoglycoside antibiotics, contained within nanostructured liquid crystal carriers display an enhanced effect at treating or preventing microbial infections, including those infections present in a biofilm or planktonic state, when compared to the use of the antimicrobial agent alone. That is, when the antimicrobial agent in not contained with the nanostructured liquid crystal carrier, the effect of the antimicrobial agent is not enhanced.

Therefore, in such microbial infectionenvironments, the activity of antimicrobial agents is potentiated when combined with a nanostructured liquid crystal carrier. As used herein, to "potentiate" the activity should be taken to mean to increase the activity of the antimicrobial agent to a level which is greater than the activity of the antimicrobial agent when used in the absence of the nanostructured liquid crystal carrier. In other words, the nanostructured liquid crystal carrier and antimicrobial agent are acting synergistically. The activity of the antimicrobial agent may be increased by at least 1%, 5%, 10%, 20%, 30%, 40%, 50%, 60%, 70%, 80%, 90%, 100%, or greater, or by 1-fold, 2-fold, 3-fold, 4-fold, 5-fold, 6.0-fold, 7-fold, 8-fold, 9-fold, 10-fold, 15-fold, 20-fold, 25-fold, 30-fold, 35-fold, 40-fold, 45-fold, 50-fold, 60-fold, 70-fold, 80-fold, 90-fold, 100-fold, 125- fold, 150-fold, 175-fold, 200-fold, 225-fold, 250-fold, 275-fold, 300-fold, 400-fold, 500-fold, 1000-fold, 10,000-fold, 100,000-fold, or greater, when compared to the activity of the antimicrobial agent when used in the absence of the nanostructured liquid crystal carrier.

Methods for measuring the activity of the antimicrobial agent would be well known in the art. For example, the activity may be reflective of the measured minimum inhibitory concentration (MIC), minimum bactericidal concentration (MBC), and/or minimum biofilm inhibitory concentration (MBIC) of the antimicrobial agent, or of the short-kill assay times with respect to an in vitro analysis. For example, the combination of the nanostructured liquid crystal carrier and antimicrobial agent may decrease the MIC, MBC, and/or MBIC of the antimicrobial agent, or reduce the short-kill time for bacteria which are resistant or tolerant to the antimicrobial agent when administered in the absence of the nanostructured liquid crystal carrier. The activity may also be observed in the form of an improvement of the condition of the subject, for example, as determined by a clinician.

Methods for determination of MICs, MBCs and MBICs would be well known in the art. The MIC is defined as the lowest concentration of an antimicrobial agent that is bacteriostatic (i.e. prevents the visible growth of bacteria). MICs are used to evaluate the antimicrobial efficacy of a compound by measuring the effect of decreasing concentrations of the compound over a defined period in terms of inhibition of microbial population growth. For example, the MIC can be determined by the broth microdilution method as described in Wiegand I et al., 2008, *Nature Protocols*, 3(2): 163-175; and (CLSI), C.a.L.S.I., Methods for dilution antimicrobial susceptibility tests for bacteria that grow aerobically, 2012, Wayne, PA, USA. MIC values for various antibiotics and bacteria can also be obtained from the Antimicrobial Index at http://antibiotics.toku-e.com.

The MBC is the lowest concentration of an antibacterial agent required to kill a bacterium over a fixed period, such as 18 hours or 24 hours, under a specific set of conditions. It can be determined from the broth dilution of MIC tests by subculturing to agar plates that do not contain the test agent. The MBC is identified by determining the lowest concentration of antimicrobial agent that reduces the viability of the initial bacterial inoculum by a pre-determined reduction such as 99.9%. The MBC is complementary to the MIC; whereas the MIC test demonstrates the lowest level of antimicrobial agent that greatly inhibits growth, the MBC demonstrates the lowest level of antimicrobial agent resulting in microbial death. In other words, if a MIC shows inhibition, plating the bacteria onto agar might still result in organism proliferation because the antimicrobial did not cause death. The MBC can be determined by methods such as those found in CLSI M26-A, Methods for Determining Bactericidal Activity of Antimicrobial Agents, 1999, volume 19, number 18 https://clsi.org/media/1462/m26a_sample.pdf.

The MBIC is the lowest concentration of an antimicrobial agent required to inhibit the formation of biofilm. It can be measured using a number of assays such as microplate-based assays as described in Stepanovic S et al., 2007, *Acta. Path. Micro. Im.* A., 13: 891-899. Models of biofilms may also be employed to test the MBIC (for example see Macià MD et al., 2014, *Clin. Microbial. Infection,* 20(10): 981-990). Biofilm growth models have been classified as closed systems (batch culture) and open systems (continuous culture) (McBain A J, 2009, "Chapter 4: in vitro biofilm models: an overview". *Adv. Appl. Microbiol.,* 2009; 69:

99-132). Closed models have the advantage of simplicity and applicability in high-throughput analysis, whereas open models allow better control of growth parameters and dynamics (Lourenço A et al., 2014, *Pathog. Dis.,* 70: 250-256).

Examples of closed systems for measuring MBIC include the microtitre plate method. The microtitre plate (e.g. 96-well plate) filled with sterile broth culture (depending on the type of microorganism) is inoculated with bacteria and incubated for 24 to 48 h with an appropriate atmosphere and temperature. Biofilm formation takes place as a ring around the well. After rinsing of wells to remove planktonic cells, the biofilm can be stained with crystal violet and dissolved in acetone-ethanol for quantification of the biomass by measuring the optical density (Christensen G D et al., 1985, *J. Clin. Microbiol.,* 22: 996-1006). The main advantages are the ease, rapidity and reproducibility of the method.

The Calgary biofilm device (also known as the MBEC® device) is another example of a closed system for measuring MBIC. This device is a disposable 96-well microtitre plate with a lid that incorporates the same number of removable polystyrene pegs (Ceri H et al., 1999, *J. Clin. Microbiol.,* 37: 1771-1776). The bacteria are inoculated in the microtitre wells with broth culture, and the plate is incubated with or without (Mulet X et al., 2009, *Antimicrob. Agents. Chemother.,* 53: 1552-1560) shaking to allow cells to attach to pegs. The biofilm is formed around the pegs, while planktonic bacteria remain in the broth. To facilitate the growth of bacteria, the pegs can be coated with a substance, such as L-lysine or hydroxyapatite.

Open systems for measuring MBIC try to replicate the in vivo conditions through the control of nutrient delivery, flow, and temperature. Moreover, these systems make possible the implementation of pharmacokinetic/pharmacodynamic (PK/PD) models, as well as allowing observation by microscopy. Another advantage is the study of biofilm dynamics in the absence of planktonic cells (eliminated by flow). Examples of open systems for measuring MBIC include the flow cell system which has been demonstrated to be the best approach for modelling biofilm formation, as real-time non-destructive confocal laser scanning microscopy (CLSM) analyses can be performed (Klausen M et al., 2003, *Mol. Microbiol.,* 48: 1511-1524). The system includes a vessel with sterile broth culture that provides medium through a multi-channel peristaltic pump. The bacteria are directly inoculated into the flow cells by injection through silicone tubing. Cells are attached to a surface, where biofilm starts to develop. The most common attachment surfaces used are transparent and non-fluorescent microscope coverslips, in order to allow biofilm evolution to be observed. Another advantage is that a defined constant environment is provided by laminar flow (Palmer R J Jr., 1999, *Methods Enzymol.,* 310: 160-166). In addition, biofilms formed in this model are thicker than those obtained with the Calgary biofilm device.

The suspended substratum reactor (CDC Biofilm Reactor) is another example of an open system for measuring MBIC. This system consists of a glass reactor connected to a flask with sterile broth culture, which is pumped through the system. Eight coupon holders, each one housing three coupons (diameter, 12.7 mm; surface area, 2.53 cm2), are suspended from a lid placed into the reactor filled with growth medium. The bacteria are inoculated into the reactor, and the biofilm is formed upon coupons while the broth is mixed with a stirring vane by magnetic rotation. Owing to the rotation, the biofilm grows under high-shear conditions. Coupons can be sampled by removing individual coupon holders and replacing them in the lid to continue the experiment in aseptic conditions. These coupons can be made from a large number of materials (polycarbonate, mild steel, stainless steel, PVC, vinyl, glass, etc), according to the microorganism and assay. The conditions of the experiments can be controlled by modifying the flow speed, temperature, and residence times. This method allows the study of seeding planktonic cells by sampling the bulk fluid phase.

In some embodiments, the MIC, MBC or MBIC for the aminoglycoside antibiotic may be reduced by at least 10%, 20%, 30%, 40%, 50%, 60%, 70%, 80%, 90%, 100%, or greater, or by 10-fold, 20-fold, 30-fold, 40-fold, 50-fold, 60-fold, 70-fold, 80-fold, 90-fold, 100-fold, 200-fold, 300-fold, 400-fold, 500-fold, or greater, when administered with the nanostructured liquid crystal carrier. Other amounts are contemplated.

In some embodiments, the microbial infection is a bacterial infection which is due to a Gram-negative bacterium. Gram-negative bacteria are classified by the pink color they turn following crystal violet (Gram) staining. Gram-negative bacteria are enclosed in a protective capsule which prevents white blood cells from ingesting the bacteria. Under the capsule, Gram-negative bacteria have an outer membrane that protects them against certain antibiotics, such as penicillin. When disrupted, this membrane releases toxic substances called endotoxins which contribute to the severity of symptoms during infections with gram-negative bacteria. Gram-negative bacteria are resistant to multiple drugs and are increasingly resistant to most available antibiotics. When present in biofilms, Gram-negative bacteria become tolerant to available treatments, including antibiotics.

In the context of the present invention, a Gram-negative bacterium includes those which form part of a biofilm. In some embodiments, the Gram-negative bacterium is selected from *Pseudomonas aeruginosa, Burkholderia cepacia, Klebsiella pneumoniae, Clostridium tetani, Clostridium perfringens, Clostridium botulinum, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella bumetti, Escherichia coli, Neiserria meningitidis, Neiserria gonorrhea, Haemophilus influenzae, Haemophilus ducreyi, Yersinia pestis, Yersinia enterolitica, Enterococcus hirae, Burkholderia pseudomallei, Francisella tularensis, Bacteroides fragilis, Fusobascterium nucleatum, Moraxella catarrhalis* and *Cowdria ruminantium.*

The present invention is not limited to Gram-negative bacteria. Therefore, the microbial infection may be a bacterial infection which is due to a Gram-positive bacterium, a Gram test non-responsive bacterium, an aerobic bacterium, or an anaerobic bacterium, provided the bacterium forms part of a biofilm. Such bacteria are known in the art.

As indicated above, bacterial infections resident in a biofilm are extremely difficult to treat. A biofilm is a cluster of bacterial cells, irreversibly attached to a surface and embedded in a matrix of extracellular polymeric substances self-produced by the bacteria. Clinically relevant biofilms are often microbial complex structures associated with severe and recalcitrant diseases, including chronic wounds, cystic fibrosis, and chronic rhinosinusitis. *Staphylococcus aureus* represents one of the most notorious bacteria causing invasive, superficial, chronic and nosocomial (including methicillin resistant *S. aureus*) infections.

The biofilm state is advantageous for bacterial survival as the biofilm acts like a protective shield, enabling the bacteria to adapt to hostile environmental conditions, evade the immune system, and ultimately to establish resistance against antibacterial agents. Indeed, bacteria residing in biofilms can require up to 1000-fold higher concentrations of an antibacterial agent for their treatment than their planktonic (free-floating) counterparts. Therefore, bacterial biofilms represent one of the biggest challenges the medical community is facing. Indeed, recent data suggest that biofilms may account for over 80% of microbial infections in the body.

Examples of bacterial infections associated with biofilms include bacterial biofilms associated with lung infections (e.g. *P. aeruginosa,* such as occurs in patients with cystic fibrosis), urinary tract infections (e.g. *E. coli, Pseudomonas aeruginosa, Enterococci, Klebsiella, Enterobacter* spp *Proteus, Serratia*), such as being responsible for persistent infections causing relapses and acute prostatitis, wounds including acute or chronic wounds (e.g. *S. aureus, P. aeruginosa*), chronic osteomyelitis (e.g. *S. aureus*), rhinosinusitis (e.g. *S. aureus*), tuberculosis (e.g. *M. tuberculosis*) and infections associated with foreign bodies inserted in the body (e.g. *S. aureus*).

In some embodiments, the bacterial infection comprises an infected wound. Examples of wounds include acute wounds (such as those caused by abrasions, cuts and more serious penetrative injuries, burns, abscesses, nerve damage and wounds resulting from elective surgery), chronic wounds (such as diabetic, venous and decubitus ulceration) or wounds in individuals with compromised wound healing capacity, such as the elderly. In some embodiments, the bacterial infection comprises a post-surgery infected wound, for example an infected wound following abdominal surgery or sinus surgery.

Methods for assessing bacterial infection are known in the art. For example, bacterial infection in a wound would delay healing of the wound. As such various wound healing assays commonly known in the art could be utilised to test for assessing bacterial infection associated with wounds and healing thereof. One such assay is the scratch wound assay where a "wound gap" in a cell monolayer (such as a fibroblast or keratinocyte monolayer) is created by scratching, and the "healing" of this gap by cell migration and growth towards the centre of the gap is monitored and often quantified. Factors such as bacterial infection can alter the motility and/or growth of the cells which leads to a decreased rate of "healing" of the gap. An exemplary scratch wound assay can be found in Chen Y, 2012, *Bio-protocol* 2(5): e100. Other commonly used wound assays can be found in Kopecki W et al., 2017, *Wound Practice and Research,* 25(1): 6-13.

The antimicrobial composition of the present invention is formulated for administration to a subject or object to be treated. This means that the composition can take a number of physical forms depending on the nature of the use of the composition and required mode of administration. In this regard, one route of administration may include topical administration and therefore the composition may be in the form of a liquid, gel, suspension, paste, lotion, cream, solid, semi-solid, powder, and the like. Another route of administration may be systemic administration and therefore the composition may be in the form of an injectable solution, may be in a form suitable for oral administration such as a tablet, pill, capsule, or may be in another dosage form useful for systemic administration of agents. The composition may also be in the form of an aerosol, nebulizer or dry powder for inhalation delivery. Other forms of administration may include delivery by way of a scaffold, such as a biomaterial scaffold including a scaffold produced from collagen, hydroxyapatite, β-tricalcium phosphate or a combination thereof. Other routes of administration are contemplated.

The composition may be administered alone or may be delivered in the form of a suitable pharmaceutical composition, for example in a mixture with other therapeutic substances and/or other substances that enhance, stabilise or maintain the activity of the components of the composition. In some embodiments, an administration vehicle (e.g., liquid, gel, paste, powder, cream, pill, tablet, capsule, injectable solution, aerosol, etc) would contain the composition and/or additional substance(s). In this regard, the pharmaceutical composition may also include the use of one or more pharmaceutically acceptable carriers or additives, including pharmaceutically acceptable salts, amino acids, polypeptides, polymers, solvents, buffers, excipients and bulking agents, taking into consideration the particular physical and chemical characteristics of the composition to be administered.

In some embodiments, the carrier may be chosen based on various considerations including the route of administration, the antimicrobial agent being delivered and the time course of delivery of the composition. The term "pharmaceutically acceptable carrier" refers to a substantially inert solid, semi-solid or liquid filler, diluent, excipient, encapsulating material or formulation auxiliary of any type. An example of a pharmaceutically acceptable carrier is physiological saline. Other physiologically acceptable carriers and their formulations are known in the art. Some examples of materials which can serve as pharmaceutically acceptable carriers include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminium hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present.

The preparation of such pharmaceutical compositions is known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa, which are incorporated herein by reference in their entirety.

In some embodiments, the antimicrobial composition is formulated for administration by direct introduction to the respiratory system (e.g. the lungs), such as by inhalation administration via aerosol, nebulizer, or dry powder, or by being instilled into the lung. In some embodiments, it may be desirable to administer the composition directly to the airways in the form of a dry powder, since high doses of medication can be delivered over shorter periods of time compared to that of a nebuliser without the associated risks of nebuliser induced damage to the antimicrobial composition ultrastructure and/or long-term stability issues from liquid storage. In order to develop an inhalable dry powder formulation, spray-drying, lyophilisation and milling techniques can be used to produce micron-sized powders.

In some embodiments, the composition may be formulated for topical administration, e.g. transdermal administration. Transdermal administrations are understood to include all administrations across the surface of the body and the inner linings of bodily passages including epithelial and mucosal tissues. Such administrations may be carried out using the composition of the present invention as described herein, in the form of a liquid, gel, paste, lotion, cream, ointment, powder, foam, patch, suspension, solution, and a suppository (rectal and vaginal), or other suitable form.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are mono-, di-, and tri-glycerides of fatty acids or fatty alcohols with soaps, alkyl sulphates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste contains a large proportion (20-50%) of dispersed solids in a fatty or aqueous vehicle.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension semisolid dosage form for external application to the skin, which contains a gelling agent in quantities sufficient to impart a three-dimensional, cross-linked matrix. A gel is usually hydrophilic and contains sufficient quantities of a gelling agent such as starch, cellulose derivatives, carbomers, magnesium-aluminum silicates, xanthan gum, colloidal silica, aluminium or zinc soaps.

The antimicrobial composition of the present invention, when in a form for topical administration, may further include drying agents, anti-foaming agents, buffers, neutralizing agents, agents to adjust pH, colouring agents and decolouring agents, emollients, emulsifying agents, emulsion stabilizers and viscosity builders, humectants, odorants, preservatives, antioxidants, and chemical stabilizers, solvents, and thickening, stiffening, and suspending agents, and a balance of water or solvent.

Transdermal administration may also be accomplished through the use of a transdermal patch containing the active components of the composition and a carrier that is inert to the active components, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Transdermal formulations are known in art and may be formulated by a skilled person.

As indicated above, in some embodiments the antimicrobial composition of the present invention may be formulated for administration by way of a suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In some embodiments, the antimicrobial composition of the present invention may be formulated for parenteral administration. The term "parenteral" as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable, form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

The antimicrobial composition of the present invention may also be formulated using controlled release technology. For example, the composition may be administered as a sustained-release pharmaceutical. To further increase the sustained release effect, the composition may be formulated with additional components such as vegetable oil (for example soybean oil, sesame oil, camellia oil, castor oil, peanut oil, rape seed oil); middle fatty acid triglycerides; fatty acid esters such as ethyl oleate; glycerol monooleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the antimicrobial composition of the present invention may be incorporated into a hydrophobic polymer matrix, scaffold or support (such as a biodegradable matrix or support), including for controlled release of the composition over a period of days. Methods for delivering agent(s) via scaffolds are known in the art. For example, a biomaterial scaffold including a scaffold produced from collagen, hydroxyapatite, $\beta$-tricalcium phosphate or a combination thereof may be used to deliver the agent. Methods for incorporating agent(s) into such substrates are known in the art.

The antimicrobial composition may also be moulded into a solid implant, or externally applied patch, suitable for providing efficacious concentrations of the composition over a prolonged period of time without the need for frequent re-dosing. Such controlled release films are well known in the art. Other examples of polymers commonly employed for this purpose that may be used include nondegradable ethylene-vinyl acetate copolymer or degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time release characteristics and release kinetics. The composition may then be moulded into a solid implant suitable for providing efficacious concentrations of the composition over a prolonged period of time without the need for frequent re-dosing. The composition can be incorporated into the biodegradable polymer or polymer mixture in any suitable manner known to one of skill in the art and may form a homogeneous matrix with the biodegradable polymer, or may be encapsulated in some way within the polymer, or may be moulded into a solid implant.

As indicated above, the present invention is predicated on the determination that the activity of antimicrobial agents, such as aminoglycoside antibiotics, can be potentiated when combined with a nanostructured liquid crystal carrier. Accordingly, amongst other applications, the antimicrobial composition of the present invention may be used to treat or prevent a microbial infection in a subject.

Therefore, in a further aspect, the present invention provides a method for the treatment or prevention of a microbial infection in a subject, the method comprising administering to the subject an effective amount of an antimicrobial composition comprising:

(i) an antimicrobial agent; and
(ii) a nanostructured liquid crystal carrier.
wherein the antimicrobial agentis contained within the nanostructured liquid crystal carrier, and wherein the nanostructured liquid crystal carrier potentiates the activity of the antimicrobial agent.

The terms "treat", "treating" or "treatment," as used herein are to be understood to include within their scope obtaining a desired pharmacologic and/or physiologic effect in terms of improving the condition of the subject. This may be measured by one or more of the following non-limiting outcomes: (i) inhibiting to some extent the growth of a microorganism which is causing the infection in the subject, including, slowing down or complete growth arrest of the microorganism; (ii) inhibiting to some extent the growth and/or formation of one or more secondary microorganism infections in the subject; (iii) improving the life expectancy of the subject as compared to the untreated state; (iv) improving the quality of life of the subject as compared to the untreated state; (v) alleviating, abating, arresting, suppressing, relieving, ameliorating, and/or slowing the progression of at least one symptom caused by the microorganism infection in the subject; (vi) a partial or complete stabilization of the subject; (vii) a regression of one or more symptoms in the subject; (viii) a cure of a disease, condition or state in the subject.

The terms "prevent", "preventing" and "prevention" as used herein are to be understood to include within their scope obtaining a desired pharmacologic and/or physiologic effect in terms of arresting or suppressing the appearance of one or more symptoms in the subject. For example, inhibiting the formation of a microorganism infection in the subject. In some embodiments, the composition may be formulated so as to be administered to the respiratory system to prevent microorganism infections which may develop in the lungs of susceptible subjects (such as cystic fibrosis sufferers). The composition may be formulated so as to be applied to skin which has suffered a wound (for example a cut or abrasion), such that the composition acts to prevent microorganism infection in the cut or abrasion. Suitable formulations have been described above and include inhalation formulations (such as aerosols or dry powders), and topical formulations such as creams, ointments, gels, and the like.

In some embodiments, the subject will be resistant or tolerant to the antimicrobial agent when the agent is administered in the absence of the nanostructured liquid crystal carrier. A subject can be considered resistant or tolerant to an antimicrobial agent when either the agent fails to treat or prevent a microorganism infection in the subject when administered in doses which have been considered safe, or when doses outside of those considered safe need to be administered to the subject to achieve the desired outcome.

As used herein, the term "subject" should be taken to encompass any subject which would benefit from administration of the antimicrobial composition of the present invention. In some embodiments, the subject is a human or animal subject. The animal subject may be a mammal, a primate, a livestock animal (e.g. a horse, a cow, a sheep, a pig, or a goat), a companion animal (e.g. a dog, a cat), a laboratory test animal (e.g. a mouse, a rat, a guinea pig, a bird), an animal of veterinary significance, or an animal of economic significance.

In recognition that the activity of antimicrobial agent, including aminoglycoside antibiotics, can be potentiated when combined with a nanostructured liquid crystal carrier, a composition comprising these two components can be used for other purposes such as reducing the viability of a microorganism which forms part of a biofilm, enhancing the activity of an antimicrobial agent in a subject, potentiating the activity of an antimicrobial agent in a subject, reducing the dose of an antimicrobial agent required to treat or prevent an infection in a subject, increasing the potency of an antimicrobial agent required to treat or prevent an infection in a subject, or reducing viability of a microorganism resistant or tolerant to an antimicrobial agent. Other uses are contemplated.

The aforementioned methods require administering to the subject an effective amount of an antimicrobial composition comprising an antimicrobial agent, and a nanostructured liquid crystal carrier, wherein the antimicrobial agent is contained within the nanostructured liquid crystal carrier. Suitable nanostructured liquid crystal carriers and antimicrobial agents have already been described above, as too have the types of microorganisms causing infections that may be prevented or treated.

The term "effective amount" as used herein is the quantity of the antimicrobial composition which, when administered to a subject, improves the prognosis and/or health state of the subject with respect to their infection status. The amount of composition to be administered to a subject will depend on the particular characteristics of one or more of the level or amount of resistance or tolerance to the antimicrobial agent in the subject, the type of infection being inhibited, prevented or treated, the mode of administration of the composition, and the characteristics of the subject, such as general health, other diseases, age, sex, genotype, and body weight. A person skilled in the art will be able to determine appropriate dosages depending on these and other factors. The effective amount of the antimicrobial composition to be used in the various embodiments of the present invention is not particularly limited.

In some embodiments of the aforementioned methods, the antimicrobial agent is administered to the subject (as part of the composition) so as to expose the microorganism causing the infection in the subject to a concentration of the agent in the range from 0.1 µg/ml to 1,000 µg/ml, 1 µg/ml to 1,000 µg/ml, 10 µg/ml to 1,000 µg/ml, 100 µg/ml to 1,000 µg/ml, 500 µg/ml to 1,000 µg/ml, 0.1 µg/ml to 500 µg/ml, 1 µg/ml to 500 µg/ml, 10 µg/ml to 500 µg/ml, 100 µg/ml to 500 µg/ml, 0.1 µg/ml to 250 µg/ml, 1 µg/ml to 250 µg/ml, 10 µg/ml to 250 µg/ml, 100 µg/ml to 250 µg/ml, 0.1 µg/ml to 100 µg/ml, 1 µg/ml to 100 µg/ml, or 10 µg/ml to 100 µg/ml. Other ranges are contemplated with the ultimate amount dictated by the antimicrobial agent used.

In some embodiments of the aforementioned methods, the antimicrobial agent is administered to the subject (as part of the composition) in an amount ranging from one of the following selected ranges: 1 µg/kg to 1000 mg/kg; 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 1000 mg/kg; 10 µg/kg to 100 mg/kg; 10 µg/kg to 10 mg/kg; 10 µg/kg to 1 mg/kg; 10 µg/kg to 100 µg/kg; 100 µg/kg to 1000 mg/kg; 100 µg/kg to 100 mg/kg; 100 µg/kg to 10 mg/kg; 100 µg/kg to 1 mg/kg; 1 mg/kg to 1000 mg/kg; 1 mg/kg to 100 mg/kg; 1 mg/kg to 10 mg/kg; 10 mg/kg to 1000 mg/kg; 10 mg/kg to 100 mg/kg; and 100 mg/kg to 1000 mg/kg body weight of the subject. The dose and frequency of administration may be determined by one of skill in the art.

In some embodiments, the antimicrobial composition is used for the treatment of a microbial infection of the pulmonary system, of soft tissue, of a wound, of sinuses, of an eye, of skin, of an ear, or of a mucosal membrane. For example, for the treatment of cystic fibrosis sinopulmonary infections which are due to an infection caused by *Pseudomonas aeruginosa* which forms part of a biofilm in the lung of a cystic fibrosis sufferer.

Therefore, in a further aspect, the present invention provides a method for the treatment or prevention of a *Pseudomonas aeruginosa* infection in a subject, the method comprising administering to the subject an effective amount of an antimicrobial composition comprising:

(i) an antimicrobial agent; and (ii) a nanostructured liquid crystal carrier.

wherein the antimicrobial agent is contained within the nanostructured liquid crystal carrier, and wherein the nanostructured liquid crystal carrier potentiates the activity of the antimicrobial agent.

In some embodiments of this and other aspects of the invention, the antimicrobial agent is a cationic antibiotic. In some embodiments, the cationic antibody is an aminoglycoside antibiotic. In some embodiments, the antibiotic is tobramycin, and the nanostructured liquid crystal carrier comprises liquid crystal nanoparticles formed from monoolein.

In some embodiments of this and other aspects of the invention, the antimicrobial agent is a cationic antibiotic. In some embodiments, the cationic antibody is an aminoglycoside antibiotic. In some embodiments, the antibiotic is gentamicin, and the nanostructured liquid crystal carrier comprises liquid crystal nanoparticles formed from monoolein.

In some embodiments of this and other aspects of the invention, the antimicrobial agent is a cationic antibiotic. In some embodiments, the cationic antibody is an aminoglycoside antibiotic. In some embodiments, the antibiotic is amikacin, and the nanostructured liquid crystal carrier comprises liquid crystal nanoparticles formed from monoolein.

In some embodiments of this and other aspects of the invention, the antimicrobial agent is a cationic antibiotic. In some embodiments, the cationic antibody is colistin, and the nanostructured liquid crystal carrier comprises liquid crystal nanoparticles formed from monoolein.

Therefore, in a further aspect, the present invention provides a method for the treatment or prevention of a *Pseudomonas aeruginosa* infection in a subject, the method comprising administering to the subject an effective amount of an antimicrobial composition comprising:

(i) tobramycin; and (ii) a nanostructured lipid carrier comprising liquid crystal nanoparticles formed from monoolein, wherein tobramycin is contained within the liquid crystal nanoparticles.

In a still further aspect, the present invention provides a method for the treatment or prevention of a *Pseudomonas aeruginosa* infection in a subject, the method comprising administering to the subject an effective amount of an antimicrobial composition comprising:

(i) gentamicin; and (ii) a nanostructured liquid crystal carrier comprising liquid crystal nanoparticles formed from monoolein, wherein gentamicin is contained within the liquid crystal nanoparticles.

In yet a further aspect, the present invention provides a method for the treatment or prevention of a *Pseudomonas aeruginosa* infection in a subject, the method comprising administering to the subject an effective amount of an antimicrobial composition comprising:

(i) amikacin; and (ii) a nanostructured liquid crystal carrier comprising liquid crystal nanoparticles formed from monoolein, wherein amikacin is contained within the liquid crystal nanoparticles.

In some instances, the microorganism causing, or potentially causing, an infection is present in a non-biological setting, such as being present in/on a device, a system, a container, a fluid, a surface, or a site. For example, the aforementioned methods may be used to treat a medical device (such as an implant) or instrumentation, a surface, or to treat a water storage container or water pipes.

In some embodiments, the microorganism may be present in or on an instrument, a medical device or an implant (which is potentially contaminated with a microorganism, such as a bacterium) for use in a subject and as such may need to be treated prior to use, so as to eliminate the microorganism and/or to reduce the likelihood of the subject becoming infected with the microorganism. Examples of instruments, medical devices or implants include, but are not limited to, catheters, intravenous catheters, vascular prosthesis, cerebrospinal fluid shunts, prosthetic heart valves, urinary catheters, joint prostheses and orthopaedic fixation devices, cardiac pacemakers, peritoneal dialysis catheters, intrauterine devices, biliary tract stents, dentures, breast implants, and contact lenses. Such instruments, medical devices or implants may, for example, be treated with an antimicrobial composition comprising the antimicrobial agent contained within a nanostructured liquid crystal carrier.

Furthermore, surfaces which may be, or are, contaminated with a microorganism can be treated with a composition of the present invention to reduce or eliminate the microorganism thereby preventing subsequent transmission to a subject. Accordingly, such a composition may be in the form a liquid which can be sprayed onto the surface to be treated. Other formulations are contemplated as described above. As used herein, a "surface" encompasses any surface which may be exposed to the air and therefore exposed to a microorganism. Exemplary surfaces are those found in domestic settings, laboratory settings, hospitals, nursing homes, schools, childcare centres, and the like.

Accordingly, in a further aspect the present invention provides a method of treating an instrument, a medical device, an implant, or a surface, the method comprising exposing the instrument, medical device, implant, or surface, to an antimicrobial composition comprising an antimicrobial agent, and a nanostructured liquid crystal carrier, wherein the antimicrobial agent is contained within the nanostructured liquid crystal carrier, and wherein the nanostructured liquid crystal carrier potentiates the activity of the antimicrobial agent.

In some embodiments, the microorganism is present in a biological setting. In some embodiments, the microorganism is present in vitro in a biological setting.

In some embodiments, the microorganism is present in a biological system. The term "biological system" refers to a cellular system and includes one or more cells in vivo, ex vivo, in vitro; a tissue or organ in vivo or ex vivo, or an entire subject. In certain embodiments, the biological system comprises one or more cells in vitro, one or more cells in culture, one or more cells ex vivo, a tissue or organ, or a human or animal subject.

In some embodiments, the microorganism is present in vivo. In some embodiments, a subject is infected with the microorganism.

In some embodiments, the aforementioned methods are used to reduce the viability of one or more microorganisms. In some embodiments, the methods are used to kill one or more microorganisms.

In some embodiments, the methods reduce the viability of the microorganisms by 50% or more, by 60% or more, by 70% or more, by 80% or more, by 90% or more, by 95% or more, by 99% or more, by 99.9% or more, by 99.99% or more, or by 99.999% or more. In some embodiments, the methods comprise reducing the viability of the microorganism by 10 fold or more, by 100 fold or more, by 1000 fold or more, by $10^4$ fold or more, by $10^5$ fold or more, by $10^6$ fold or more, by $10^7$ fold or more, by $10^8$ fold or more, or by $10^9$ fold or more. Other levels of reduction of viability are contemplated.

In some embodiments, the methods substantially kill all the microorganisms. In some embodiments, the methods reduce the viability of microorganisms to below detectable levels. In some embodiments, the methods reduce the viability of microorganisms to below a clinically relevant level.

The term "exposing", and related terms such as "expose" and "exposure", as used herein refers to directly and/or indirectly contacting and/or treating a microorganism with an antimicrobial composition as described herein.

For a microorganism in vitro, the microorganism may, for example, be exposed to the antimicrobial composition directly, such as via a liquid composition. For a microorganism ex vivo, the microorganism may for example be exposed to the antimicrobial composition directly or indirectly, such as a tissue or organ being perfused with the composition. For a microorganism in vivo, the microorganism may for example be exposed to the antimicrobial composition directly or indirectly, such as via inhalation or via topical application, directly to a site of infection.

In a further aspect, the present invention provides a kit for use in, or when used for, the treatment or prevention of a microbial infection in a subject. The kit comprises an antimicrobial composition comprising an antimicrobial agent and a nanostructured liquid crystal carrier, wherein the antimicrobial agent is contained within the nanostructured liquid crystal carrier, and wherein the nanostructured liquid crystal carrier potentiates the activity of the antimicrobial agent. Suitable nanostructured liquid crystal carriers, antimicrobial agents and exemplary microorganisms that cause infection are described above.

In some embodiments, the nanostructured liquid crystal carrier and antimicrobial agent are provided as separate components of the kit, and the kit includes instructions for mixing the components in defined amounts prior to treating or preventing the infection. In some embodiments, the nanostructured liquid crystal carrier and antimicrobial agent are provided already combined as a single composition. In this instance, the kit may again include instructions for administering the composition in defined amounts to treat or prevent the infection. In some embodiments, the kit may include instructions for suitable operational parameters in the form of a label or separate insert.

As used herein, the singular forms "a," "an," and "the" may refer to plural articles unless specifically stated otherwise. Therefore, it is to be made clear that reference to an antimicrobial agent being present in the antimicrobial compositions described herein includes reference to use of a combination of antimicrobial agents in the composition.

The term "about" as used in the specification means approximately or nearly and in the context of a numerical value or range set forth herein is meant to encompass variations of +/−10% or less, +/−5% or less, +/−1% or less, or +/−0.1% or less of and from the numerical value or range recited or claimed.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is further illustrated in the following examples. The examples are for the purpose of describing particular embodiments only and are not intended to be limiting with respect to the above description.

EXAMPLE 1

Preparation and Testing of Antimicrobial Compositions

The aim of this study was to characterize nanostructured liquid crystal carriers as a delivery system to promote the antimicrobial action of antimicrobial agents, namely aminoglycoside antibiotics and other cationic antibiotics. The characteristics and antimicrobial activities of the nanostructured liquid crystal carriers were compared across different loaded antibiotics and to simplified liposomal formulations and unformulated solutions in vitro.

Methods

Nanostructured Liquid Crystal Carrier Formation

The nanostructured liquid crystal carrier exemplified in this Example was liquid crystal nanoparticles (LCNPs). LCNPs were formed with monoolein (MO, Myverol 18-99K (part number: 5D01253, Kerry Ingredients and Flavours Egham, Surrey, UK) or phytantriol (PHY, DSM Heerlen, the Netherlands), via the hydrotrope dilution method (Thorn C R et al., 2020, supra). Briefly, MO or PHY (100 mg), Pluronic® F-127 (15 mg) and propylene glycol (0.26 g) were weighed into glass scintillation vials. The mixtures were vortexed for 2 minutes and then completely dissolved in 10 mL chloroform. A stream of nitrogen gas evaporated the chloroform, leaving behind a viscous lipid film on the inside wall of the flask. Thereafter, 0.1 mL of tobramycin (TOB, free base, up to 300 mg/mL), amikacin (AMI, up to 300 mg/mL), gentamicin (GEN, up to 120 mg/mL), ciprofloxacin hydrochloride (up to 60 mg/mL), and Colistin sulfate salt>=19000 U/mg (up to 300 mg/mL) (ChemSupply, Adelaide, SA, Australia) in 0.9% NaCl, was added to hydrate the lipid-hydrotrope mixture and vortexed for 30 seconds. The hydrated lipid-hydrotrope mixture was then further diluted to 5 mL with purified (MilliQ) water and vortex-mixed until a homogenous white emulsion formed (2 minutes).

Liposome Preparation

Liposomes were prepared from a 1:1 mixture of 1,2-distearoyl-sn-glycero-3-phosphocholine (DSPC) and 1,2-dipalmitoylphosphatidylglycerol (DPPG) (0.05/0.05% w/w, Sigma-Aldrich, St. Louis, MO, USA) dissolved in methanol. Using a Nanoassemblr® (Precision Nanosystems, Vancouver, BC, Canada), the benchtop microfluidic device mixed a 1.5:1 (aqueous: organic) ratio of TOB in 0.9% NaCl solution and DSPC/DPPG in methanol with a total flow rate of 12 mL/min. The collected liposomes were then stirred overnight to evaporate off any residual methanol in the mixture. The liposomes were also diluted 1:80 in LB broth, with a final concentration of 0.05 mg/mL DSPC: DPPG and 15 µg/mL TOB.

Particle Size and Zeta Potential

Diluted samples of LCNPs and liposomes (1:1000) in water (viscosity 0.887 cP) were analysed using dynamic light scattering and phase analysis scattering at 25° C. using a Zetasizer Nano ZS (Malvern, Worcestershire, UK) to determine the particle size and zeta potential, respectively.

The built-in software enabled determination of the mean hydrodynamic diameter (reported as the z-average) and the particle size distribution (reported as the poly dispersity index, PDI) over 15 triplicate measurements, with unimodal distributions.

Drug Load and Release

As previously described (Thorn C R et al., 2020, supra), a pressure ultrafiltration stirred cell (Amicon®) was employed to indirectly determine the total amount of antibiotic that was loaded in the LCNPs or liposomes. 2.5 mL of the LCNP or liposome suspensions (undiluted) were transferred into the cell containing a pre-soaked ultrafiltration disc made of biomax polyethersulfone, 500 kDa NMWL (Merck Millipore, Bayswater, Victoria, Australia). Upon applying 100 kPa of nitrogen gas, the LCNPs or liposomes were subjected to ultrafiltration that produced a filtrate free of the LCNPs or liposomes due to the particle size restriction of the ultrafiltration disc. The antibiotic in the filtrate was quantified and represented the portion of unloaded antibiotic. The total amount of antibiotic loaded in the LCNPs or liposomes was quantified through dissolving the LCNPs or liposomes with 5% v/v Triton X. The unloaded antibiotic in the filtrate plus the antibiotic loaded should equate to the total amount of antibiotic originally added and was confirmed. A solution of the antibiotic was also subjected to the same process to confirm the antibiotic passed through the ultrafiltration disc.

After determining the amount of antibiotic that was unloaded in the LCNPs or liposomes, the formulations were diluted 1:5 with buffered media (0.01 M Phosphate Buffered Saline (PBS) buffer, pH 7.4) in the pressure ultrafiltration cell to determine the release. The mixture was magnetically stirred and at specific time points (0, 5, 10, 15, 30, 45, 60, 90, 120, and 240 mins) 0.5 mL samples were collected by applying 100 kPa of nitrogen gas. Immediately after each sample was removed, it was replaced with 0.5 mL of fresh PBS.

Antibiotic concentrations were quantified by high-performance liquid chromatography (HPLC) with UV detection (Shimadzu, Kyoto, Japan), following a derivatization procedure. The derivatization of antibiotic standards and release samples was performed with 1,2-dinitrofluorobenzene (DNFB) (15 mg/mL in 100% ethanol), as previously described (Russ H et aL, 1998, *Journal of Liquid Chromatography & Related Technologies,* 21(14): 2165-2181) and the TOB USP monograph. Briefly, individual TOB, AMI and GEN solutions (80 μL) in 50 mM Tris buffer (pH 7.4) were doped with 10 mM sulphuric acid, 200 μL of 15 mg/mL DNFB and 200 μL of 25 mM Tris in 80% dimethyl sulfoxide (DMSO) in a glass vial. The vials were then placed in a 70° C. water bath for 20 minutes to allow the derivatization reaction to proceed. After 20 minutes, the vials were cooled to room temperature and diluted with acetonitrile (520 μL) for HPLC analysis.

Separation was carried out on a Phenomenex Luna 5 μm C18 100 Å (250×4.6 mm) (Torrance, USA) column equipped with a column guard. The system was maintained at 40° C., with an injection volume of 20 μL and elution with a mobile phase at a flow rate of 1.2 mL/min. The mobile phase was a mixture of 45% (V/V) of 17 mM Tris and 20 mM sulphuric acid in water and 55% (V/V) of acetonitrile. Each sample was analysed over 11 minutes at a detection wavelength of 365 nm, with a retention time of 8.9 minutes. The samples were quantified against known concentrations of each antibiotic (calibration curve 6-120 μg/mL, $R^2$=0.9954, limit of quantification 3 μg/mL).

The rate of TOB released was calculated as previously described (Thorn C R et al., 2020, supra), using Higuchi Equation 1 and plotting the square root of time against the total amount of TOB released. The slope of the plot is equal to the rate of release (Ho N et al., 1972, *J. Theor. Biol.,* 34(3): 451-467; Bisset N B et al., 2015, *Int. J. Pharm.,* 495(1): 241-248).

$$Q=[D_m \cdot C_d(2A-C_d)t]^{1/2} \qquad \text{Equation 1:}$$

Where Q is the amount of drug released per unit matrix (mg/mL), $D_m$ is the diffusion coefficient of the drug in the matrix, A is the initial amount of drug loaded in the matrix, $C_d$ is the solubility in the drug matrix and t is time.

Deposition Efficiency

The Aerogen® Pro (vibrating mesh nebuliser) connected to a nebuliser chamber was used to aerosolise unformulated solutions of TOB, and LCNPs loaded with TOB. The nebulisation chamber fitted into the well of a 24-well plate, ensuring the dose was deposited into a single well. Before use, the nebuliser was rinsed twice with 0.9% NaCl. Then each formulation of TOB was tested to ensure an even aerosol was produced. 100 μL of TOB as an unformulated solution, and in MO-LCNPs and PHY-LCNPs was nebulised into the wells of a 24-well plate that contained 200 μL of 0.9% sodium chloride. The total drug concentration was then determined from each well to calculate the total mass deposited. To ensure no water droplets were expelled during the aerosolization process, the formulations were also nebulised into dry wells, where 0.9% NaCl was added after to determine the drug concentration. The nebulised samples were assessed for particle size and zeta potential, as described above.

For the nebulisation samples and transport studies (see below), TOB was quantified by liquid chromatography tandem mass spectrometry (LC-MS) using a Dionex Ulti-Mate 3000 Binary Rapid Separation LC System (Thermo Scientific, USA) coupled with a TSQ Quantum Access Max (QQQ, Thermo Scientific, USA) and a modified ion-pairing method. Before analysis, LCNPs were dissolved through mixing with 0.05% Triton X and then filtered using 4 mm Millex® syringe filters. The analytical column is a Zorbax Eclipse xdb C-18 column (5 μm, 50*4.6 mm, Agilent, USA) with C18 guard column. As mobile phase, acetonitrile (eluent A) and water (eluent B), each supplemented with 0.1% trifluoracetic acid, 0.1% heptafluorobutyric acid and 0.1% pentafluoropropionic acid were used. Samples were run with a flow of 0.7 mL/min, using a gradient of eluents A and B, starting with a ratio of 20:80 in the first minute. From 1 to 3.5 min the ratio changed to 70:30 and was restored to 20:80 between 3.5 and 4.5 min. 3 μL of the samples were injected and quantification was done by ESI+ and the SRM of the ion 468.184→323.960.

Minimum Inhibitory Concentration (MIC) Determination

The antimicrobial activities of TOB, AMI, GEN, ciprofloxacin and colistin as unformulated solutions or loaded in the MO-LCNPs were assessed by standard microbroth dilution assays with planktonic PAO1 in 96 well plates. A log-phase growth suspension of PAO1 was diluted from an overnight culture to an OD600 of 0.01 and added to the wells of the 96-well plate. The bacteria were diluted 1:1 with serially diluted concentrations of the antibiotic, ranging from 0.125-128 μg/mL. As a control, the bacteria were 1:1 diluted with 0.01 M PBS. After 18 h incubation at 37° C., the inhibitory concentration was determined as the last clear well that had a comparable OD600 value to the sterile media control. Duplicate experiments were completed with four replicates each time.

In Vitro MBEC Antibiofilm Assay

To compare the effect of LCNPs compared to an unformulated solution of TOB, AMI, GEN, ciprofloxacin, and colistin, an MBEC Assay® (Innovotech, Edmonton, AB, Canada) was utilized. An inoculum of PA01 from a freshly streaked agar plate was incubated for 18 h in LB broth before being diluted in sterile water to an OD600 of 0.50±0.10. The bacterial suspension was further diluted 1:100 in LB broth and 200 μL were transferred into wells of the MBEC Assay®. The pegs on lid of the MBEC Assay® were submerged into the bacterial suspension, with column 12 containing sterile LB broth as a negative control. The plate was incubated at 37° C. on a rotating gyrator for 24 h to form biofilm on the pegs. After 24 h, the peg lid was removed and transferred into another 96-well microtiter plate containing sterile water for 30 seconds before being transferred into a treatment plate. The peg lid in the treatment plate was incubated for 24 h at 37° C. on the rotating gyrator.

In the first study, the effect of concentration variation of TOB in MO-LCNPs was determined. The treatment plate contained various concentrations of three different types of formulation: (1) TOB as an unformulated solution, (2) TOB unformulated solution with no drug containing MO-LCNPs, and (3) TOB loaded MO-LCNPs. Each type of formulation was at a concentration of 1 μg/mL, 5 μg/mL, 15 μg/mL and 60 μg/mL. TOB was loaded into the LCNPs at different concentrations between 0.08 to 6 mg/mL as described above in order to achieve a uniform dose of 0.25 mg/mL MO. The respective controls included unloaded formulations MO-LCNP and PHY-LCNP at equivalent concentrations and 0.9% NaCl. LCNPs were also prepared with ciprofloxacin, as previously reported (Thorn C R et al., 2020, supra) with concentrations that matched TOB, for a comparison between the LCNPs with different antibiotics.

In the second study, the difference in effect of MO- and PHY-LCNPs compared to liposomes containing TOB was determined. The treatment plate contained: 200 uL of TOB (15 μg/mL) as an unformulated solution and formulated as MO-LCNP and PHY-LCNP, all diluted 1:80 in LB broth. The final concentration of MO and PHY was 0.25 mg/mL. Liposomes were prepared as described above.

In the third study, TOB, AMI and GEN as unformulated solutions and loaded in MO-LCNPs were compared as treatments against PAO1 biofilms in the MBEC Assay®. The concentration of each antibiotic was 6 μg/mL.

In the fourth study, colistin loaded MO-LCNPs were compared to the unformulated solution as treatments against PAO1 biofilms in the MBEC Assay®. The concentration measured included; 5 μg/mL, 15 μg/mL and 60 μg/mL.

In all four different studies, the treatments were incubated with the PAO1 biofilm grown on the MBEC Assay® on a rotating plate at 37° C. After 24 h incubation, the peg lid was transferred to a fresh plate containing sterilized water to inhibit treatments. Using sterilized pliers, individual pegs were removed from the lid and placed in 1 mL of sterile water in Eppendorf tubes. For each treatment, 3 pegs were collected individually and subjected to 2 cycles of bath sonication for 1 minute and vortex mixing for 30 seconds to dislodge and suspend the bacteria from the pegs. Serial dilutions and agar dilutions were prepared followed by enumeration by colony forming units (CFU). In addition to the three technical replicates, the assay was completed on three different occasions (biological replicates).

Cell Toxicity

The CFBE41o− cell line (Gruenert Cell Line Distribution Program) was seeded at $0.02 \times 10^6$ cells/well in a 96 well plate in MEM media (passage number 4.86-4.86). The cells were incubated at 37° C. at 5% $CO_2$ for 18 h to allow them to adhere. Thereafter, the cells were washed once with PBS and the respective treatments were added. 0.01-10 mg/mL of MO- and PHY-LCNPs loaded with and without tobramycin were prepared from stocks of LCNPs diluted in MEM media. Non-treated cells and cells treated with 5% Triton X were used as respective positive and negative controls. The plates were re-incubated for 24 h. After 24 h, the 96-well plates were centrifuged at 400×g for 5 minutes. 100 μL of the supernatant was transferred to a new 96 well plate and each well was mixed with 100 μL of Cytotoxicity Detection Kit (LDH) (Roche), as per the manufacturer's instructions. After a 5-minute incubation at room temperature, the LDH was quantified by reading the absorbance of each well at 492 nm. The % viability was calculated by subtracting the absorbance of the treated well from the absorbance of Triton X treated well, divided by the absorbance of the Triton X treated well, multiplied by 100. Four individual experiments were carried out, each with 2 replicates, providing a total of 8 replicates.

Transferred Biofilm Model

Taking into account the toxicity data of the MO-LCNPs, additional biofilm activity studies were conducted to ensure a non-toxic concentration of MO-LCNPs maintained the activity of TOB in the MBEC Assay® PAO1 biofilm model. A variation in this biofilm model was employed to contrast the effect of the MO-LCNPs compared to the standard, MBEC® model. Briefly, from an overnight culture, PAO1 was diluted in M63 media to an OD of 0.01 in 500 μL in 24 well plates and incubated for 72 h at 37° C. to form biofilms. Breath seals were used to permit gas exchange during the 72 h incubation period. The 72 h biofilms were then washed with 200 μL PBS to remove planktonic bacteria. Then, using 500 μL of M63 buffer, the biofilms was scraped off from the bottom of the 24-well plate using a 1 mL pipette tip and transferred into a fresh plate. This formed microcolonies of biofilm that closely resembles the clinical environment. The treatments were then added on top of the biofilms and incubated for a further 24 h at 37° C. The treatments included 15 μg/mL of an unformulated TOB solution and TOB loaded in the MO-LCNPs The amount of Pluronic F-127 in the MO-LCNPs TOB formulation was also varied to determine the effect the surface stabiliser had on the antimicrobial effect. The original formulation had 0.3% w/v in the final preparation, where MO-LCNPs were also prepared without any Pluronic-F127 and a higher amount (5% w/v). Both no Pluronic F-127 MO-LCNPs TOB and 5% w/v Pluronic F-127 MO-LCNPs TOB were included as the treatments, at a dose of 15 μg/mL TOB. The concentration of MO-LCNPs for all samples was 0.025 mg/mL.

Chronic Infection Model: CFBE41o− and PAO1

A chronic infection model was developed which cultures *P. aeruginosa* biofilm on top of the bronchial CF epithelium cells (CFBE41o−) at an air-liquid interface. It is a biologically relevant, 3D model that resembles the infected lungs of CF patients.

To assess the activity and toxicity or formulations, the CFBE41o− cell line was seeded on Transwell® inserts ($0.05 \times 10^6$) at the liquid-liquid interface (500 μL apical and 1500 μL basolateral) on day 0. On day 3, the apical side media was removed, and the basolateral side was replaced with 500 μL of media. On day 7, the transepithelial electrical resistance (TEER) was measured through adding 500 μL to the apical chamber of one well and replacing the basolateral side with 1500 μL. The transferred biofilm model, described above, was employed to transfer the PAO1 biofilm on top of the CFBE41o− cell line in the apical compartment of the Transwells® on day 7. After 1 h incubation, the supernatant was removed as the biofilm has settled onto the cells.

Using the Aerogen® Pro (vibrating mesh nebuliser) and nebulisation chamber, the treatments were then nebulised on top of the biofilm and CFBE41o− cell layer. TOB as an unformulated solution or loaded in the MO-LCNPs were dosed at 10 µg, which was equivalent to 100 µL of 3.32 mg/mL for unformulated TOB and 2.50 mg/mL for MO-LCNPs loaded with TOB. The treatments were prepared by diluting the stock solution/LCNPs suspension to the required concentration in KRB buffer. Each time the nebuliser was first rinsed with KRB buffer and the Transwell® to be dosed was transfered to a clean 12 well plate. The treatment was nebulised following a 30 second deposition waiting time. After all treatments were dosed, the Transwells® were replaced to their original well that included fresh MEM media supplemented with 1% arginine (500 µL) and incubated for the required time at 37° C.

At the time points 24 h and 48 h, different read outs were obtained, including bacterial counts, viability of cells and barrier integrity. Bacteria were enumerated through adding 500 µL of sterile cold milliQ water to the apical compartment and replacing the basolateral compartment with 1000 µL. The cold water lysed the cells and after 10 minutes, a pipette tip was used to scratch off the remaining biofilm and transfer all of the contents of the apical compartment into an Eppendorf tube. To ensure all bacteria was removed, a further 500 µL of PBS+0.05% Tween 80 was added to the apical compartment to wash the compartment and transferred into the same Eppendorf tube. Serial dilutions up to $10^{10}$ were performed and 20 µL of each dilution was plated onto LB agar plates. The plates were incubated for 18 h at 30° C. before the colonies of bacteria were counted.

Cell viability was assessed through taking the contents of the basolateral compartment media and reacting it with a Cytotoxicity Detection Kit (LDH) (Roche) to determine the amount of LDH released. 200 µL of the basolateral media was taken and centrifuged at 300×g for 10 mins. 100 µL of the supernatant was mixed with 100 µL of the reaction solution, as per manufacturer's instructions. LDH release was measured after 5-minute incubation at room temperature using a plate reader at an absorbance of 492 nm.

The barrier integrity of the CFBE41o− cell line cultured on the Transwell® supports was determined by both TEER (Srinivasan B et aL, 2015, *Journal of Laboratory Automation*, 20(2): 107-126) and sodium fluorescein transport (Molenda N et al., 2014, *PLOS ONE*, 9(6): p. e100621). Due to the variation in TEER measurements, sodium fluorescein transport provided a direct measurement of the tight junctions. On day 7 (4 days after cells are transferred to ALI), cells were incubated basolaterally with 1.7 mL KRB buffer and apically with 520 µL of 10 µg/mL sodium fluorescein (in KRB) with or without 16 mM ethylenediaminetetraacetic acid (EDTA). EDTA disrupts the tight junctions of a cell barrier. At 30-minute intervals, 20 µL samples were taken from the basolateral compartment and replaced with fresh KRB. During the transport study, the plates were incubated at 37° C. on a MTS orbital shaker (150 rpm, IKA, Germany). The samples were then measured and compared to a standard curve via fluorescent spectroscopy (Tecan® plate reader, Tecan Deutschland GmbH, Germany) at excitation and emission wavelengths of 530 nm 488 nm, respectively. The amount of sodium fluorescein transported was plotted against time, where the slope was taken to calculate the apparent permeability coefficients (Papp) (Ma B et al., 2014,

*Int. J. Clin. Exper. Pathol.*, 7(5): 1957-1966; Hubatsch I et al., 2007, *Nature Protocols*, 2(9): 2111-2119).

$$P_{app} = \frac{dQ}{dt} \times \frac{1}{A \times C_o} \qquad \text{Equation 2}$$

Where, the slope is dQ/dt, a is the area of the Transwell® insert and $C_0$ is the initial concentration of sodium fluorescein in the apical compartment.

Tobramycin Transport

After TOB treatments were nebulised, at 5, 15, 30, 60, 120, 240 and 1440 minutes, 100 µL sample was taken from the basolateral compartment and replaced with fresh MEM media. The sample was then filtered through 4 mm Millex® syringe filters before LC-MS/MS analysis, as described above, to quantify the transport of TOB.

Confocal Microscopy

A two-channel transmission flow cell (Biosurface Technologies, Montana, US) was attached to a media bottle containing 1% LB broth via a bubble trap, similar to previous methods (see Tseng B S et al., 2013, *Environmental Microbiology*, 15(10), 2865-78; and Christensen B B et aL, 1999 *Methods in Enzymology*, 310, 20-42). Upon stopping the flow, an overnight culture of PAO1 GFP strain was diluted to an OD of 0.01 and injected into the flow cell. The bacteria were allowed to attach for 1 h before the flow (0.4 mL/min) was resumed. The biofilm was constantly under flow of fresh 1% LB broth at 37° C. for three days. 15 µg/mL of Cy5 TOB (Biosynthesis, Texas, US, Lot number: SP2260-1) unformulated in 0.9% NaCl or loaded as previously described for MO-LCNPs (0.05 mg/mL) was then injected into separate channels of the flow cell and imaged via laser scanning microscopy using a 63× oil immersion lens (Zeiss, LSM700, Oberkochen, Germany) at 0.5, 1 and 2 h following injection. Zen Blue and ImageJ software were used to complete the analysis of z-stack images.

Statistical Analysis

Data is reported as mean±standard deviation. One-way analysis of variance (ANOVA) assessed the difference in the deposition efficiency and antimicrobial activities of various formulations (as described in the Figures). Statistical significance was evaluated at the 95% confidence interval. All tests were performed using GraphPad Prism (version 7.00 for Windows; GraphPad Soft-ware, La Jolla, CA).

Results and Discussion

Composition Formation, Antibiotic Release, and Deposition Efficiency

TOB loaded LCNPs were formed with well-defined particle sizes of 170 nm and 200 nm for MO- and PHY, respectively. PHY-LCNPs were notably less stable than MO-LCNPs, often separating from suspension and required constant mixing via bath sonication before use. Both LCNPs had a slightly negative surface charge and an average encapsulation efficiency of 85%, with the loading of TOB between 21% and 25% w/w of lipid. Liposomes with a comparable particle size and decreased zeta potential were also formed, along with LCNPs that had varying amounts of the surface stabiliser Pluronic F-127, as shown in FIG. 1.

Thorn C R et al., 2020, supra., detailed MO-LCNPs to be responsive to bacteria, via bacterial lipase production triggering the release of loaded large molecular weight and hydrophobic antimicrobials. In line with the previous reports on ciprofloxacin loaded LCNPs (Thorn C R et al., 2020, supra), TOB was released rapidly from the LCNPs within two hours. Due to the low molecular weight and hydrophilic nature of TOB and ciprofloxacin, the diffusion-controlled release from the aqueous channels is rapid and would co-occur with the bacterial lipase digestion the LCNPs crystalline structure. TOB's release from the MO-LCNPs was initially higher compared to PHY-LCNPs, however, became equivalent after the plateau. The rate of TOB released from MO- and PHY-LCNPs were 208 $\mu g/min^{1/2}$ and 272 $\mu g/min^{1/2}$, respectively, and at least 5-fold higher compared to the release from the liposomes. Liposomes are known to retain a higher amount of small, hydrophilic molecules, where previously, at least 80% of TOB remained within the core of the lipid bilayer (Lagacé J M et al., 1991, *Journal of Microencapsulation,* 8(1), 53-61). LCNPs are three-dimensional constructs of multiple lipid bilayers, where the water channels remain exposed on the outside, unlike the single lipid bilayer of liposomes that encloses the aqueous compartment. Therefore, the complete rapid release of TOB from LCNPs was expected due to the configuration of the lipid nanoparticles.

To the best of our knowledge, LCNPs have never been proposed for pulmonary drug delivery. Following nebulisation, the LCNPs maintained their particle size, as demonstrated in FIG. 2. The zeta potential increased toward neutral, likely from nebulising the nanoparticles in isotonic 0.9% saline. The deposition efficiencies of TOB in an unformulated solution, MO-LCNPs and PHY-LCNPs were consistent at 3.25%, 4.05% and 3.12%, respectively. During nebulisation, the drug can be lost during the aerosolising process, adhering to the walls of the nebuliser unit or within the vibrating mesh. Hence the low deposition efficiencies observed are not uncommon.

Previously, the nanoparticle characteristics and technique of aerosol generation have affected nanoparticle aggregation following nebulisation, where hydrophilic surfaces and ultrasonic nebulisation decreased nanoparticle aggregation (Dailey L A et aL, 2003, *Journal of Controlled Release,* 86(1): 131-144). The LCNPs have an overall hydrophilic surface due to the Pluronic F-127 surface coating. While the Aerogen nebuliser used creates an aerosol through a vibrating mesh technology, which uses ultrasonic frequencies to vibrate the mesh, limited aggregation was observed in the aerosol, similar to ultrasonic nebulisers. The limitation aggregation and consistent deposition efficiencies suggest LCNPs TOB formulations can maintain their structure and action following nebulisation.

In Vitro MIC Determination

The MIC of five different antibiotics can be observed in FIG. 3. Unexpectedly, the MIC is decreased at least 50% upon the antibiotic being loaded into the MO-LCNPs demonstrating a significant synergistic interaction between each antibiotic and the LCNPs.

In Vitro MBEC Antibiofilm Assay: TOB and CIP

The antimicrobial effect of TOB in a simplified PAO1 biofilm model was enhanced significantly upon loading into LCNPs. Compared to the unformulated solution and when combined with unloaded LCNPs, TOB loaded LCNPs reduced the load of PAO1 by three-and two-log, respectively, at a range of concentrations (FIG. 4A). While the MO-LCNPs did not have any antimicrobial activity and maintained a constant concentration despite the varying TOB concentrations, TOB's antimicrobial activity increased in a dose-responsive nature from being loaded in the MO-LCNPs.

At 5 $\mu g/mL$ and 15 $\mu g/mL$, MO-LCNPs TOB reduced the PAO1 load by 5-log, compared to the no treatment control, while the unformulated antibiotic alone and combined with unloaded LCNPs reduced the load by 2- and 3-log, respectively. At the higher concentration of 60 $\mu g/mL$, MO-LCNPs TOB resulted in less than 10 CFU/mL of PAO1, which is near-complete eradication after one single treatment, with a total 5-log reduction to the unformulated solution. The 60 $\mu g/mL$ unformulated TOB solution with unloaded MO-LCNPs also produced a 2-log reduction, compared to the unformulated solution alone (P<0.05).

Figure 4B:
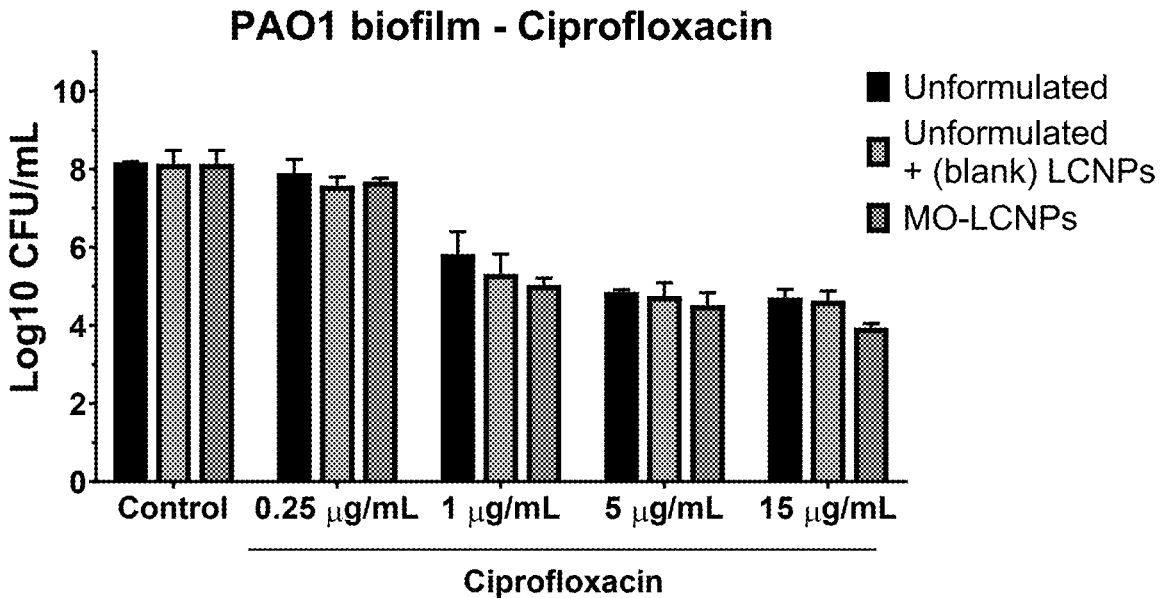

However, for a different antibiotic (i.e. ciprofloxacin—which has no charge), the antimicrobial effect could not be enhanced by loading into the LCNPs (FIG. 4B). As aforementioned, the MO-LCNPs ciprofloxacin formulation was previously characterised and demonstrated a similar release profile to TOB (Thorn C R et al., 2019, supra). At a range of concentrations, ciprofloxacin's antimicrobial effect in the simplified PAO1 biofilm model did not alter after loading in LCNPs nor with the combination of unloaded LCNPs (FIG. 4B), where ciprofloxacin's activity was unable to be further decreased beyond 4-log.

The difference in effect between TOB and ciprofloxacin resembles their differences in biofilm penetration. Due to the positive charges from the amino-groups, TOB is bound electrostatically to the negatively charged exopolysaccharides in the EPS matrix of the biofilm, and unable to reach the lower levels of bacteria to exert its effect on the protein synthesis of bacteria (Tseng B S et al., 2013, supra). At the neutral pH of the LB media, ciprofloxacin is uncharged and penetrates the biofilm matrix, where the limited antimicrobial effect in biofilms is due to the inability to act on dormant, non-log phase growing bacteria.

The differences in TOB's penetration are represented in scanning electron confocal micrographs of PAO1 tagged with GFP biofilms grown in a flow cell for three days in 1% LB broth and injected with Cy5 labelled tobramycin as an unformulated solution or loaded into R18 tagged MO-LCNPs. The unformulated fluorescently tagged antibiotic did not penetrate the biofilm, as observed in FIG. 5A, with a total area under the curve of the fluorescent TOB being 274, 459 and 464 AU/$\mu m^2$, for 0.5, 1 and 2 h, respectively. When loaded into the MO-LCNPs, the Cy5 TOB readily penetrated deep into the biofilm (FIG. 5B) with significant increases in the area under the curve, represented by 1209, 1509 and 1157 AU/$\mu m^2$ at 0.5, 1 and 2 h, respectively (P<0.01). Similarly, Tseng B S et al., 2013, supra, observed the inability of Cy5 TOB to penetrate the biofilm, while Cy5 dye alone penetrated. Cy5 ciprofloxacin also penetrated biofilm, as we have observed in the unformulated solution and when loaded in the MO-LCNPs (FIGS. 5C and 5D). However, the penetration of unformulated ciprofloxacin is not broadly spread across the biofilm, where it peaks at the surface at 0.5 h and gradually increases towards the biofilm's centre from 1 to 2 h (FIG. 5C). When loaded in the MO-LCNPs, ciprofloxacin spread more evenly within the biofilm with a similar intensity profile to tobramycin loaded MO-LCNPs (FIG. 5D). While the area under the curves of unformulated CIP (746, 805, 1403 AU/$\mu m^2$, for 0.5, 1 and 2 h, respectively) were lower compared to when loaded in the MO-LCNPs (1366, 1162, 1711 AU/$\mu m^2$, for 0.5, 1 and 2 h, respectively), they were not statistically significant (P=0.15). In addition, the areas under the curve of the unformulated and MO-LCNPs loaded ciprofloxacin were similar to tobramycin loaded MO-LCNPs.

Figures 6A, 6B:
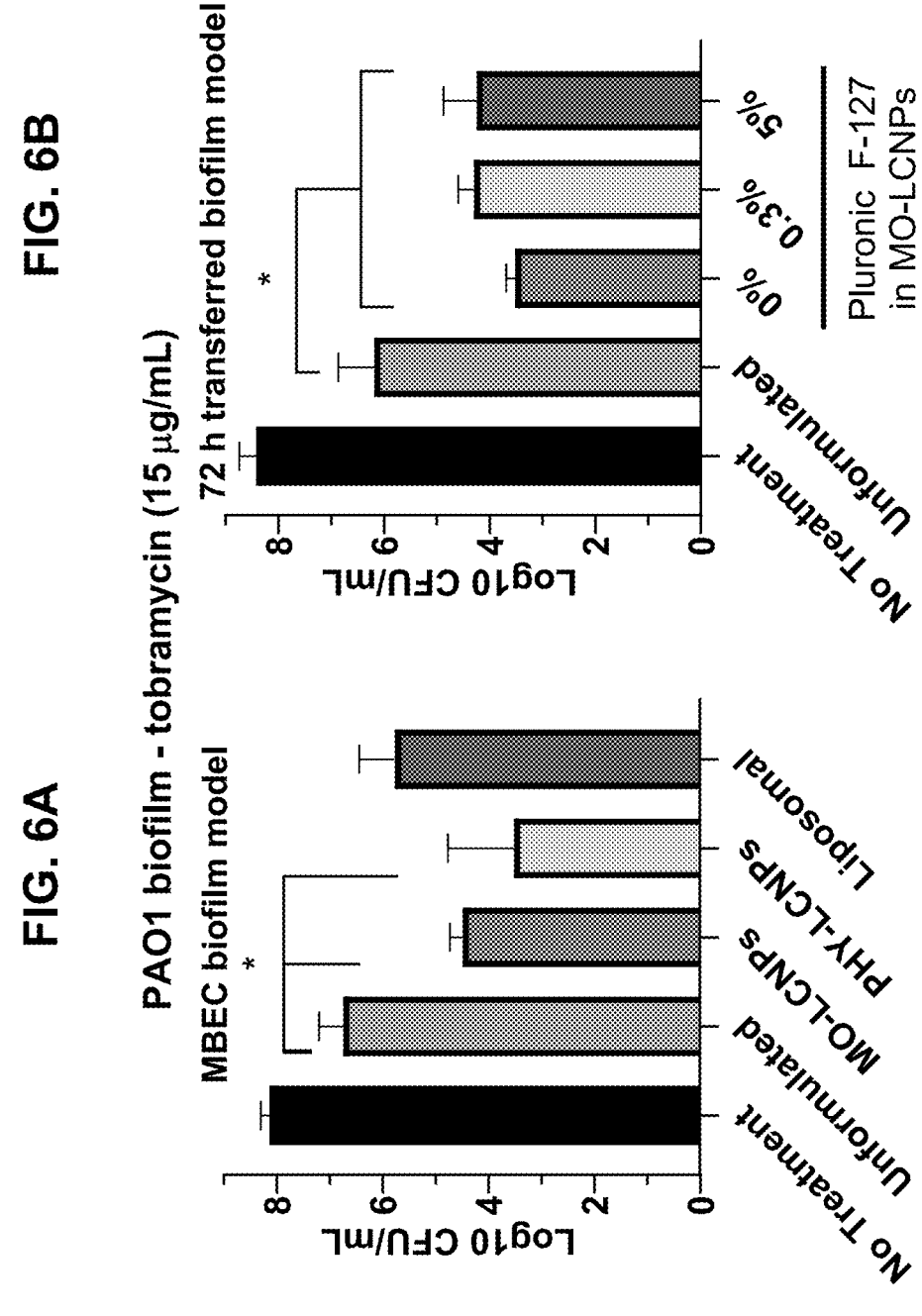
FIGS. 6A-6B—graphs showing the activity of different tobramycin formulations against *P. aeruginosa* biofilms. The graph in (A) shows the total amount of PAO1 remaining after PAO1 biofilm (formed on MBEC® model) was treated with tobramycin (15 μg/mL) as unformulated solution and formulated as MO-LCNPs, PHY-LCNPs and DSPC: DPPG liposomes, The graph in (B) shows the total amount of PAO1 remaining after PAO1 biofilm (from transferred biofilm method) was treated with tobramycin (15 μg/mL) as an unformulated solution or formulated in MO-LCNPs and MO-LNCPs containing no or a higher amount of Pluronic F127 MO-LCNPs=0.05 mg/mL. Data represented as mean±standard deviation, n=9 (3 independent experiments), one-way ANOVA * P<0.01.

Comparison of Antibiofilm Effect Across Different Lipid Nanoparticle Formulations The enhanced activity of TOB loaded LCNPs was not unique to the lipid forming the LCNPs, where both MO-LCNPs and PHY-LCNPs demonstrated similar 3-log reductions in TOB's antimicrobial activity at 15 $\mu g/mL$ against the simplified PAO1 biofilms (compared to unformulated TOB, at an equivalent concentration) (FIG. 6A). Although PHY has known antimicrobial properties (EP 3 485 869 A1), at the concentration used, no innate activity occurred. Decreasing the concentration of MO-LCNPs by 5-fold (to 0.05 mg/mL), while maintaining TOB's concentration at 15 µg/mL also did not alter the enhanced anti-biofilm effect from loading TOB into the LCNPs.

The enhancement in TOB's activity was unique to the LCNPs themselves, whereby liposomes of similar particle size did not enhance TOB's antimicrobial activity against MBEC grown PAO1 biofilms (at an equivalent concentration of 15 µg/mL) (FIG. 6A). Liposomal formulations have been widely explored as a technique to enhance the antimicrobial activity of antibiotics, particularly aminoglycosides due to their fusogenic and surface properties (Sachetelli S et aL, 2000, Biochimica et Biophysica Acta, 1463(2): 254-66; and Beaulac C et al., 1996, Antimicrobial Agents and Chemotherapy, 40(3): 665-669). Liposomes with lower rigidities and transition temperature were more favourable in vivo to increase aminoglycosides antimicrobial activity due to fusing with bacteria and termed Fluidsomes™ properties (Sachetelli S et al., 2000, supra; and Beaulac C et al., 1996, supra). Liposomes are a simplified version of LCNPs, in which a lamellar bilayer forms the core of the particles with an inner aqueous cavity. Various phospholipids have been proposed and patented as formulations to increase the activity of TOB, gentamicin and amikacin (Halwani M et al., 2007, Journal of Antimicrobial Chemotherapy, 60(4): 760-769; Alhariri M et al., 2017, International Journal of Nanomedicine, 12: 6949-6961; and Waters V and Ratjen F, 2014, Expert Review of Respiratory Medicine, 8(4): 401-9). Recently there has also been the successful marketing of Arikayce® (Shirley, M., 2019, Drugs, 79(5): 555-562).

While liposomes do have the potential to increase the effectiveness of antibiotics, certain phospholipid combinations are required to achieve this effect. In comparison to liposomes composed of 1,2-distearoyl-sn-glycero-3-phosphocholine (DSPC) and 1,2-dipalmitoylphosphatidylglycerol (DPPG), both MO- and PHY- LCNPs were better at enhancing the antimicrobial effect of TOB. The soft crystalline structures of the lipid bilayers in LCNPs have also demonstrated fusogenic properties with biological lipid bilayers (i.e. cell membranes) due to the similarity in composition (Hinton T M et al., 2014, Toxicology Research, 3(1): 11-22; and Dyett B P et al., 2019, Nature Communications, 10(1): 4492). Although, as opposed to the unilamellar bilayer of liposomes, LCNPs have bilayers with infinite minimal surfaces providing a greater surface area for interaction (Barriga H M G et al., 2019, Angewandte Chemie, 58(10): 2958-2978). LCNPs also produce superior skin retention compared to liposomes (Rattanapak T et al., 2012, Journal of Pharmacy and Pharmacology, 64(11): 1560-9), suggesting the multi-faceted lipid bilayer has potentially enhanced penetrative effect to a higher degree than unilamellar vesicles.

Differences similarly arose in the surface zeta potential of the LCNPs and liposomes, where the LCNPs zeta potential increases towards −9.5 and −13.4 mV (for MO and PHY, respectively), while the liposomes remained negative (−43.5 mV). Messiaen et al., 2013, PLOS ONE, 8(11): e79220 demonstrated negatively charged nanoparticles to be immobilised near the biofilm cell clusters but failed to modulate the antimicrobial activity due to repulsion from the negatively charged cell wall of bacteria. The R18 tagged MO-LCNPs visibly formed a sock-like coating over the biofilm, which is predicted to facilitate the penetration of TOB through the EPS matrix. While the LCNPs have a slightly negative surface charge, they may be implicated by some repulsive forces, but their slight penetration is enough to release TOB directly to the bacteria, increasing the total concentration inside the biofilm. Similarly, slightly negative or near-neutral surface charged nanoparticles were preferentially better to target the biofilm compared to highly negative or positive particles.

Moreover, the enhanced effect of TOB MO-LCNPs did not differ between the two different in vitro biofilm models (i.e. MBEC® model and the transferred biofilm model). Compared to a two log-reduction after unformulated TOB treatment, a four-log reduction in PAO1 load resulted from TOB MO-LCNPs treatment at 15 µg/mL TOB and 0.05 mg/mL MO-LCNPs, using the transferred 72 h biofilm model FIG. 6B. Compared to the transferred biofilm, where the biofilm rests on the bottom of a well plate, the biofilm on the polystyrene pegs in MBEC® model is suspended and reduces the bias of increased (nano)particle settlement (Ceri H et aL, 1999, supra). Although, regardless of the in vitro biofilm model, the effect of TOB was increased by the LCNPs.

The surface coating can also dictate the permeation of a particle through a biological barrier, with extensive work focused on mucus penetrative PEGylated nanoparticles (Schneider C S et aL, 2017, Science Advances, 3(4): e1601556; and Yang M et al., 2011, Angewandte Chemie, 50(11): 2597-600). Where a nanoparticle coated with a sufficient amount of a low molecular weight polyethylene glycol (PEG) polymer enhances the particle's penetration through mucus, regardless of the particles core nature. Pluronic F-127 is an example of a biocompatible, commercially available polymer that is a triblock copolymer of PEG-polypropylene glycol-PEG. Pluronic F-127 has drastically enhanced the mucus penetration of sub-300 nm organic, polymeric and lipid nanoparticles, in vitro, ex vivo and in vivo (Schneider C S et al., 2017, supra; and Yang M et al., 2011, supra). As a biofilm has an extensive EPS matrix, that has a chemical and physical resemblance to thick mucus, we hypothesised that decreasing the Pluronic F-127 coating would remove the enhanced antimicrobial effect of TOB while increasing the Pluronic F-127 concentration would increase the effect further.

Typically, the MO-LCNPs contained 0.3% (w/v) Pluronic F-127. To vary the concentration, MO-LCNPs were formed with a higher amount of Pluronic F-127 (5% w/v) and with no Pluronic F-127. As observed in FIG. 1, increasing the amount of Pluronic F-127 in the formulation halved the particle size of the LCNPs, while removing Pluronic F-127 from the formulation did not affect the particle size of the MO-LCNPs. Intriguingly, the Pluronic-F127 concentration did not alter the effect of the MO-LCNPs, regardless if there was a surfactant coating or not. In FIG. 6B, all three variations of TOB MO-LCNPs achieved a 2-log greater reduction in PAO1 load compared to an unformulated solution. Due to the limited variation in MO-LCNPs TOB effect across the different Pluronic F127 concentrations, this further strengthens the argument that enhanced activity of TOB in the LCNPs is unique to the liquid crystalline structure of the nanoparticles.

In Vitro MBEC Antibiofilm Assay: Other Aminoglycosides

Figure 7:
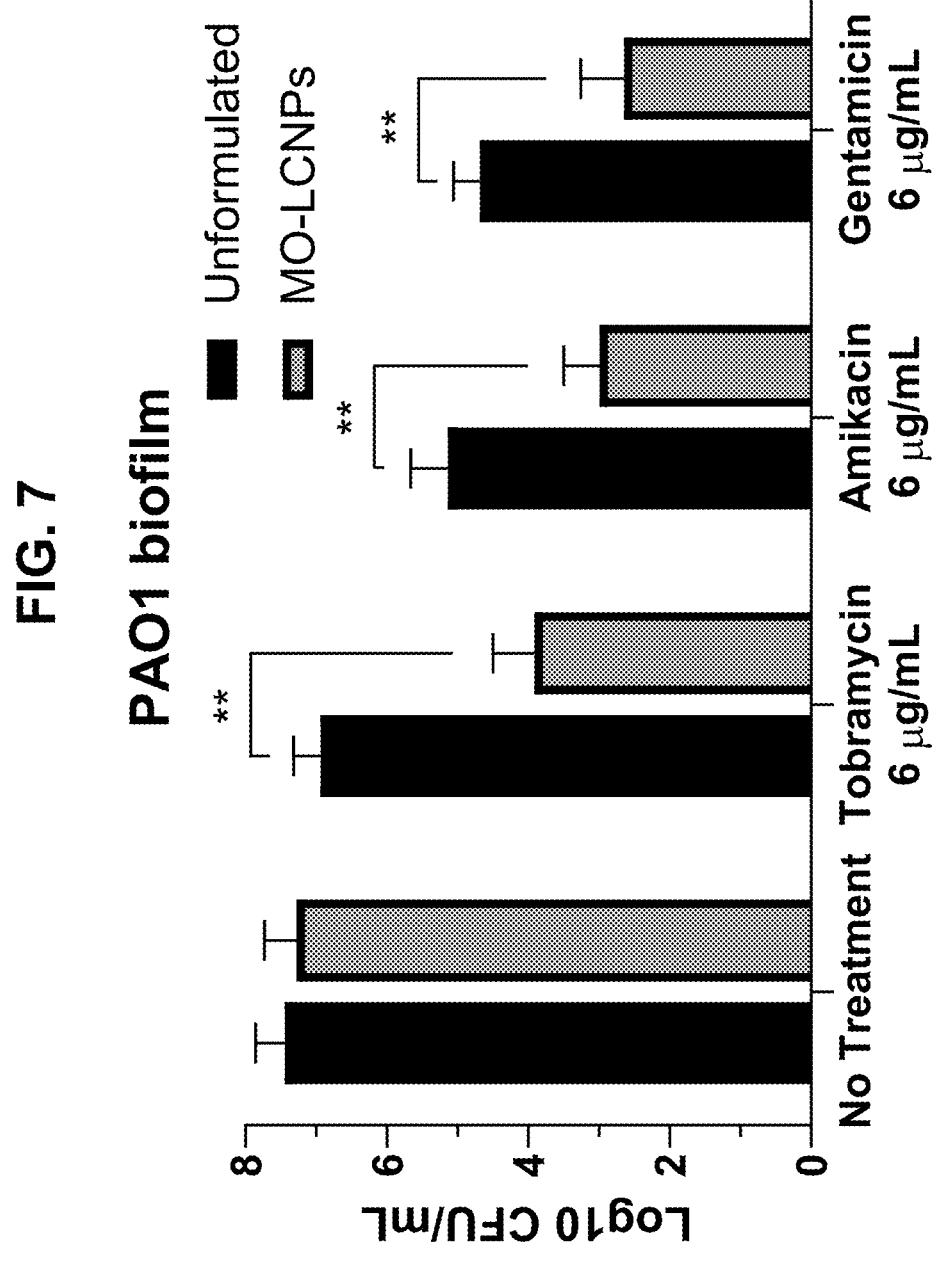
FIG. 7—a graph demonstrating the activity of different aminoglycoside LCNPs formulations against *P. aeruginosa* biofilms. The graph shows the total amount of PAO1 remaining after PAO1 biofilm (formed on MBEC® model) was treated with 6 μg/mL tobramycin, amikacin or gentamicin as an unformulated solution or in MO-LCNPs (0.05 mg/mL). Data represented as mean±standard deviation, n=9 (3 independent experiments), ** P<0.001 two-way ANOVA followed by Sidak multiple comparisons test.

Loading other aminoglycosides into the MO-LCNPs, including amikacin and gentamicin, also resulted in at least 2-log greater reduction in PAO1 biofilm compared the unformulated aminoglycosides (FIG. 7). As aforementioned, the cationic charge on aminoglycosides limits their penetration across the EPS matrix of biofilms, leading to a limited antimicrobial effect. Therefore, the MO-LCNPs are claimed to advance the activity of the aminoglycosides class through permitting their penetration across the biofilm.

In Vitro MBEC Antibiofilm Assay: Other Cationic Antibiotics

Figure 8:
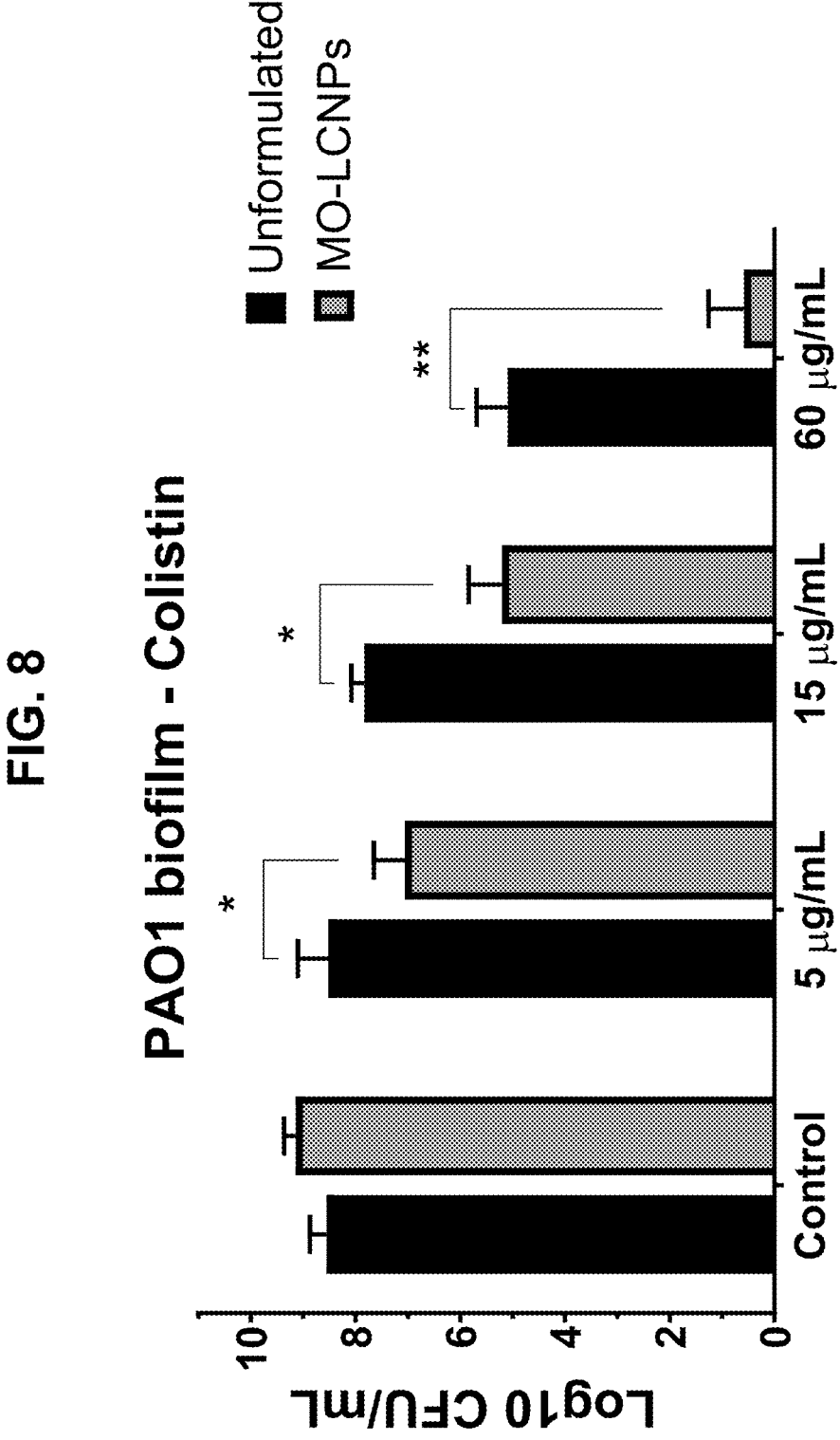
FIG. 8—a graph demonstrating the activity of a different cationic antibiotic (colistin LCNPs formulations) against *P. aeruginosa* biofilms. The graph shows the total amount of PAO1 remaining after PAO1 biofilm (formed on MBEC® model) was treated with 5 μg/mL, 15 μg/mL, 60 μg/mL of colistin as an unformulated solution or in MO-LCNPs (0.05 mg/mL). Data represented as mean±standard deviation, n=6 (2 independent experiments), ** P<0.001 two-way ANOVA followed by Sidak multiple comparisons test.

Colistin is an entirely different antibiotic to aminoglycosides and used as a last line therapy against multi-drug resistant Gram-negative organisms. It is also cationic in nature and has limited activity against bacterial biofilms. As shown in FIG. 8, in PAO1 biofilms grown in the MBEC® model, 5-15 µg/mL of colistin (unformulated) solution had no anti-biofilm or antimicrobial effect compared to the control of saline treatment. When loaded into MO-LCNPs, of similar particle characteristics to previous explanations, at 5 µg/mL there was a 1.5-log greater reduction in PAO1 biofilm compared to the unformulated solution. At 15 µg/mL, there was a 2.6-log reduction from the MO-LCNPs compared to the unformulated solution of colistin. Higher concentrations of colistin (i.e. 60 µg/mL) produce a similar anti-biofilm effect to the MO-LCNPs loaded colistin at 15 µg/mL. However, 60 µg/mL of colistin loaded in the MO-LCNPs resulted in near-complete eradication of the PAO1 biofilm with less than 1 log of bacteria remaining, from a total amount of $3.5 \times 10^8$ CFU/mL.

Cell Toxicity, Transport and the Chronic Infection Model

Figures 9A, 9B:
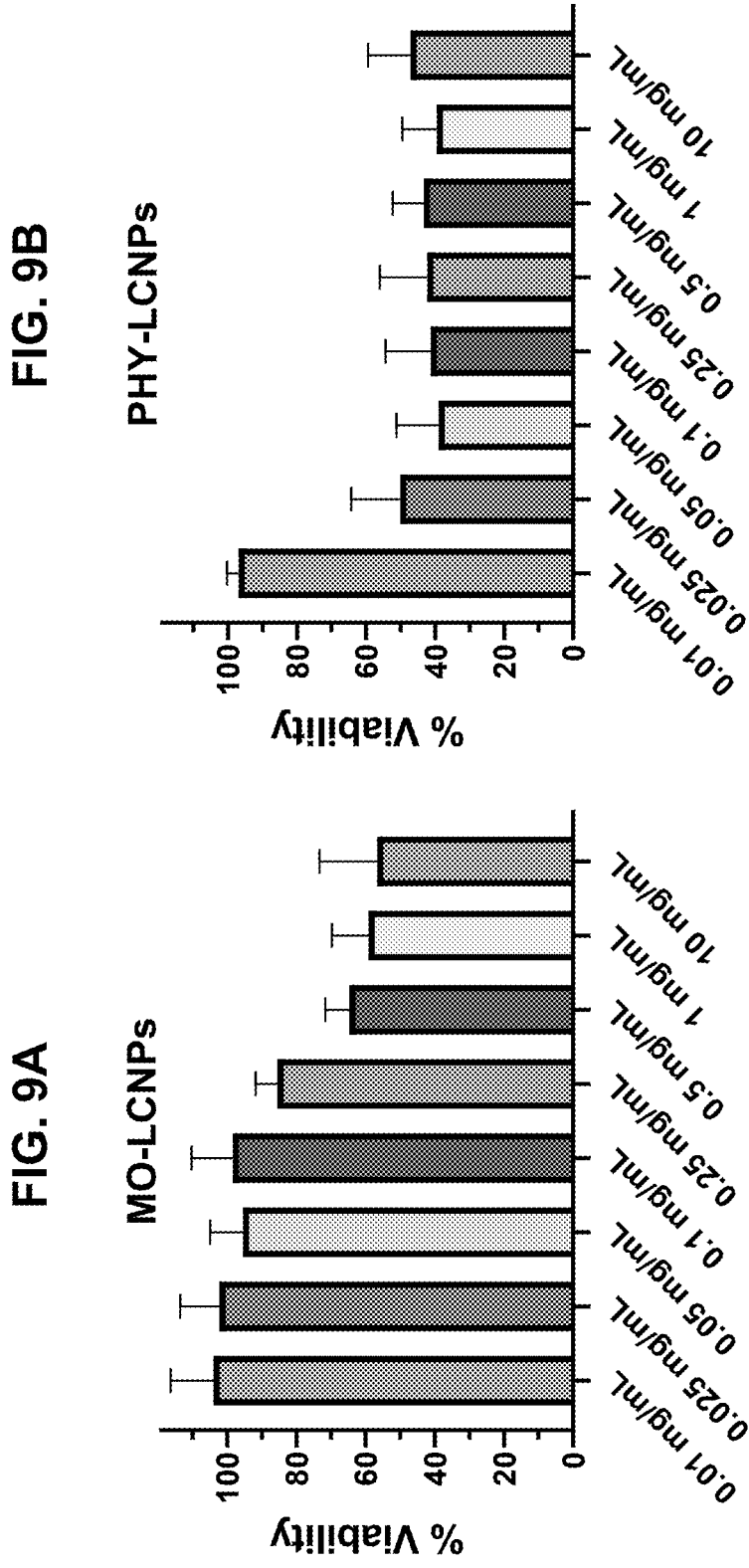
FIGS. 9A-9B—graphs showing the viability profile of the CFBE41o− cell line after 24 h exposure to MO- and PHY-LCNPs. The graphs show the percentage of CFBE41o− cells (P 4.85, P 4.86) that were viable and normalised to control of 0% viability following incubation 5% Triton X, after treatment with varying concentrations of MO-LCNPs (A) and PHY-LCNPs (B). CFBE41o− was seeded at 0.2×10⁶ cells/well. Data represented as mean±standard deviation, n=8 (4 independent experiments).

In the cystic fibrosis bronchial epithelium cell line (CFBE41o−), the MO-LCNPs were considered non-toxic (viability>85%) at a concentration range from 0.01-0.25 mg/mL, while the PHY-LCNPs were non-toxic below 0.01 mg/mL (FIG. 9). While both MO and PHY are generally recognised as safe (GRAS) compounds by the Food and Drug Administration (FDA) and used widely in the cosmetic and pharmaceutical industry, the cellular toxicity profiles were consistent with previous reports on cellular toxicity (Tan A et al., 2019, supra). The higher toxicity of PHY-LCNPs is also related to their greater potential to fuse with membranes compared to MO-LCNPs, with a greater propensity to causes haemolysis in healthy cells (Hinton T M et aL, 2014, supra). Given the higher toxicity of PHY-LCNPs and the instabilities of the formulation, all preceding studies were with MO-LCNPs.

Figure 10A:
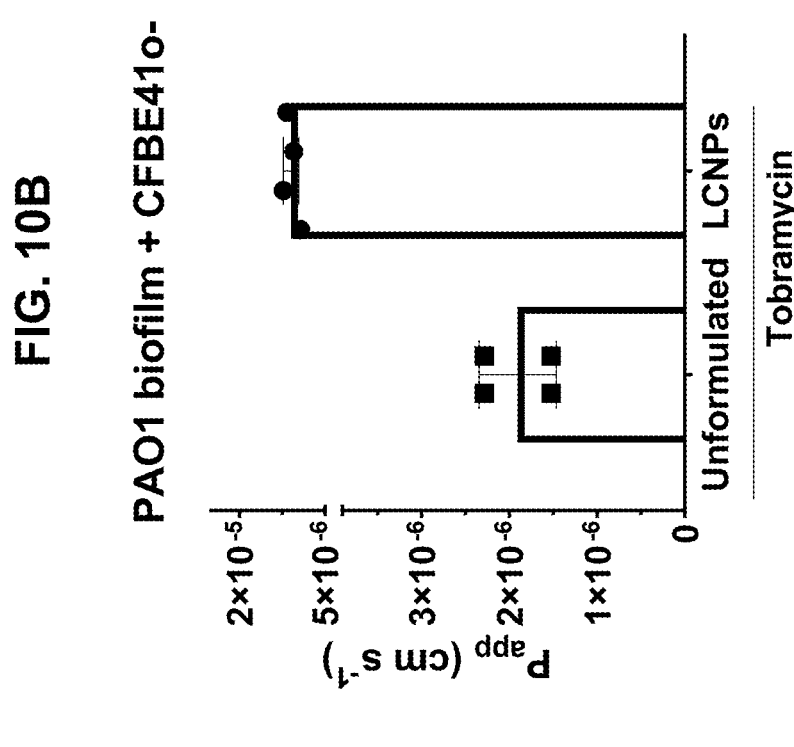
FIGS. 10A-10B—graphs representing the different permeabilities of tobramycin across the CFBE41o− cell line when it is non-infected and infected with *P. aeruginosa* biofilm (chronic lung infection model). The graphs show the apparent permeability coefficient of nebulised tobramycin (12 μg) as an unformulated solution or loaded in MO-LCNPs (0.05 mg/mL) using the Aerogen® Pro (vibrating mesh nebuliser) and nebulisation chamber across CFBE41o− cells (0.05×10⁶ cells/well in 12 well Transwells® inserts, TEER 448 Ω*cm², p. 4.86) (A) and CFBE41o− (p 4.87, 4.88, 0.05×10⁶ cells/well seeded on Transwell® inserts) infected with PAO1 biofilm (B). Data represented as mean±standard deviation, n=5 (2 independent experiments).
Figure 10B:
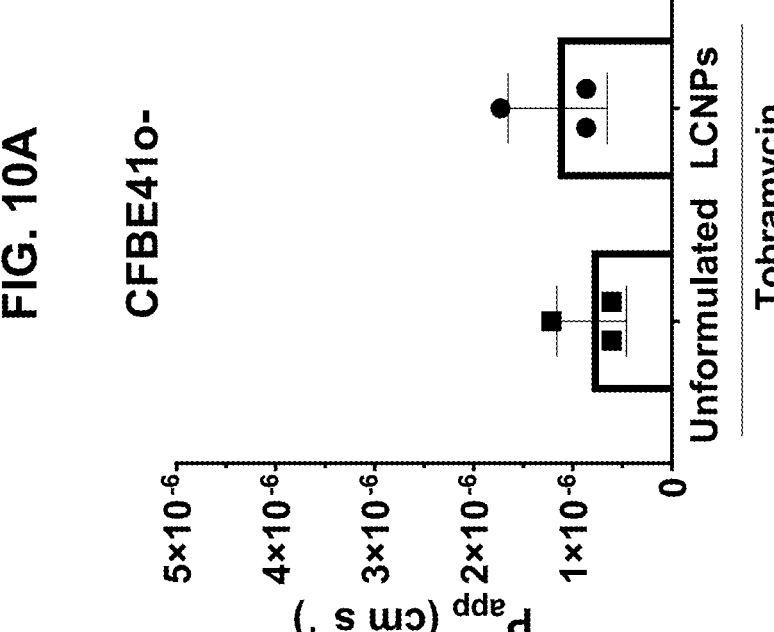

As a small hydrophilic molecule, TOB's transport across a cell monolayer is via a paracellular route and restricted by tight intercellular junctions (De Leo, L., et aL, 2010, *Antimicrobial Agents and Chemotherapy,* 54(4): 1644-1646; and Zambito Y C et al., 2006, *European Journal of Pharmaceutics and Biopharmaceutics,* 64(1): 16-25). Correspondingly, the apparent permeability coefficient of (unformulated) TOB was $8.1 \times 10^{-7}$ cm·s$^{-1}$ (FIG. 10A) and was comparable to the Papp of sodium fluorescein, a gold-standard paracellular transport marker ($6.8 \times 10^{-7}$ cm·s$^{-1}$). The CFBE41o− formed tight junctions through the marked increase in sodium fluorescein's Papp ($8.7 \times 10^{-6}$ cm·s$^{-1}$) following incubation with EDTA, a tight junction disrupter. The LCNPs did not alter the paracellular transport of TOB or sodium fluorescein, with a Papp of $1.2 \times 10^{-6}$ cm·s$^{-1}$ and 1.4×10-6 cm·s$^{-1}$, respectively (P>0.05). As lipid-based particles, the hydrophobicity may increase transcellular transport of the LCNPs and loaded compounds. Compared to the high Papp of the lipophilic dye ($4.0 \times 10^{-6}$ cm·s$^{-1}$), the Papp of the lipophilic fluorescent dye decreased to $2.4 \times 10^{-7}$ cm·s$^{-1}$, following loading in the MO-LCNPs, indicating limited transcellular transport of the LCNPs across the CFBE41o− monolayer.

Limited penetration across the epithelium monolayer indicates that there will be limited systemic transport or absorption of TOB following aerosolisation into the lungs. In CF patients, aerosolised TOB resulted in limited systemic absorption and low bioavailability of 9.13% (Cooney G. F et aL, 1994, *The Journal of Clinical Pharmacology,* 34(3): 255-259). The local administration of TOB to pulmonary tissue is highly valuable to the concentration-dependent effect of aminoglycosides, whereby obtaining sufficient concentrations in the pulmonary tissue is critical to antimicrobial activities, rather than maintaining the concentration for an extended period (Valcke Y R et al., 1990, *European Respiratory Journal,* 3(6): 715-722). Since the LCNPs did not further enhance the permeability of TOB across the bronchial epithelium, this suggests limited systemic exposure of TOB should occur following nebulisation of the MO-LCNPs TOB formulation. Besides maximising the antimicrobial effect, local pulmonary administration also reduces off-target adverse effects of aminoglycosides, including nephro- and ototoxicity (Touw D et al., 1997, *Antimicrobial Agents and Chemotherapy,* 41(1): 184-187).

The sophisticated 3D in vitro cell co-culture model based on human bronchial epithelial cells (CFBE41o−) infected with mature, three-day-old *P. aeruginosa* biofilms at the air-liquid interface, as described above permits biological relevant quantification of the bacterial and human host response to MO-LCNPs TOB treatment compared to the unformulated antibiotic. This unique biologically relevant model mimics a chronic lung infection in the bronchial region. In particular, it is relevant for the pulmonary infections observed in cystic fibrosis patients, where the cell line used, CFBE41o−, contains the CFTR mutation. The transport of TOB across the biofilm and human bronchial epithelial cells was quantified after nebulisation as an unformulated solution or in the MO-LCNPs. While the unformulated and MO-LCNPs TOB demonstrated limited transport across a healthy CFBE41o− cell monolayer, upon *P. aeruginosa* biofilm infection, the tight junctions and barrier function of CFBE41o− is jeopardised and becomes leaky. In corroboration with the visual representation of TOB in biofilms, in the presence of the biofilm and epithelium monolayer, TOB's transport was significantly higher in the MO-LCNPs than the unformulated solution, with a Papp of $1.09 \times 10^{-5}$ cm·s$^{-1}$ compared to $1.91 \times 10^{-6}$ cm·s$^{-1}$, respectively. At the peak of 2.5 h after nebulisation, the MO-LCNPs enabled 99.2% of TOB to reach the basolateral compartment, compared to 15.8% of the unformulated TOB and was similar to the laser scanning confocal micrograph observation. Invariably, LCNPs transport more TOB through the biofilm than the unformulated antibiotic. While the barrier integrity was not determined following infection, previous work suggesting that the tight junctions are compromised explain the increased transport of TOB. Upon clearance of the infection, the epithelial barrier function can re-establish. Considering the single-cell monolayer in the present study lacks additional support, upon bacterial killing, the barrier function of the cells may not have been replaced, further resulting in the increased transport of TOB.

Chronic Infection Model: CFBE41o− and POA1

Consistent with previous findings in a simple in vitro biofilm model and corroboration with the enhanced penetration of TOB from the MO-LCNPs across the biofilm, at 24 h after a single 12 µg nebulised dose to the chronic infection model, TOB's antimicrobial effect was 2-log higher from MO-LCNPs compared to the unformulated antibiotic.

The three-day-old biofilm, containing $4 \times 10^8$ CFU/mL of *P. aeruginosa,* was reduced to $7.4 \times 10^3$ CFU/mL at 24 h after nebulisation with unformulated TOB and $8.5 \times 10^1$ CFU/mL after nebulisation of the MO-LCNPs TOB (FIG. 11A).

Despite the significant, 100-fold enhanced antimicrobial effect from the MO-LCNPs TOB, the unformulated and MO-LCNPs formulation maintained the cell viability of the epithelium monolayer, demonstrating consistent cell viability above 80% after 24 h, observed via LDH assay and wide-field light microscopy (FIG. 11B). Correlated to the transport of TOB across the biofilm and epithelium monolayer, the enhanced penetration of TOB across the biofilm increases the total concentrations of TOB in the biofilm and the antimicrobial effect. As previously demonstrated with TOB, the cationic antibiotic is inactivated by binding to anionic polysaccharides in the biofilms EPS matrix, reducing the amount of TOB that reaches the inner bacterial community to elicit an antimicrobial effect.

Following 48 h post-infection, the effect of TOB from the MO-LCNPs is further increased and did not statistically differ between one or two doses in the 48 h period, leaving 2 CFU/mL and completely eradicating all of the *P. aeruginosa* biofilms from the epithelium, respectively (FIG. 11C). In comparison, after one and two nebulised doses of the unformulated TOB within 48 h, $1.2 \times 10^3$ CFU/mL and $5.4 \times 10^1$ CFU/mL of *P. aeruginosa* remained, respectively. A single dose of the unformulated TOB did not differ in effect between 24 h and 48 h. However, the second dose increased the effect, despite not completely eradicating the infection. The unformulated TOB and MO-LCNPs TOB also maintained the epithelium cell monolayer viability after 48 h and did not adversely affect the host cells (FIG. 11D). Together, the enhanced action of MO-LCNPs TOB formulation against the advanced and biologically relevant, chronic infection model confirms the previous in vitro data in simplified biofilm models and furthers our understanding of the effect of the formulation, which can achieve complete *P. aeruginosa* biofilm eradication.

The assessment of the CFBE41o− cell line barrier via transepithelial electrical resistance (TEER) was compromised and substituted with quantifying sodium fluorescein transport across the cell monolayer. In FIG. 9, the transport of sodium fluorescein across CFBE41o− cells is compared when the cells did and did not demonstrate TEER. When TEER developed with the CFBE41o− cells at 3 days of air-liquid interface (TEER=448 $\Omega \ast cm^2$), the apparent permeability coefficient (Papp) was $6.82 \times 10^{-7}$ cm·s$^{-1}$, and was not significantly different to when no TEER developed (TEER=129 $\Omega \ast cm^2$), the Papp was $1.43 \times 10^{-6}$ cm·s$^{-1}$. The Papp of sodium fluorescein across CFBE41o− cells (with TEER) in the presence of MO-LCNPs TOB was also non-significantly different, at $1.45 \times 10^{-6}$ cm·s$^{-1}$. As a control, the transport of sodium fluoresecein significantly increased upon the addition of EDTA which disrupts the cell barrier, where the Papp was $7.42 \times 10^{-6}$ cm·s$^{-1}$ (originally with TEER) and $7.36 \times 10^{-6}$ cm·s$^{-1}$ (without TEER). Thus, the limited transport of sodium fluoresecin without EDTA demonstrates that the CFBE41o− cells had an intact cell barrier which was not affected by MO-LCNPs.

The complete eradication of the *P. aeruginosa* biofilm from the epithelium is very promising. Previously, the Fluidosom™ technology of TOB eradicated a chronic *P. aeruginosa* respiratory infection in Sprague-Dawley rats following three doses every 16 h, unlike the unformulated TOB (inoculum $1 \times 10^6$ CFU/mL), due to fusing with the bacterial membrane and increasing the amount of TOB in the bacteria (Sachetelli, S., et al., 2000, supra; and Beaulac, C., et al., 1996, supra). The enhanced penetration of TOB from the MO-LCNPs across the biofilm-infected epithelium that leads to the enhanced antimicrobial effect may be attributable to the sub-micron particle size (164 nm) and near-neutral surface charge (−10.2 mV) of the MO-LCNPs. The near-neutral surface charge may further explain the observation of the MO-LCNPs forming a sock-like coating over the biofilm, penetrating the outer layer or EPS matrix of the biofilm. The biofilm's EPS matrix has been shown to inhibit the diffusion of TOB due to the electrostatic interactions. Despite the lower amount of MO-LCNPs penetrating, it is enough for the released TOB to overcome the electrostatic hindrance and complete the rest of the journey to eradicate the bacterial biofilm. However, as observed with comparison to another liposomal formulation, there may be other mechanisms involved in the enhanced action related to the unique structure of the LCNPs.

EXAMPLE 2

*C. elegans* Infection Model

The aim of this study was to investigate the effect of monoolein liquid crystal nanoparticles loaded with tobramycin in a whole invertebrate animal infection model using *Caenorhabditis elegans* (*C. elegans*). The safety of monoolein and phytantriol LCNPs were compared in healthy *C. elegans* followed by comparing non-toxic LCNPs tobramycin formulations to unformulated solutions in *P. aeruginosa* infected *C. elegans*.

Methods

*C. elegans* are free-living transparent nematodes with similar innate immune pathways as humans and are valuable animal infection models (Kirienko N V et al., 2013, *Cell Host & Microbe*, 13(4): 406-416). Synchronised *C. elegans* were grown until L4 stage (eggs incubated at 25° C. for 72 h) on *E. coli* OP50 on nematode growth medium (NGM) agar. *C. elegans* were harvested and healthy nematodes were divided in groups of 20 in OGM medium (95% M9 buffer, 5% brain heart infusion broth, 10 μg/mL cholesterol). Healthy nematodes were exposed to various concentrations of MO- and PHY-LCNPs to determine non-toxic concentrations ranges. In a subsequent experiment, healthy nematodes were then exposed to various concentrations of tobramycin (TOB) as an unformulated solution or load in MO- and PHY-LCNPs (0.05 mg/mL).

For the infection study, an overnight culture of *P. aeruginosa* (PAO1) was diluted to an OD of 0.1 and 200 μL was seeded onto NGM (50 mM NaCl and 0.35% peptone) agar plates for 12 h at 37° C. After 12 h, the collected L4 stage nematodes were incubated on PAO1 seeded agar plates and allowed to feed on the bacteria for 6 h at 25° C. (Uccelletti D et al., 2010, *Antimicrobial Agents and Chemotherapy* 54(9), 3853-3860). Thereafter, the nematodes were removed from the agar and washed multiple times to remove PAO1 from the outside and the nematodes were split into groups of 20 in OGM medium. Besides the non-treated control, the infected nematodes were treated with various concentrations of tobramycin as an unformulated solution or loaded in MO-LCNPs.

In both the healthy and infected nematodes study, nematodes were assessed as live or dead under a bright field microscopy through either being curled and moving (live) or stiff and non-moving (dead) at 4 h, 24 h and 48 h post treatment. The percentage of live nematodes to the total number of nematodes in the samples was compared to healthy, non-treated controls to compute the % survival.

Following 24 h and 48 h, samples of the nematodes were taken and washed with M9 buffer containing 1 mM sodium azide and then 0.01 M PBS before being counted. The nematodes were then mechanically disrupted via vortex mixing in tubes with 200 mg of 1.0 mm silicon carbide beads (BioSpec Products, Bartleville, OK) for 10 mins (Richter K et al. 2017, *Frontiers in Cellular and Infection Microbiology*, 7: Article 280). The disrupted nematodes and bacterial suspensions were serial diluted and spot plated on *Pseudomonas* isolation agar for colony forming units (CFU) counting to determine the CFU per nematode.

Results

As per cell toxicity data in Example 1, the MO-LCNPs were less toxic to the *C. elegans* than the PHY-LCNPs, whereby at 0.05 mg/mL of MO-LCNPs did not harm the nematodes for up to 48 h (FIG. 12). As PHY-LCNPs resulted in more than 20% killing of the nematodes with all concentrations tested following 48 h, further studies were only continued with MO-LCNPs.

Following PAO1 infection, less than 10% of the nematodes survived at 24 h and less than 5% survived at 48 h (FIG. 13A and 13C). Using a GFP-tagged PAO1, the bacteria was visualised to line the gastrointestinal tract of the nematodes. In healthy nematodes, tobramycin (3-60 µg/mL) did not adversely affect the nematodes when dosed as an unformulated solution or loaded in the MO-LCNPs (0.05 mg/mL). In PAO1 infected nematodes, 24 h treatment with unformulated tobramycin at 3 µg/mL did not increase the survival of the nematodes from the non-treated control (13% survival), while 6 µg/mL, 15 µg/mL and 60 µg/mL of unformulated tobramycin improved the survival to 65%, 83% and 87%, respectively. In comparison, tobramycin loaded in MO-LCNPs drastically improved the survival of the infected nematodes at 3 µg/mL and 6 µg/mL (P<0.01) achieving similar survival of healthy, non-infected *C. elegans* that was between 87% and 94% (FIG. 13A). The increased survival of the *C. elegans* from the MO-LCNPs formulated tobramycin was due to the enhanced bacterial killing, where a greater than 1-log reduction in PAO1 was achieved at all concentrations tested compared to the unformulated solution (FIG. 13B). While a higher concentration of unformulated tobramycin (15 µg/mL and 60 µg/mL) was better than no treatment and killed 1 log of bacteria (compared to control), tobramycin loaded in the MO-LCNPs resulted in a total 2.5 log reduction in PAO1 compared to the non-treated controls.

At 48 h, 3 µg/mL of unformulated tobramycin still did not improve the survival of the infected nematodes (7% survival) compared to the untreated and 6-60 µg/mL resulted in an average survival of 65%, which was significantly different to controls (P>0.05). Again, tobramycin loaded in the MO-LCNPs improved the survival of *C. elegans* at all concentration (P<0.01), maintaining 85% of the nematode population (FIG. 13C). Tobramycin loaded in the MO-LCNPs further had an advanced antimicrobial effect at 48 h, with the 60 µg/mL completely eradicating the PAO1 infection compared to 2-log of PAO1 surviving following unformulated tobramycin treatment. Similar to our previous results in the chronic lung infection model in Example 1, one single treatment of tobramycin loaded MO-LCNPs achieved complete bacterial eradication within 48 h. A strong concentration effect was observed with the tobramycin loaded in the MO-LCNPs advancing the antimicrobial effect consistently from 1.5-log compared to the unformulated solution (FIG. 13D). The enhanced nematode survival from tobramycin loaded in the MO-LCNPs was likened to maintaining a less than 2.5-log of PAO1 infection compared to an approximate 4-log PAO1 infection in non-treated and unformulated tobramycin treated nematodes.

The prolonged survival and advanced infection eradication of the PAO1 systemic infection in the live invertebrate animal model, *C. elegans* by tobramycin loaded in MO-LCNPs is another exemplary feature of the nanostructured liquid crystal carrier. Compared to previous experiments where the carrier has been modelled as a topical delivery system, the systemic administration in the *C. elegans* model opens other opportunities for the LCNPs formulation.

EXAMPLE 3

Inhalation Treatment for Non-Cystic Fibrosis Bronchiectasis

The results of the study in Example 1 can be expanded towards the treatment of additional disorders associated with bacterial biofilm infections. For example, non-cystic fibrosis bronchiectasis (NCFB) is a chronic lung disease characterised by irreversible lung damage and recurring infections. In NCFB, initial lung damage is caused by inhalation of toxic substances (fumes, gases, coal dust), or disease (e.g. cystic fibrosis, low antibody levels, tuberculosis, whooping cough, measles) resulting in abnormal widening of airways. The wider airways promote accumulation of mucus that provides a breeding ground for pathogens. The vicious circle hypothesis for NCFB (Cole P J 1986, *Eur. J. Respir. Dis. Suppl.*, 147: 6-15) suggests that repeated infections and inflammation leads to the progressive loss of lung function, poor quality of life, high co-morbidity and increased mortality due to lung (50%) or heart failure (25%). In Australia 12,500 hospitalisations were associated with NCFB (2006-2007), affecting older age groups and indigenous Australian children more frequently (14 in 1000 children vs 0 in 1000 in non-indigenous children). Worldwide, the prevalence of NCFB has increased substantially for all age groups (e.g. it doubled in the UK between 2003 and 2013) with an overall prevalence between 53 and 566 cases per 100,000 inhabitants. Owing to more hospital days, increased gravity of other lung diseases and the requirement for repeated infection treatment the costs for the management of NCFB are significant, burdening health systems with billions of dollars annually.

Unfortunately, conventional antibiotic treatment often fails to clear chronic infections, and this is largely due to the formation of biofilms. The antimicrobial compositions characterised in Example 1 may be used to disrupt the vicious circle by treating biofilm-associated bacteria using a responsive inhalable antibiotic delivery system with dramatically enhanced antimicrobial effect.

*Pseudomonas aeruginosa* (PA), nontypeable *Haemophilus influenzae* (HI) and *Moraxella catarrhalis* (MC) are the most frequently found pathogens in the sputum of bronchiectasis patients, whereas *Streptococcus pneumoniae* (SP), *Staphylococcus aureus* (SA) and methicillin resistant SA (MRSA) are less common. The presence of PA is associated with accelerated disease progression, a more rapid decline in lung function and higher mortality, emphasising the importance of effective infection control. It is currently not clear if co-existence of different pathogens affects the clinical progression of the disease. However, based on experience from other multi-microbial infections, a negative impact on successful infection management cannot be excluded. Building on positive outcomes in cystic fibrosis patients and clinical experience, guidelines recommend early eradication of PA to reduce the progression of NCFB and mortality.

Current treatment guidelines for NCFB aim to increase lung function and quality of life by i) improving mucus clearance; ii) decrease inflammation and iii) prevent, suppress or eradicate infections. For NCFB patients experiencing multiple exacerbations per year the European Respiratory Society guidelines recommend oral, parenteral or inhaled antibiotics (tobramycin, gentamicin, colistin, ciprofloxacin) to prevent further episodes. Compared to oral or parenteral formulations, inhaled antibiotics have the advantage of delivering increased amounts of antibiotics directly to the lung while reducing systemic toxic side effects and development of antibiotic resistance. Inhaled antibiotics have proven important medicines in cystic fibrosis, resulting in reduced exacerbations and improved lung function. However, there are currently no inhaled antibiotic treatments approved for NCFB as the limited number of clinical studies have not demonstrated sufficient efficacy to regulatory bodies.

The inability of conventional, inhalable antibiotics to clear chronic infections is due to the formation of biofilms. Chemically, the porous matrix of the biofilm is composed of gel-like extracellular polymeric substances (EPS), mainly polysaccharides and extracellular DNA. The biofilm matrix protects the bacteria from antibiotics through physicochemical interactions (e.g. between positively charged aminoglycoside antibiotics and the negatively charged biofilm surface) or by enzymatic inactivation e.g. beta-lactamase. As a result, biofilm-associated bacteria such as PA in NCFB demonstrate extreme (up to 1000-fold) tolerance to antimicrobial therapy compared to planktonic bacteria. Despite repeated administration of high doses, currently available antibiotics therefore fail to provide high or long enough exposure for effective biofilm eradication.

In Example 1, we demonstrated dramatically increased antimicrobial efficacy of LCNP loaded with antibiotic (LCNP-AB) compared to unformulated antibiotic and liposomal antibiotic. This is a significant finding considering the lack of innovative antimicrobials in the discovery pipelines of pharmaceutical industry. Motivated by our results, we propose an inhalable, infection-responsive liquid crystal antibiotic delivery system with the capacity to boost antibiotic efficacy and eradicate PA biofilm in NCFB.

To this end, the response of *Pseudomonas aeruginosa* (PA) in planktonic and in biofilm mode of growth to antibiotic treatment will be mapped and characterised. PA strains, isolated and genotyped from non-CFB patients will be obtained, and strains will be selected that grow biofilms and demonstrate intermediate and resistance to antibiotics (see below).

Planktonic bacteria: The minimum inhibitory concentration (MIC) and minimum bactericidal concentration (MBC) of the isolates in the planktonic mode of growth will first be quantified according to guidelines of the Clinical and Laboratory Standards Institute (CLSI) against the antibiotics tobramycin, gentamicin, amikacin, ciprofloxacin and colistin. Antibiotics will include freshly prepared aqueous stock solutions and commercially available inhalable antibiotics (currently only approved for CF) to account for any potential formulation-derived effects on antimicrobial activity. Comparison with the MIC breakpoints published by CLSI and the European Committee on Antimicrobial Susceptibility Testing (EUCAST) will inform the degree of susceptibility (susceptible, intermediate or resistant) of the isolates to the tested antibiotics.

Biofilms: Biofilms of PA isolates will be grown according to standard protocols to determine the minimum biofilm inhibitory concentration (MBIC) and the minimum biofilm eradication concentration (MBEC) in pre-formed biofilms using MBEC multi-well plates (Thorn C R et al., 2018, *ACS Applied Bio Materials*, 1(2): 281-288; Thomas N et al., 2016, *J. Pharm. Sci.*, 105(10): 3115-3122). The MBIC and MBEC will be compared with MIC breakpoints and provide the benchmark for the antimicrobial activity for LCNP-AB developed in the further experiments described below. Since the physicochemical properties of biofilms will affect their biological interaction with antimicrobial treatments it is important to understand the composition and properties of the EPS components (proteins, extracellular DNA, polysaccharides). The total biofilm mass (bacteria plus matrix) will be quantified by spectrophotometry following crystal violet staining (Albayaty Y N et al., 2019, *Int. J. Pharm.*, 566: 329-341). The mass ratios of EPS components will be determined, and components will be characterised for molecular weight and charge using gel permeation chromatography and phase analysis light scattering, respectively (Wingender J et al., Isolation and biochemical characterization of extracellular polymeric substances from *Pseudomonas aeruginosa*. In: Doyle R J, editor. Methods EnzymoL 336: Academic Press; 2001. p. 302-14). Protein content will be quantified by BCA assay, DNA by electrophoresis, while total carbohydrates will be quantified using the established calorimetric method by DuBois (Thorn C R et al., 2020, supra; Tetz G V et al., 2009, *Antimicrob. Agents Chemother.*, 53(3): 1204).

Building on our successful studies in Example 1, and following clinical guidelines, tobramycin, gentamicin, amikacin, ciprofloxacin and colistin will be encapsulated in LCNP. The LCNP will be bio-pharmaceutically and physico-chemically characterised (size, supramolecular structure, drug load and release) in the absence and presence of bacterial lipase using techniques routinely employed (Thorn C R et al., 2020, supra). Biofilm penetration of LCNP-AB and LCNP-AB-bacteria interactions will be analysed in depth using fluorescently labelled antibiotics, bacteria and LCNP in combination with confocal microscopy (Pestrak M J et al., 2019, *Antimicrob. Agents Chemother.*, 63(6): e00234-19 doi: 10.1128/AAC.00234-19; Driever C D et al., 2011, *Soft Matter.*, 7(9): 4257-4266; Albayaty Y N et al., 2020, *J. Mat. Chem. B.*, 8: 1672-1681). These studies will collectively inform the structure-function relationships and will unravel the mode of action of our technology.

The antimicrobial efficacy of antibiotic-loaded LCNP will be evaluated in an advanced in vitro co-culture biofilm model that models the airway system. To this end the model uses primary human bronchial epithelial cells cultured at the air-liquid interface (ALI) on a Transwell® membrane. This allows cell differentiation and produces a pseudostratified epithelium. Combined with cilia expression, the functional mucociliary transport resembles the air-facing bronchial epithelium in the human airways (Crabbé A et al., 2014, *Pathogens and Disease*, 71(1): 1-19). Upon reaching confluency (confirmed by transepithelial resistance (TER) measurement), a 72-hour *Pseudomonas* biofilm (pre-grown separately in petri dish) is transferred to the cell layer. The co-cultured model can be maintained for at least one week with both the diffusional and immunological barriers that usually cannot be replicated in vitro. Importantly, the model allows the administration of aerosolised treatments (see further below) and enables multiple read-outs, including bacteria burden (as significantly demonstrated in Example 1), cell viability (LDH assay) and inflammatory responses (ELISA). Penetration of antibiotic and LCNP-AB will be quantified by analysing the receiver compartment for antibiotics by mass spectrometry and fluorescence and qualitatively by confocal laser scanning microscopy.

In order to achieve suitable lung deposition and efficacy, the inhaled formulation requires an aerodynamic size of pm and needs to be physically and chemically stable. The preferred method of delivery is via dry powder inhalation; since high doses of medication can be delivered over shorter periods of time to that of a nebuliser without the associated risks of nebuliser induced damage to the LCNP-AB ultrastructure and/or long-term stability issues from liquid storage. In order to develop an inhalable LCNP-AB system, spray-drying, lyophilisation and milling techniques will be evaluated to produce micron-sized powders. A matrix of particle production variable will be undertaken (such as feed rates, drying temperature, co-solvent type and concentration etc as well as the use of stabilising excipients) and output powders evaluated. Inhalation powders will be evaluated in terms of their physico-chemical properties including size distribution (laser diffraction), ultrastructure (x-ray diffraction), moisture and thermal properties (DSC, TGA and DVS) and morphology (SEM). Optimised inhalation powders will be evaluated using pharmacopeia FDA/TGA recommended tests with a gold standard dry powder inhaler (RSO1, Plastiape). Tests include aerodynamic characterisation using mass-based cascade impactors, in-line laser diffraction, dose uniformity and stability studies.

The subject headings used herein are included only for the ease of reference of the reader and should not be used to limit the subject matter found throughout the disclosure or the claims. The subject headings should not be used in construing the scope of the claims or the claim limitations.

EXAMPLE 4

Comparison of Tobramycin Formulations in Chronic *P. aeruginosa* Infection in a Full-Thickness Wound This in vivo study utilised a full-thickness, chronic wound infection model using a pathogenic variant of *P. aeruginosa* in Balb/c mice. The model was used to test the hypothesis that tobramycin-LCNPs have greater in vivo antimicrobial efficacy and wound healing compared to unformulated antibiotic, hence demonstrate its potential as the next generation of directed, topical therapies for untreatable chronic wound infections.

Methods

Model Development

Male and female Balb/c wildtype mice (10-12 weeks old) were obtained from the Australian Resource Centre (ARC, Perth, Western Australia). All animal experiments were conducted in compliance with the guidelines or the care and use of research animals established by the University of South Australia Animal Ethics Committee (University of South Australia AEC), project number U48-20. All mice acclimatised in the Core Animal Facility (University of South Australia, Adelaide, South Australia) over seven days before any intervention began and animals were kept in a 12 h dark/light cycle for the entire study with free access to food and water.

For the model development (pilot study), male and female mice were randomly divided into four groups to investigate (1) 10 mm wound and $10^7$ CFU *P. aeruginosa* infection (n=10), (2) 6 mm wound and $10^6$ *P. aeruginosa* infection (n=6), (3) 10 mm wound and no infection (n=9) and (4) 6 mm wound and no infection (n=6). Anaesthesia was induced by inhalation of 5% isoflurane in 1.5 L of oxygen and maintained during surgery at 2% isoflurane in 1.5 L of oxygen. Pre-operative analgesia was provided 30 minutes before surgery by subcutaneous injection of 0.05 mg/kg of buprenorphine. The backs of the mice were shaved, and depilatory cream (Nair Sensitive, Church & Dwight, Australia) was applied to ensure a hair-free surface. Thereafter, the hair-free skin was cleaned and disinfected with iodine. A full-thickness circular excisional wound was created on the backs of the mice, either 10 mm or 6 mm in diameter, depending on group.

Immediately after wounding, group 1 was inoculated with $10^7$ CFU of bioluminescent *P. aeruginosa* strain (Xen41, PerkinElmer, Waltham, MA, USA) in 10 μL of 0.9% saline. All other mice were covered with an adhesive dressing (Opsite Flexigrid, Smith & Nephew, London, UK). All mice were given soaked food and free access to water for the study. Postoperative analgesia (0.05 mg/kg buprenorphine) was provided 10 h and 24 h post-surgery via subcutaneous administration. After inoculation, mice were imaged using IVIS Spectrum Live Animal Imaging System (PerkinElmer, Waltham, MA, USA) and then daily until sacrifice to quantity radiance (photons/s) of the bioluminescent bacteria in the wound and correlate to the infection load, as previously described (Abbott C A et al., 2013, *Contributors, in Handbook of Proteolytic Enzymes,* N. D. Rawlings and G. Salvesen, Editors. 2013, Academic Press. p. xxxv-xlviii). Using built-in Living Image R software, regions of interest (ROI) were selected surrounding the wound to quantify the total photon emission following established protocols (Haidari, H., et al., 2021, *Acta Biomaterialia,* 128: 420-434; Kopecki, Z., et al., 2009, *Journal of Investigative Dermatology,* 129 (8): 2031-2045).

For group 2 (6 mm wound+$10^6$ CFU infection), the mice were allowed to recover for 24 h post wound surgery. Thereafter they were inoculated with $10^6$ CFU of *P. aeruginosa* Xen41 in 10 μL 0.9% saline before imaging using the IVIS. After daily IVIS imaging, wounds were digitally photographed for all mice, and dressings were replaced with fresh sterile dressings. Mice were checked twice daily for clinical signs, weights and temperature using a non-contact thermometer (MicroLife NC150, StarkMed, NSW, Australia). On the sixth day of the study, all mice were sacrificed via $CO_2$ asphyxiation and cervical dislocation. Under sterile conditions, wounds were excised, and major organs (heart, lungs, liver, spleen and cardiac bleed) were collected. The wounds were halved through the centre, where half were subjected to fixation in 4% formaldehyde in PBS and subsequent hematoxylin and eosin (H&E) staining for histological analysis. The other half was bisected, a quarter was used for bacterial colony counts and the remaining quarter was fixed in 4% formaldehyde and processed for either crystal violet staining or scanning electron microscopy. Organs were enriched in blood agar and chocolate agar media for bacterial pathology and analysis, followed by Gram stains, as per standard protocols.

After the pilot, it was determined that a 6 mm wound+$10^6$ CFU *P. aeruginosa* infection was the appropriate model to proceed with. Following the same procedure as above, male and female mice were wounded with a 6 mm circular full-thickness wound under anaesthesia and pain relief. After 24 h recovery period, they were inoculated with $10^6$ CFU of *P. aeruginosa* Xen41 in 10 μL 0.9% saline and imaged using the IVIS Spectrum Live Animal Imaging System (PerkinElmer, Waltham, MA, USA).

Once the infection had stabilised at day three, the mice were randomly split into four groups and treated with 50 μL of (1) 15 μg tobramycin (unformulated) in 0.9% saline, (2) 15 μg tobramycin-LCNPs, (3) no antibiotic containing LCNPs (equivalent amount to group 2~1 mg/mL) and (4) 0.9 % saline. All treatments were placed directly on the wounds and allowed to rest for 60 seconds before being re-dressed with a fresh, sterile adhesive dressing. Treatments were repeated every 24 h for three days and monitored for the bacterial burden and digital photographs. On day six, mice were sacrificed as described above.

Bacterial Enumeration

The total amount of viable *P. aeruginosa* Xen41 remaining in the excised wounds was determined via CFU spot plating under sterile conditions and further confirmed via bioluminescent imaging. The wound tissue collected was suspended in 1 mL of sterile 0.9% saline and weighed. The tissues were homogenised to extract bacteria into suspension via vortex mixing for 10 minutes. 20 µL of the homogenate was serially diluted in 180 µL of 0.9% saline+0.05 % Tween 80, and 20 µL was spot plated onto *Pseudomonas* selective agar. Plates were incubated for 18 h at 30° C. to enumerate single colonies for counting.

Macroscopic and Microscopic Analysis of Wound Healing

Digital photographs of the wounds that were taken daily (day zero to six) were used for the macroscopic assessment of healing using ImageJ software. The images were calibrated to a ruler to measure the wounds length, gape and surface area, as previously described (Abbott C A et al., 2013, supra). The microscopic analysis was completed with histology assessments. Following overnight fixation in 4% (v/v) formaldehyde, collected wound halves were routinely processed into paraffin, and 4 µm thick sections were cut using a semi-automated rotary microtome (HistoCore MultiCut, Leica Biosystems, Melbourne, Australia). The sections were stained for haematoxylin and eosin using established protocols (Kopecki, Z., et al., 2009, supra). Following, all sections were imaged via NanoZoomer (S60 Digitial slide scanner, Hamamatsu Photonics, Japan) and analysed using NDP.view2 Viewing software (Hamamatsu Photonics, Japan) to microscopically assess the healing via measurement of wound length, gape and percentage of wound re-epithelisation following previously used protocols (Haidari, H., et al., 2021, supra).

Statistical Analysis

Data are reported as mean±standard deviation to show the variability of data. Student t-tests assessed the difference in unformulated tobramycin and tobramycin-LCNPs activity in vitro. One-way or two-way analysis of variance (ANOVA) followed by Tukey's or Dunnet's multiple comparison tests assessed the differences between the in vivo data as described in respective figure captions. All tests were performed using GraphPad Prism (version 9.1.0 for Windows; GraphPad Software, La Jolla, CA).

Results and Discussion

Antimicrobial Efficacy

Figure 14A:
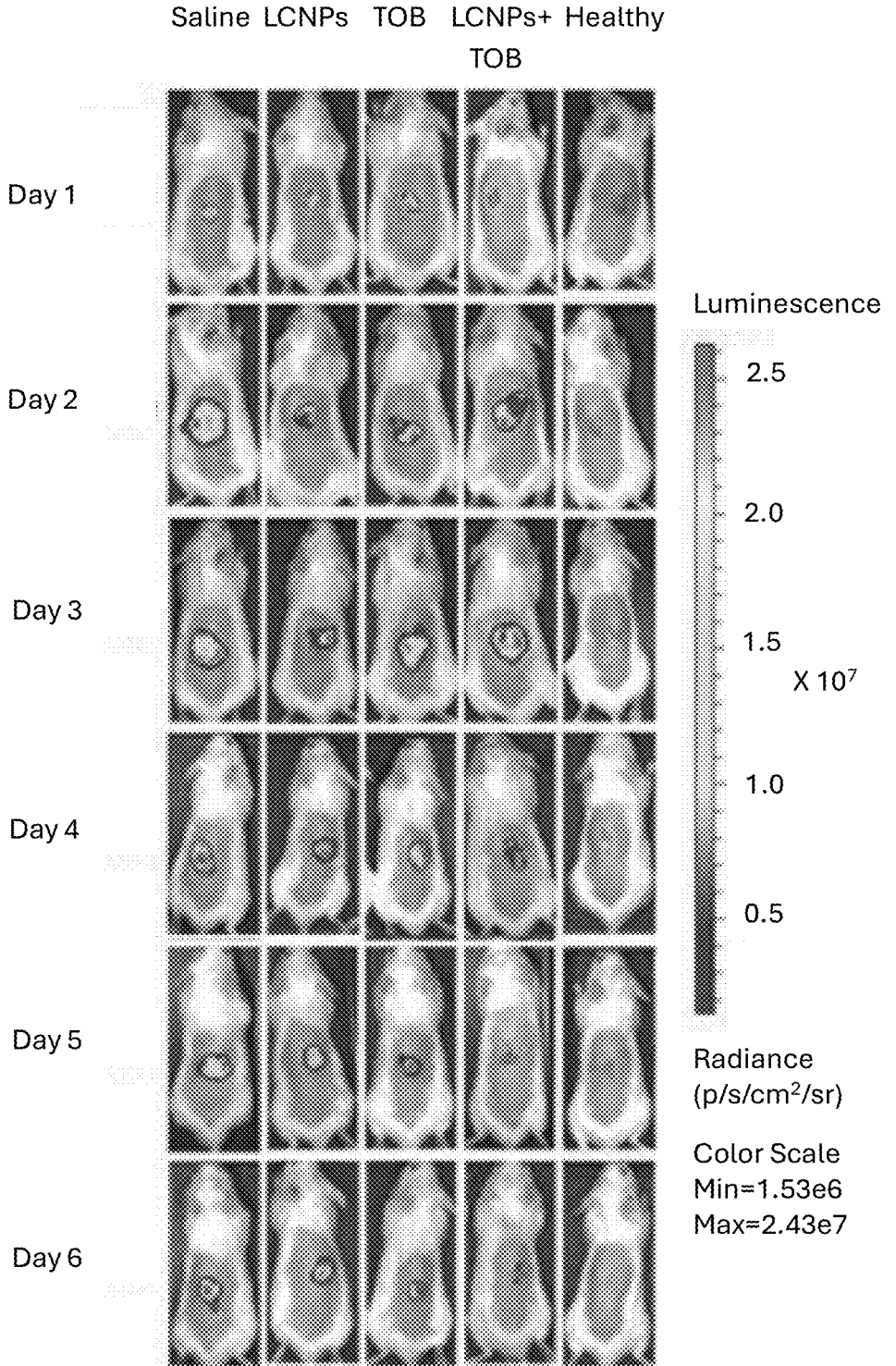

To examine the effectiveness of tobramycin-LCNPs compared to the unformulated antibiotic, the chronic biofilm 6 mm full-thickness wound infection model developed in Balb/c mice was employed. Treatments were applied as a solution or (LCNP) suspension and commenced on day three, as the *P. aeruginosa* infection stabilised as determined by no change in the bacterial load. As shown in the model development, an initial inoculation of $10^6$ CFU (equivalent to $10^5$ photons/s), *P. aeruginosa* grew exponentially until it reached $5 \times 10^8$ photons/s and plateaued. In FIG. 14A, after each once-daily dose of unformulated tobramycin, there was no statistical change in the infection level compared to wounds treated with saline (P>0.99). At day six, after three doses of unformulated tobramycin, there was no statistical difference in the *P. aeruginosa* load compared to the saline control, which was also confirmed by CFU analysis ($5 \times 10^6$ CFU of *P. aeruginosa* remained, compared to $1 \times 10^7$ CFU, respectively, P>0.99, FIG. 14B).

Consistent with in vitro data, the treatment with tobramycin LCNPs reduced the bacterial load of the infected wounds by 2 $\log_{10}$ compared to unformulated tobramycin solution (FIG. 14B, P<0.0001). Following a single dose of tobramycin-LCNP the bacterial load was significantly lower compared to unformulated tobramycin and saline (P<0.05). While the administration of two doses of tobramycin-LCNPs coincided with a significant reduction in bacterial load (P<0.0001), unformulated tobramycin remained ineffective even after three doses, as observed via the bioluminescent data over time in FIG. 14A. This was also demonstrated visually in the micrographs in FIG. 14C, by the decrease in the bioluminescence signal after tobramycin LCNP treatment at days 4, 5 and 6. At the conclusion of the study (day 6) $1 \times 10^3$ CFU/g were extracted from wounds treated with tobramycin-LCNPs (FIG. 14B). The corresponding IVIS signal showed an exponential decrease from day 4 to day 6, trending from $5 \times 10^6$ to $1 \times 10^5$ and $5 \times 10^4$ photons/s, respectively (FIG. 14A). As expected, the blank LCNPs (containing no antibiotics) did not exert any antimicrobial effect over the course of the study, as confirmed by bioluminescence (FIG. 14A) and viable cell counts at day six (FIG. 14B).

Wound Healing Efficacy

Figures 15A, 15B:
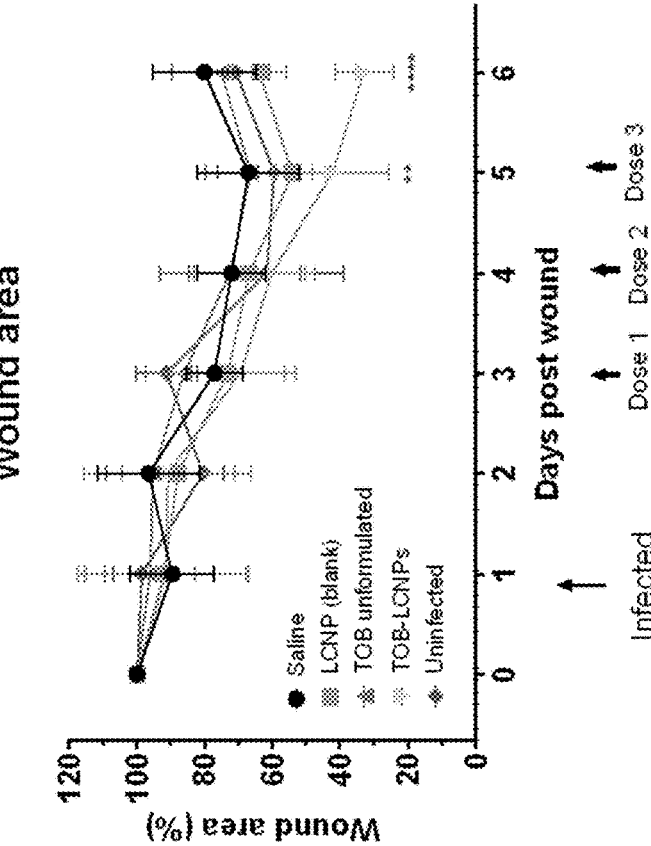
FIGS. 15A-15C—macroscopic wound healing analysis. (A) Wound area percentage over the course of the study and in response to treatments. (B) Dermal gape of the wound during the course of the study, data represented as mean±standard deviation, n=8 mice, =P<0.01 and **=P<0.0001, assessed via two-way ANOVA followed by Dunnet's multiple comparison test. (C) Representative digital photographs of the wounds during the course of the study and concerning different treatments.

Tobramycin-LCNP treated wounds began to heal at a similar rate to non-infected wounds. Most differences in wound healing efficacy were observed in days 4-6 of the trial trial as this coincided with the greatest differences in bacterial load following treatment. On day five, after application of two doses of treatment, the macroscopic wound area for tobramycin-LCNP treated wounds was 42±16% compared to 59±15% for non-infected wounds (FIG. 15A, P<0.05). Additionally, the tobramycin-LCNP treated infected wounds showed significant smaller wound area (42±16%) compared to the infected wounds treated with saline, unformulated tobramycin and LCNPs containing no antibiotic had a total area of 66±15%, 66±13% and 54±5% of the original wound, respectively (FIG. 15A). On day six, after three doses of the tobramycin-LCNP, the area of the infected wound was 34±8%, compared to 64±8%, 75±18% and 80±15% for the no antibiotic LCNPs, unformulated tobramycin and saline-treated wounds, respectively (FIG. 15A, P<0.0001). Notably, the uninfected wound area was 71±1%, resulting in a delayed wound closure.

Figure 15C:
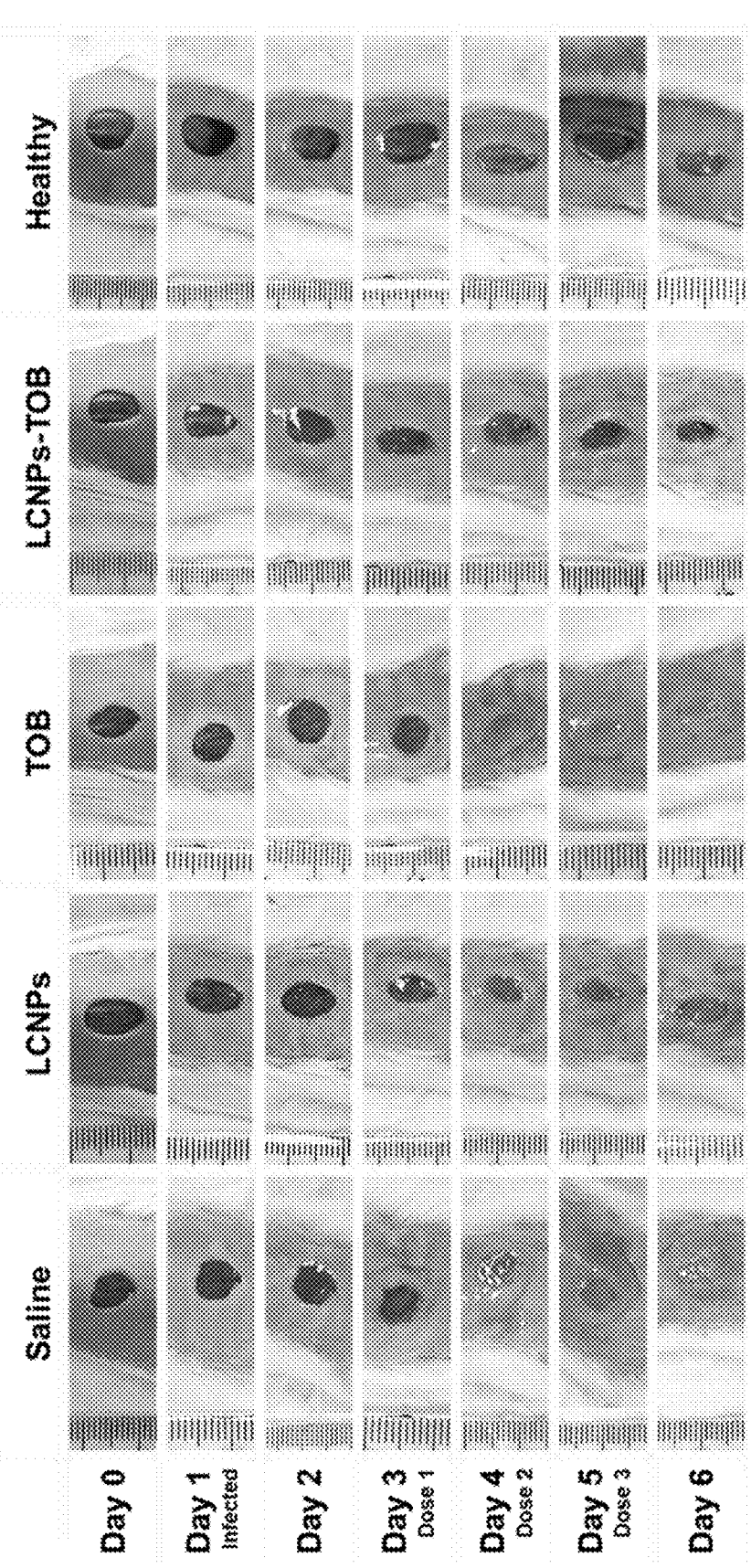

Macroscopically, the dermal gape of the wound was not statistically different between tobramycin-LCNPs and the non-infected wounds on days five and six (P=0.83 and >0.99, respectively, FIG. 15B). Additionally, on days five and six, the dermal gape of tobramycin-LCNPs treated wounds (55±14% and 51±9%, respectively) were statistically smaller from saline (81±8% and 89±11%), unformulated tobramycin (88±11% and 77±10%) and no antibiotic LCNPs (76±6% and 78±6%) treated wounds (P<0.001, and <0.0001, respectively). In FIG. 15C, the representative digital images of the chronic *P. aeruginosa* infection wounds are depicted. The saline, unformulated tobramycin and no antibiotic containing LCNP treated wounds show clear signs of wound infection including maceration of wound edges, thick biofilm and EPS covering the wound surface and lack of healthy granulation tissue and healing. In comparison, tobramycin-LCNP treated wounds have an appearance resembling uninfected wounds at day 5 and 6 of the trial with evidence of healthy granulation tissue and progressive wound healing and contraction.

In conjunction with the macroscopic analysis, the histology demonstrated that the wound length was statistically smaller after three doses of tobramycin-LCNPs treatment (4.0±0.4 mm) compared to the saline control (7.8±0.9 mm), unformulated tobramycin (7.6±0.9 mm) and the LCNPs containing no antibiotic (6.8±0.7 mm) treated wounds (52% improvement, P<0.0001), as shown in FIG. 16A. The uninfected wounds (5.9±1.9 mm) were also smaller compared to the saline-treated infected wounds (P=0.016). The trend for the tobramycin-LCNPs to increase the rate of dermal gape closure at a rate faster than saline control, unformulated antibiotic, and no antibiotic LCNP treated wounds was also observed following histological analysis. On day six of the trial, the dermal gape assessment was similar between the macroscopic and histology analysis, where, as observed in FIG. 16B, tobramycin-LCNPs treated wounds had a significantly smaller dermal gape of 3.8±0.7 mm, compared to 5.4±1.1 mm, 5.2±0.8 mm and 5.3±0.5 mm for saline, unformulated tobramycin and no antibiotic LCNPs, respectively (P=0.015).

Figure 16D:
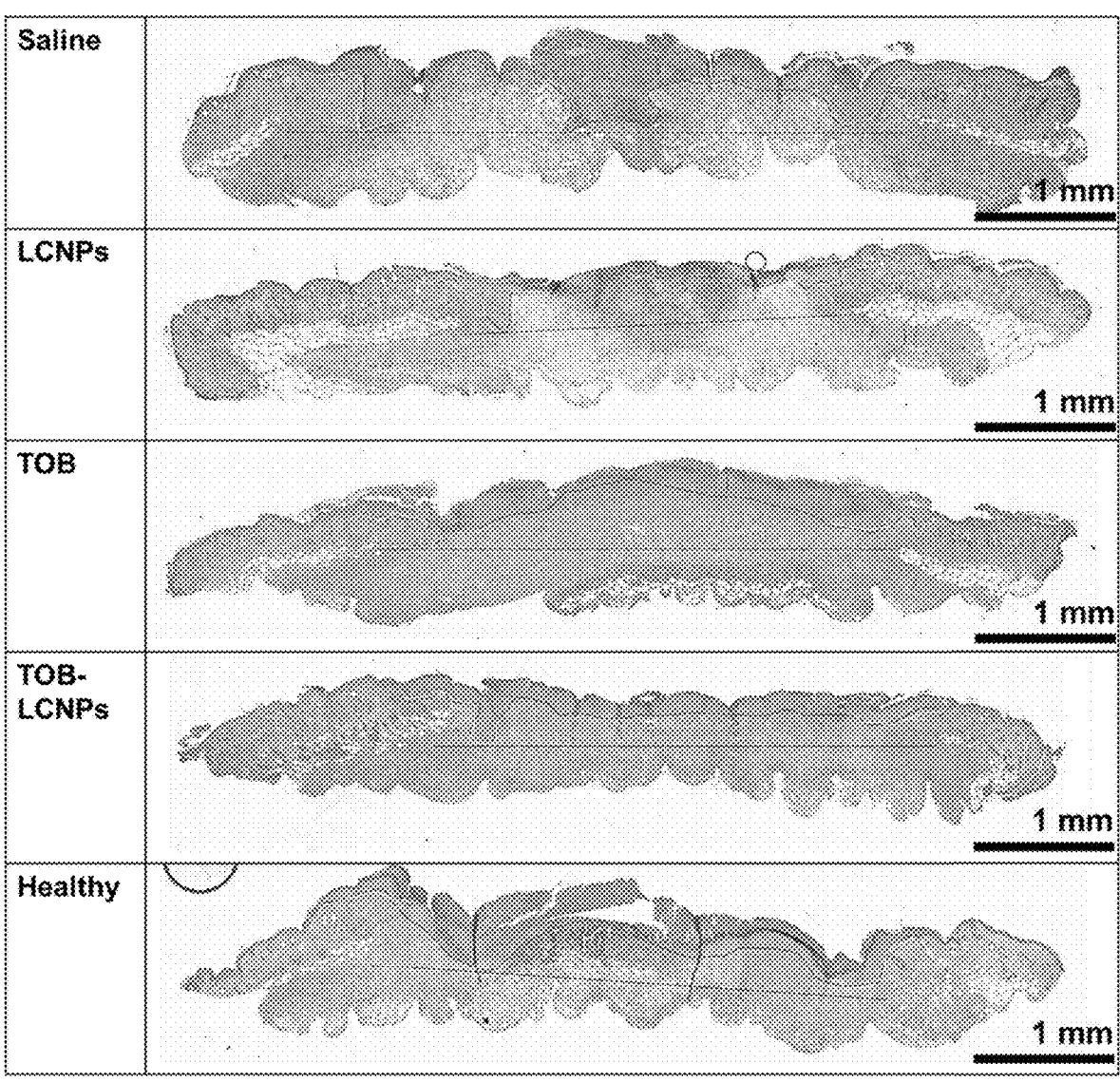

Furthermore, the tobramycin-LCNPs treatment resulted in a significantly higher rate of wound reepithelization (88±14%) compared to saline (36±20%), unformulated tobramycin (41±8%) and no antibiotic LCNPs (62±11%) treated wounds (P<0.0001, FIG. 16C). The uninfected wound showed an increased reepithelization compared to the saline-treated infected wound of 71±15% (P=0.003), similar to tobramycin-LCNPs treated infected wounds (P=0.186). Representative H&E-stained wound cross-sections are presented in FIG. 16D for each respective treatment following day six of the study. Compared to the tobramycin-LCNPs, a larger wound area was observed for saline. Qualitatively, tobramycin-LCNPs treated and uninfected control wounds appear to have a decreased inflammatory cell infiltrate in the wound matrix compared to no antibiotic LCNPs and tobramycin unformulated treatments, as observed in the microscopic H&E analysis.

Chronic wound infections have a devastating impact on the society, with limited effective antimicrobial therapies available. Currently, there are no effective topical antimicrobial therapies to treat *P. aeruginosa* chronic superficial wound infections. Silver-based therapies have shown to be promising treatment avenue but reported toxicity and adverse reactions to the host when applied for extended periods of time has limited their clinical application. The inability of current antimicrobials to control and treat *P. aeruginosa* chronic wound infections often leads to the administration of intravenous antibiotics, increased patient hospitalisation and increased risk of developing antimicrobial resistance. Intravenous administration is associated with various problems leading to longer hospital stays, increased risk of toxicity and development of antimicrobial resistance. We have developed lipid LCNPs that can improve the efficacy of cationic antibiotics against biofilm infections. Examining the pre-clinical potential of this platform therapy requires rigorous examination of efficacy and safety in preclinical models of biofilm wound infection.

Developing a stable, chronic *P. aeruginosa* infections in a full thickness wound in mice is challenging. Previously, well-characterised models using *Staphylococcus aureus* have been developed and utilised for testing new antimicrobial therapies (Haidari H et al., supra). Wounds of 10 mm diameter or greater that were covered in an adhesive wound dressing developed chronic type infections with biofilm formation (Haidari H et al., 2021, *Biomedicines,* 2021, 9(9): 1182). Classification as a chronic infection confers the wound remains in the inflammatory stage of wound healing rather than progressing to the later stages of wound healing (Leaper D et al., 2015, *Br. J. Dermatol.,* 173(2): 351-358). Here we have developed a robust model that mimics a chronic *P. aeruginosa* infection in full thickness wounds in Balb/c mice.

Topical administration of the unformulated antibiotic tobramycin was ineffective at eradicating the chronic wound infection (FIG. 14). While intravenous administration of tobramycin is used in the clinic, this practice increases the risk of toxic side effects, including nephrotoxicity and ototoxicity due to systemic exposure of antibiotic (Coulthard K P et al., 2007, J. *Cystic Fibrosis,* 6(2): 125-130). The lack of tobramycin efficacy in treating *P. aeruginosa* chronic wounds is due to biofilm formation, and inadequate penetration of the antibiotic into the biofilm matrix (Tseng B S et al., 2013, *Environ. Microbiol.,* 15(10): 2865-78). The efficacy of tobramycin in treating bacterial biofilm infections is hindered by the electrostatic interactions between the cationic antibiotic and the negatively charged biofilm-associated extracellular polymeric substance matrix (Russ H et al., 2006, *J. Liq. Chromatogr. Relat. Technol.,* 21(14): 2165-2181). This renders tobramycin ineffective in being able to penetrate the biofilm and target the inner bacterial community (Tseng B S et al., 2013, supra). While more tobramycin is required to saturate the electrostatic interactions, only a small proportion of the total amount of tobramycin is able to cause an effect on the inner bacterial community (Tseng B S et al., 2013, supra) hence significantly reducing its efficacy.

Using a novel formulation approach, we now demonstrate that three topical administrations of tobramycin-LCNPs significantly reduce the *P. aeruginosa* bacterial bioburden by 1000-fold in wounds in vivo compared to conventional antibiotic treatment or saline control (FIG. 14). Importantly, this approach resulted in significant improvements in wound healing outcomes (FIG. 15). The in vivo data represented here provides preclinical data on the use of tobramycin-LCNP formulation as an important next generation therapy approach to combat *P. aeruginosa* biofilms.

The increased therapeutic effect observed in wounds in vivo is also likely to replicate the similar mechanisms of improved penetration of tobramycin into the bacterial biofilm, hence resulting in an increased total concentration and antimicrobial efficacy. While we only examined a three-day treatment period in this study, the LCNP formulation is hypothesised to eradicate the chronic *P. aeruginosa* infection over a longer period of time, such as a seven-day course. Moreover, the chronicity of the infection was limited to six days due to the pathogen severity and progression to sepsis in saline treated controls, and was therefore unable to showcase the entire course of the infected wound. Further extrapolating the data to understand the time scale and potential for bacterial eradication would be important for further clinical development of the TOB-LCNP formulation. Additionally, quantifying the specific local and systemic exposure to tobramycin to further examine the extent of the treatments antimicrobial efficacy would provide valuable information for future development.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The invention claimed is:

1. An antimicrobial composition comprising:
(i) an antimicrobial agent; and
(ii) a nanostructured liquid crystal carrier,
wherein the antimicrobial agent is contained within the nanostructured liquid crystal carrier, and wherein the nanostructured liquid crystal carrier potentiates the activity of the antimicrobial agent.

2. The antimicrobial composition of claim 1, wherein the nanostructured liquid crystal carrier comprises liquid crystal nanoparticles formed from a lipid in a non-lamellar liquid crystalline structure in an aqueous solvent.

3. The antimicrobial composition of claim 2, wherein the liquid crystal nanoparticles are formed from an amphiphilic lipid.

4. The antimicrobial composition of claim 3, wherein the amphiphilic lipid is selected from monoolein or phytantriol.

5. The antimicrobial composition of claim 2, wherein the liquid crystal nanoparticles have a particle size of about 50 nm to about 500 nm.

6. The antimicrobial composition of claim 1, wherein the antimicrobial agent is one or more of a cationic antibiotic, aminoglycoside antibiotic, antimicrobial peptide, and an antifungal agent.

7. The antimicrobial composition of claim 6, wherein the aminoglycoside antibiotic is selected from one or more of tobramycin, amikacin, gentamicin, kanamycin, neomycin, netilmicin, paromomycin, streptomycin, plazomicin and spectinomycin.

8. The antimicrobial composition of claim 6, wherein the cationic antibiotic is colistin.

9. The antimicrobial composition of claim 1, wherein the antimicrobial agent is contained within the nanostructured liquid crystal carrier at an equal volume to weight ratio to the lipid, or is contained within the nanostructured liquid crystal carrier at a concentration up to about 25% (w/w) of the lipid.

10. The antimicrobial composition of claim 1, wherein the microbial infection is a bacterial infection which is due to a Gram-negative bacterium.

11. The antimicrobial composition of claim 1, wherein the composition is in the form of a liquid, a gel, a suspension, a solid, a semi-solid, or a powder.

12. The antimicrobial composition of claim 1, wherein the composition is formulated for topical administration, parenteral administration, administration by inhalation, and oral administration.

13. The antimicrobial composition of claim 12, wherein the composition is administered by inhalation using a nebulizer or dry powder inhaler.

14. The antimicrobial composition of claim 1, wherein the antimicrobial agent is an aminoglycoside antibiotic selected from one or more of tobramycin, gentamicin, or amikacin, and the nanostructured liquid crystal carrier comprises liquid crystal nanoparticles formed from monoolein or phytantriol.

15. A method for the treatment or prevention of a microbial infection in a subject, the method comprising administering to the subject an effective amount of an antimicrobial composition comprising:
(i) an antimicrobial agent; and
(ii) a nanostructured liquid crystal carrier,
wherein the antimicrobial agent is contained within the nanostructured liquid crystal carrier, and wherein the nanostructured liquid crystal carrier potentiates the activity of the antimicrobial agent.

16. The method of claim 15, wherein the microbial infection forms part of a biofilm in a subject or is in a planktonic state in a subject.

17. The method of claim 15, wherein the subject has become resistant or tolerant to the antimicrobial agent when administered in the absence of the nanostructured liquid crystal carrier.

18. The method of claim 15, wherein the bacterial infection is associated with cystic fibrosis sinopulmonary infections.

19. The method of claim 18, wherein the antimicrobial agent is an aminoglycoside antibiotic selected from one or more of tobramycin, gentamicin, or amikacin, and the nanostructured liquid crystal carrier comprises liquid crystal nanoparticles formed from monoolein or phytantriol.

20. A kit for the treatment or prevention of a microbial infection in a subject, wherein the kit comprises an antimicrobial composition comprising:
(i) an antimicrobial agent; and
(ii) a nanostructured liquid crystal carrier,
wherein the antimicrobial agent is contained within the nanostructured liquid crystal carrier, and wherein the nanostructured liquid crystal carrier potentiates the activity of the antimicrobial agent.

* * * * *